US011884956B2

(12) United States Patent
Bertozzi et al.

(10) Patent No.: US 11,884,956 B2
(45) Date of Patent: Jan. 30, 2024

(54) METHODS FOR DETECTING MYCOBACTERIA WITH SOLVATOCHROMIC DYE CONJUGATES

(71) Applicant: The Board of Trustees of the Leland Stanford Junior University, Stanford, CA (US)

(72) Inventors: Carolyn R. Bertozzi, Stanford, CA (US); Mireille Kamariza, Stanford, CA (US); Peyton Shieh, La Jolla, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 395 days.

(21) Appl. No.: 16/321,815

(22) PCT Filed: Jul. 31, 2017

(86) PCT No.: PCT/US2017/044760
§ 371 (c)(1),
(2) Date: Jan. 29, 2019

(87) PCT Pub. No.: WO2018/023134
PCT Pub. Date: Feb. 1, 2018

(65) Prior Publication Data
US 2019/0169671 A1 Jun. 6, 2019

Related U.S. Application Data

(60) Provisional application No. 62/368,928, filed on Jul. 29, 2016.

(51) Int. Cl.
*C12Q 1/22* (2006.01)
*C12Q 1/04* (2006.01)
*C09B 23/14* (2006.01)

(52) U.S. Cl.
CPC ............... *C12Q 1/04* (2013.01); *C09B 23/14* (2013.01); *G01N 2333/34* (2013.01); *G01N 2333/35* (2013.01)

(58) Field of Classification Search
CPC .................................. C12Q 1/04; C09B 23/14
See application file for complete search history.

(56) References Cited

U.S. PATENT DOCUMENTS

| 6,140,041 A | 10/2000 | Laclair |
| 7,829,181 B2 | 11/2010 | MacDonald et al. |
| 2005/0130253 A1 | 6/2005 | Lye et al. |
| 2007/0140971 A1 | 6/2007 | MacDonald et al. |
| 2015/0219653 A1 | 8/2015 | Rao et al. |
| 2015/0252402 A1 | 9/2015 | Swarts et al. |

FOREIGN PATENT DOCUMENTS

| CN | 109790564 A | 5/2019 |
| EP | 3491144 A1 | 6/2019 |
| WO | 2006065349 A2 | 6/2006 |
| WO | 2006065349 A3 | 10/2006 |
| WO | 2007070181 A1 | 6/2007 |
| WO | 2008026105 A2 | 3/2008 |
| WO | 2008026119 A2 | 3/2008 |
| WO | 2008026105 A3 | 5/2008 |
| WO | 2008026119 A3 | 5/2008 |
| WO | 2009095826 A2 | 8/2009 |
| WO | 2009095826 A3 | 11/2009 |
| WO | 2015145463 A1 | 10/2015 |
| WO | 2016028233 A1 | 2/2016 |
| WO | 2018023134 A1 | 2/2018 |

OTHER PUBLICATIONS

Prifti et al. (ACS Chemical Biology, vol. 9, pp. 606-612 and supplement pp. 1-9; 2014) (Year: 2014).*
Dhouib et al. (Biochimica et Biophysica Acta, vol. 1811, pp. 234-241; 2011). (Year: 2011).*
Backus et al., Nature Chemical Biology, vol. 7, No. 4, pp. 228-235; 2011; (of record). (Year: 2011).*
Loving et al., Bioconjugate Chemistry, vol. 20, No. 11, pp. 2133-2141; 2009; (of record). (Year: 2009).*
Extended European Search Report for European Application No. 17835434.6, Search completed Feb. 11, 2020, dated Mar. 3, 2020, 18 pgs.
International Preliminary Report on Patentability for International Application PCT/US2017/044760, Report issued Jan. 29, 2019, dated Feb. 7, 2019, 11 Pgs.
International Search Report and Written Opinion for International Application No. PCT/US2017/044760, Search completed Nov. 14, 2017, dated Dec. 20, 2017, 18 Pgs.
"Antifungal Drug Kills Tuberculosis Bug", University of Manchester, Science Daily, Mar. 12, 2007, 3 pgs.
Backus et al., "Uptake of unnatural trehalose analogs as a reporter for Mycobacterium tuberculosis", Natural Chemical Biology, vol. 7, Apr. 2011, Online Publication: Mar. 6, 2011, pp. 228-235.

(Continued)

*Primary Examiner* — Bin Shen
(74) *Attorney, Agent, or Firm* — KPPB LLP

(57) ABSTRACT

A series of carbohydrate-dye conjugates, as well as a method for detection of pathogenic or other organisms (e.g., bacteria) using the same are provided. The carbohydrate-dye conjugate can be enzymatically incorporated into live and active (viable) bacteria of interest for facile detection of said bacteria. The conjugate incorporation is achieved by utilizing one or more of the enzymes that are endogenous to the bacteria of interest, which can incorporate the conjugate via the conjugate's carbohydrate. A detectable signal is produced by the conjugate's dye only upon incorporation into the bacteria of interest, due to the changes in the dye's local environment upon incorporation. The conjugate may be metabolically incorporated into the fatty outer membrane of a bacterial cell wall, which provides a distinctly hydrophobic environment for the conjugate's dye, causing it to produce a detectable signal.

27 Claims, 23 Drawing Sheets

(56) References Cited

OTHER PUBLICATIONS

Bloch et al., "Studies on the Virulence of Tubercle Bacilli: Variations in Virulence Effected By Tween 80 and Thiosemicarbazone", Journal of Experimental Medicine, vol. 97, No. 1, Jan. 1953, pp. 1-16.
Drusano et al., "The Combination of Rifampin plus Moxifloxacin is Synergistic for Suppression of Resistance but Antagonistic for Cell Kill of Mycobacterium tuberculosis as Determined in a Hollow-Fiber Infection Model", MBio, vol. 1, No. 3, Jul./Aug. 2010, e00139-10, 8 pgs.
Filho et al., "Sputum Smear Microscopy for Tuberculosis: Evaluation of Autofocus Functions and Automatic Identification of Tuberculosis Mycobacterium", Understanding Tuberculosis—Global Experiences and Innovative Approaches to the Diagnosis, Chapter 13, Feb. 15, 2012, pp. 277-292.
Foley et al., "Bioorthogonal Chemical Reporters for Selective In Situ Probing of Mycomembrane Components in Mycobacteria", Angewandte Chemie International Edition, Feb. 5, 2016, First Published: Jan. 6, 2016, vol. 55, No. 6, pp. 2053-2057, https://doi.org/10.1002/anie.201509216.
Goguen et al., "Development of a fluorogenic sensor for activated Cdc42", Bioorganic & Medicinal Chemistry Letters, vol. 21, No. 17, Sep. 1, 2011, pp. 5058-5061.
Grzegorzewicz et al., "Inhibition of mycolic acid transport across the Mycobacterium tuberculosis plasma membrane", Nature Chemical Biology, Feb. 19, 2012, vol. 8, pp. 334-341.
Hadjmohammadi et al., "Solvatochromism Effect of Different Solvents on UV-Vis Spectra of Flouresceine and its Derivatives", Iranian Journal of Chemistry and Chemical Engineering, vol. 27, Issue 4, 2008, pp. 9-14.
Hong et al., "Microbiome Changes during Tuberculosis and Antituberculous Therapy", Clinical Microbiology Reviews, vol. 29, No. 4, Sep. 8, 2016, pp. 915-926.
Kalscheuer et al., "Genetics of Mycobacterial Trehalose Metabolism", Microbiology Spectrum, vol. 2, No. 3, May 23, 2014, 15 pgs.
Kalscheuer et al., "Trehalose-recycling ABC transporter LpqY-SugA-SugB-SugC is essential for virulence of Mycobacterium tuberculosis", PNAS, Dec. 14, 2010, vol. 107, No. 50, pp. 21761-21766, https://doi.org/10.1073/pnas.1014642108.
Kamariza et al., "Detection of live mycobacteria with a solvatochromic trehalose probe for point-of-care tuberculosis diagnosis", bioRxiv, Aug. 2, 2017, XP055666131, 16 pgs, Retrieved from: https:jjwww.biorxiv.orgjcontent/biorxivjearly/2017/08/02/171553.full.pdf.
Kamariza et al., "Rapid Detection of Mycobacterium Tuberculosis in Sputum With a Solvatochromic Trehalose Probe", Science Translational Medicine, vol. 10, No. 430, Feb. 28, 2018, 12 pgs.
Klymchenko, "Solvatochromic and Fluorogenic Dyes as Environment-Sensitive Probes: Design and Biological Applications", Accounts of Chemical Research, 2017, vol. 50, No. 2, pp. 366-375.
Loving et al., "A Versatile Amino Acid Analogue of the Solvatochromic Fluorophore 4-N,N-Dimethylamino-1,8-naphthalimide: A Powerful Tool for the Study of Dynamic Protein Interactions", Journal of the American Chemical Society, vol. 130, No. 41, Oct. 15, 2008, pp. 13630-13638.
Loving et al., "Monitoring Protein Interactions and Dynamics with Solvatochromic Fluorophores", Trends in Biotechnology, Elsevier Publications, 2010, vol. 28, No. 2, pp. 73-83.
Loving et al., "Thiol-Reactive Derivatives of the Solvatochromic 4-N,N- Dimethylamino-1,8-naphthalimide Fluorophore: A Highly Sensitive Toolset for the Detection of Biomolecular Interactions", Bioconjugate Chemistry, vol. 20, No. 11, Oct. 12, 2009, pp. 2133-2141.
Nobre et al., "The molecular biology of mycobacterial trehalose in the quest for advanced tuberculosis therapies", Microbiology, First Published Online: Aug. 1, 2014, vol. 160, No. 8, pp. 1547-1570, doi: 10.1099/mic.0.075895-0.
Robinson et al., "What is flow cytometry (FACS analysis)?", Antibodies-online.com, Jun. 12, 2013, 15 pgs, Retrieved from: https://www.antibodies-online.com/resources/17/1247/what-is-flow-cytometry-facs-analysis/.
Rodriguez-Rivera et al., "Visualization of mycobacterial membrane dynamics in live cells", Journal of the American Chemical Society, vol. 139, No. 9, Jan. 11, 2017, pp. 3488-3495.
Rundell et al., "Deoxyfluoro-d-trehalose (FDTre) analogues as potential PET probes for imaging mycobacterial infection", Organic & Biomolecular Chemistry, vol. 14, No. 36, Sep. 28, 2016, pp. 8598-8609.
Siegrist et al., "Illumination of Growth, Division and Secretion by Metabolic Labeling of the Bacterial Cell Surface", FEMS Microbiology Reviews, Jan. 23, 2015, vol. 39, No. 2, XP055408222, pp. 184-202.
Singhal et al., "Microscopy as a diagnostic tool in pulmonary tuberculosis", International Journal of Mycobacteriology, vol. 4, No. 1, Mar. 2015, pp. 1-6.
Swarts et al., "Probing the Mycobacterial Trehalome with Bioorthogonal Chemistry", Journal of the American Chemical Society, Sep. 14, 2012, vol. 134, No. 39, pp. 16123-16126, https://doi.org/10.1021/ja3062419.
Tahlan et al., "SQ109 Targets MmpL3, a Membrane Transporter of Trehalose Monomycolate Involved in Mycolic Acid Donation to the Cell Wall Core of Mycobacterium tuberculosis", Antimicrobial Agents and Chemotherapy, Apr. 2012, vol. 56, No. 4, pp. 1797-1809, Doi: 10.1128/AAC.05708-11.
Truant et al., "Fluorescence Microscopy of Tubercle Bacilli Stained With Auramine and Rhodamine", Henry Ford Hospital Medical Bulletin, vol. 10, Jun. 1962, pp. 287-296.
Urbanek et al., "Chemoenzymatic Synthesis of Trehalose Analogues: Rapid Access to Chemical Probes for Investigating Mycobacteria", ChemBioChem, Sep. 22, 2014, First Published: Aug. 19, 2014, vol. 15, No. 14, pp. 2066-2070, https://doi.org/10.1002/cbic.201402288.
Ventura et al., "Genomics of Actinobacteria: Tracing the Evolutionary History of an Ancient Phylum", Microbiology and Molecular Biology Reviews, Sep. 2007, vol. 71, No. 3, pp. 495-548, DOI: 10.1128/MMBR.00005-07.
Wang et al., "Evaluation of a Recombinant BCG Expressing Antigen Ag85B and PPE Protein Rv3425 from DNA Segment RD11 of Mycobacterium Tuberculosis in C57BL/6 Mice", Medical Microbiology and Immunology, Springer, Berlin, May 20, 2008, vol. 198, No. 1, pp. 5-11.
Welsh et al., "Trehalose 6,6'-dimycolate—A coat to regulate tuberculosis immunopathogenesis", Tuberculosis, vol. 93, Supplement, Dec. 1, 2013, pp. S3-S9.

* cited by examiner

METHODS FOR DETECTING MYCOBACTERIA WITH SOLVATOCHROMIC DYE CONJUGATES

CROSS-REFERENCE TO RELATED APPLICATIONS

This application is a national stage of PCT Patent Application No. PCT/US2017/044760, entitled "Methods for Detecting Mycobacteria with Solvatochromic Dye Conjugates" to Bertozzi et al., filed Jul. 31, 2017, which claims priority to U.S. Provisional Patent Application No. 62/368928, filed Jul. 29, 2016, the disclosures of which are incorporated by reference herein in their entirety.

STATEMENT REGARDING FEDERALLY SPONSORED RESEARCH

This invention was made with Government support under contract AI051622 awarded by the National Institutes of Health. The Government has certain rights in the invention.

FIELD OF THE INVENTION

The current disclosure is directed to carbohydrate-dye conjugates and methods for detection of pathogenic or other organisms using the same.

BACKGROUND OF THE INVENTION

Mycobacteria, which belong to *Mycobacterium* genus of Actinobacteria phylum, are a significant cause of morbidity and mortality, particularly among immunocompromised or elderly individuals and in countries with limited medical resources. Ninety-five percent of human infections are caused by seven species: *Mycobacterium tuberculosis, M. avium* (also known as the *mycobacterium avium* complex or *M. avium-intracellulare*), *M. leprae, M. kansasii, M. fortuitum, M. chelonae*, and *M. absecessus*. One feature of all *Mycobacterium* species distinguishing them from canonical gram-negative and gram-positive bacteria is a very thick, waxy, and rich in mycolic acids/mycolates cell wall, also called mycomembrane, which makes a substantial contribution to the hardiness of this genus. In fact, the lipid content of the mycobacterial envelope can reach as high as 60% of the dry weight of the bacteria, contributing to the envelope's low permeability and these bacteria's resistance to common antibiotics and chemotherapeutic agents.

In particular, tuberculosis (TB), caused by *Mycobacterium tuberculosis* (Mtb), is the leading cause of death from an infectious bacterial disease and, therefore, is a serious global health challenge, with an estimated 1.8 million deaths in 2015. Furthermore, the increasing number of Mtb strains resistant to courses of treatment have exacerbated the global epidemic. Despite significant effort in the development of TB diagnostics over the last decade, TB control programs in many countries with endemic TB still rely on the detection of tubercle bacilli through sputum smear or culture. More specifically, the currently standard approach for rapid TB diagnosis in high burden areas is detection of Mtb in patient sputum or extra-pulmonary sites using the color-based Ziehl-Neelsen (ZN) test, developed more than 100 years ago (F. Ziehl, Zur Farbung des Tuberkelbacillus, *Dtsch. Med. Wschr.* 8, 451 (1882); F. Ziehl, Ueber die Farbung des Tuberkelbacillus, *Dtsch. Med. Wschr.* 9, 247-249 (1883); F. Neelsen, Ein Casuistischer Beitrag zur Lehre von der Tuberkulose, *Centralbl. Med. Wissensch.* 28, 497-501 (1883); the disclosures of which are incorporated herein by reference), or the fluorescent auramine-based Truant stain, first reported in 1938 (P. K. H. Hagemann. Fluoreszenzfärbung von Tuberkelbakterien mit Auramin, *Münch. Med. Wschr.* 85, 1066-1068 (1938), the disclosure of which is incorporated herein by reference). Both of these tests rely on the propensity of the mycobacterial hydrophobic outer membrane to bind and retain similarly hydrophobic dyes (J. C. Boyd, J. J. Marr, Decreasing reliability of acid-fast smear techniques for detection of tuberculosis, *Ann. Intern. Med.* 82, 489-492 (1975); J. P. Truant, W. A. Brett, W. Thomas, Jr., Fluorescence microscopy of tubercle bacilli stained with auramine and rhodamine, *Henry Ford Hosp. Med. Bull.* 10, 287 (1962); the disclosure of which are incorporated herein by reference). However, both protocols also require extensive processing to remove excess dye from debris and other bacteria, while maintaining dye retention within mycobacteria of interest. Consequently, these tests have poor specificity and low sensitivity. Their sensitivity, in particular, varies widely from 32% to 94%, depending on the method used and, most disconcertingly, the experience of the user (C. F. F. C. Filho, M. G. F Costa, "[Sputum smear microscopy for tuberculosis: evaluation of autofocus functions and automatic identification of tuberculosis *mycobacterium*]" in *Understanding Tuberculosis—Global Experiences and Innovative Approaches to the Diagnosis*, P. J. Cardona, Ed. (InTech: Intechopen.com, 2012), chapt. 13. DOI: 10.5772/30953; R. Singhal, V. P. Myneedu, Microscopy as a diagnostic tool in pulmonary tuberculosis, *Int. J. Mycobacteriol.* 4, 1-6 (2015); the disclosure of which are incorporated herein by reference). Therefore, new tools to advance diagnostic accuracy, simplicity, reliability, and specificity for live mycobacteria in any sample of interest are urgently needed.

SUMMARY OF THE INVENTION

Embodiments are directed to methods for detecting metabolically active bacteria of interest in a sample, the method including:
   contacting the sample with a carbohydrate-solvatochromic dye conjugate that includes:
      a carbohydrate moiety configured to facilitate the selective metabolic uptake of the carbohydrate-solvatochromic dye conjugate into an outer cell membrane exclusively of the bacteria of interest, and
      a solvatochromic dye linked to the carbohydrate moiety, the solvatochromic dye configured to report the incorporation of the carbohydrate-solvatochromic dye conjugate into the outer cell membrane of the sample's bacteria of interest; and
   detecting a spectroscopic signal from the solvatochromic dye moiety of the carbohydrate-solvatochromic dye conjugate, wherein the spectroscopic signal indicates the presence of the metabolically active bacteria of interest in the sample.

In other embodiments the bacteria of interest is characterized by hydrophobic outer cell membrane.

In still other embodiments the outer cell membrane of the bacteria of interest is a mycomembrane rich in hydrophobic mycolates. In some such embodiments the mycomembrane mycolates include trehalose mycolates.

In yet other embodiments the bacteria of interest is capable of metabolic uptake of trehalose.

In still yet other embodiments the bacteria of interest metabolically uptakes trehalose with high specificity.

In still yet other embodiments the bacteria of interest possess acyl transferase antigen 85 (Ag85) protein complex capable of trehalose mycolylation, thereby promoting the uptake of trehalose by the bacteria of interest.

In still yet other embodiments the bacteria of interest belong to Actinobacteria phylum. In some such embodiments the bacteria of interest are mycobacteria or corynebacteria.

In still yet other embodiments the carbohydrate moiety of the conjugate is trehalose.

In still yet other embodiments the carbohydrate moiety of the conjugate is a trehalose analog.

In still yet other embodiments the carbohydrate-solvatochromic dye conjugate has formula:

wherein one and only one of Z1-Z7 is a linked solvatochromic dye and the rest of Z1-Z7 are OH.

In still yet other embodiments the carbohydrate-solvatochromic dye conjugate has formula:

wherein one and only one of Z1-Z4 is a linked solvatochromic dye and the rest of Z1-Z4 are OH.

In still yet other embodiments Z1 is the linked solvatochromic dye.

In still yet other embodiments the linked solvatochromic dye is selected from 4-DMAP, 4-DMN, 6-DMN, Nile Red, 3-HC, 3-MC, PRODAN, Anthradan, NBD and derivatives thereof.

In still yet other embodiments the sample is a biological sample. In some such embodiments the biological sample is selected from the group of: sputum, blood, serum, plasma, urine, bronchoalveolar lavage fluid, buccal swab (e.g., cheek swab), or tissue samples.

In still yet other embodiments the sample is an environmental sample. In some such embodiments the sample is taken from an environment selected from the group of: air, water, or inanimate surface. In other such embodiments the biological sample is a sample from a subject suspected of having, or at risk of infection with the bacteria of interest. In still other such embodiments the biological sample is a sample from a subject suspected of having, or at risk of infection with *Mycobacterium tuberculosis*. In yet other such embodiments the environmental sample is a sample known or suspected to have contact with subject or subjects suspected of having, or at risk of infection with the bacteria of interest. In still yet other such embodiments the environmental sample is a sample known or suspected to have contact with subject or subjects suspected of having, or at risk of infection with *Mycobacterium tuberculosis.*

In still yet other embodiments the bacteria of interest is one or more selected from the group of: *M. tuberculosis, M. avium* (or *M. avium-intracellulare*), *M. leprae* (particularly *M. leprae* infection leading to tuberculoid leprosy), *M. kansasii, M. fortuitum, M. chelonae, M. absecessus, M. marinum, M. Nocardia, M. xenopi, M. simiae, M. szulgai, M. scrofulaceum, M. malmoense, M. terrae-nonchromogenicum* complex, *M. haemophilum, M. genavense, M. celatum, M. interjectum, M. confluentis, M. triplex, M. lentiflavum, M. branderi, M. conspicuum, M. cookii, M. asiaticum, M. marinum M. gordonae, M. fortuitum, M. chelonae-abscessu*, and *M. mucogenicum.*

In still yet other embodiments the metabolically active bacteria of interest is selected from the group of: *Mycobacterium tuberculosis, Mycobacterium leprae*, or *Corynebacterium diphtheriae.*

In still yet other embodiments the bacteria of interest is present extracellularly.

In still yet other embodiments the bacterial of interest is present inside a eukaryotic cell.

Other embodiments are directed to a carbohydrate-solvatochromic dye conjugate of formula:

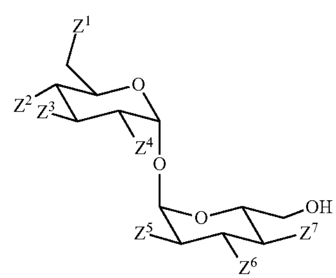

wherein one and only one of Z1-Z7 is a linked solvatochromic dye and the rest of Z1-Z7 are OH.

In other embodiments the carbohydrate-solvatochromic dye conjugate has formula:

wherein one and only one of Z1-Z4 is a linked solvatochromic dye and the rest of Z1-Z4 are OH.

In still other embodiments the linked solvatochromic dye is of one of the formulas selected from the group of:

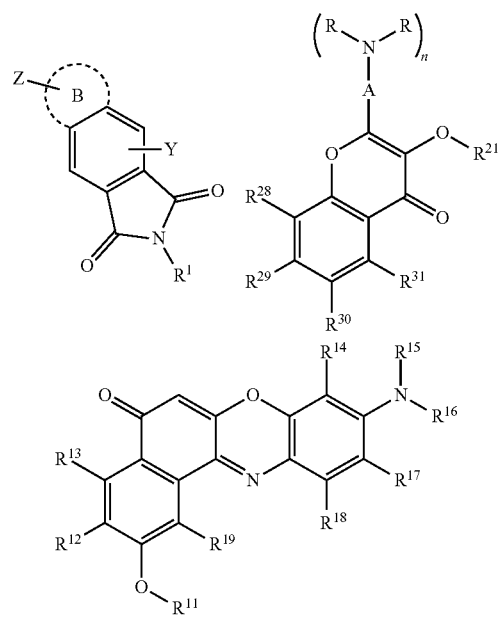
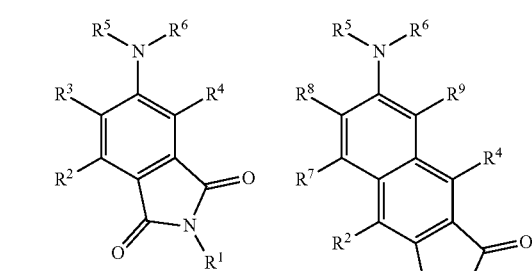
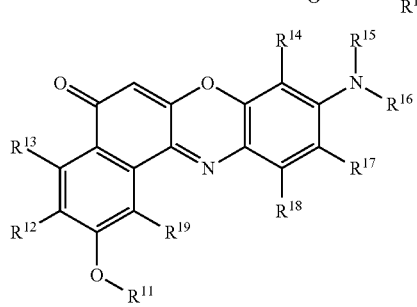
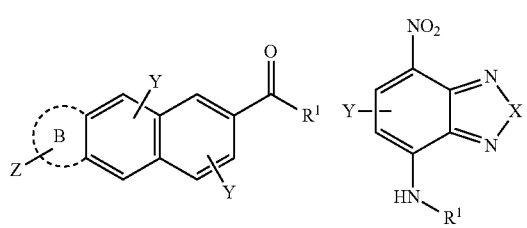
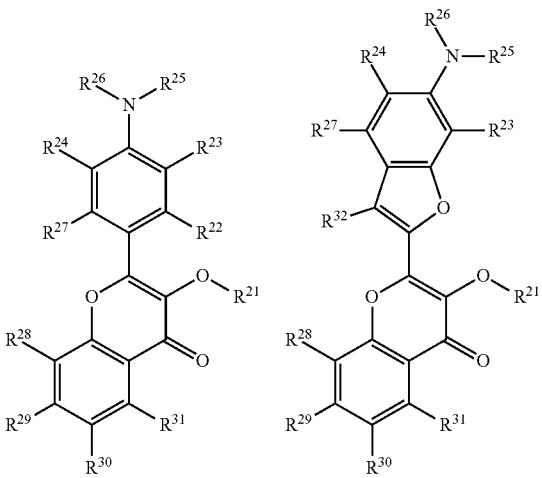
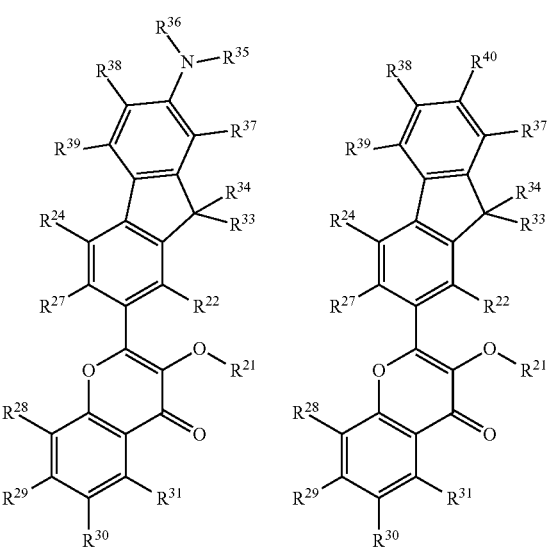

wherein:

B is an optional fused 5 or 6-membered aryl or heteroaryl ring, optionally further substituted with one or more Z substituents independently selected from H, alkyl, substituted alkyl, halogen, hydroxyl, amino, substituted amino, cyano, nitro;

Y is one or more substituents independently selected from H, alkyl, substituted alkyl, halogen, hydroxyl, amino, substituted amino, cyano, nitro, alkoxy and substituted alkoxy, wherein at least one Y or Z is —NR2;

A is an aryl or heteroaryl system comprising one, two or three 5- or 6-membered rings, optionally further substituted with one or more Z substituents independently selected from H, alkyl, substituted alkyl, halogen, hydroxyl, amino, substituted amino, cyano and nitro;

n is 0 or 1;

X is O, S or NR1;

each R, R1, R11, R15, R16 and R21 is independently selected from H, alkyl and substituted alkyl; and R12-R14, R17-R19 and R28-R31 are each independently selected from H, alkyl, substituted alkyl, halogen, hydroxyl, amino, substituted amino, cyano, nitro, alkoxy and substituted alkoxy;

wherein at least one of Z, Y and R1-R31 is linked to the sugar of the conjugate via an optional linker.

In yet other embodiments the linked solvatochromic dye is of one of formulas selected from the group of:

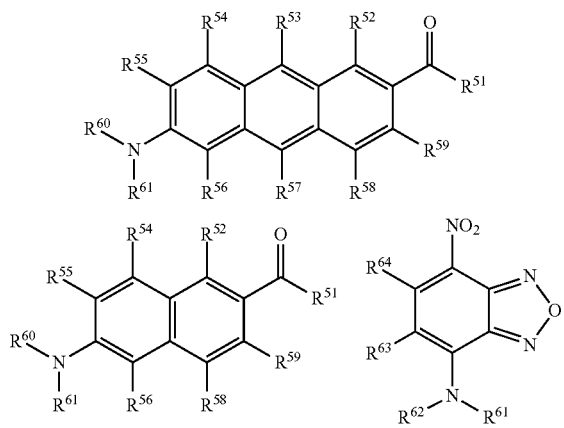

wherein

R1, R5, R6, R11, R15, R16, R21, R25, R26, R33-R35, R36, R51, R60 and R61 are independently selected from H, alkyl and substituted alkyl; and R2-R4, R7-R9, R12-R14, R17-R19, R22-R24, R27-R32, R37-R40 and R52-R59 are each independently selected from H, alkyl, substituted alkyl, alkoxy, substituted alkoxy, halogen, hydroxyl, amino, substituted amino, cyano and nitro;

wherein at least one of R1-R39 is linked to the sugar of the conjugate via an optional linker.

In still yet other embodiments the solvatochromic dye is selected from the group of:

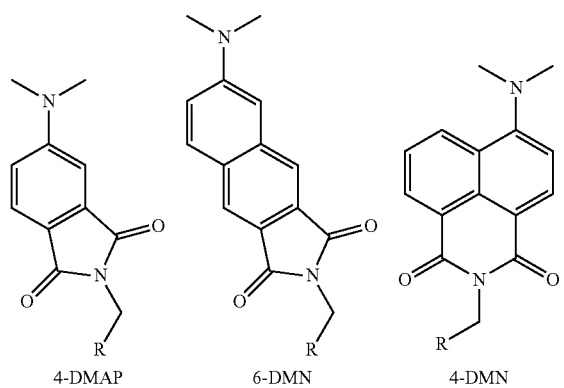

4-DMAP    6-DMN    4-DMN

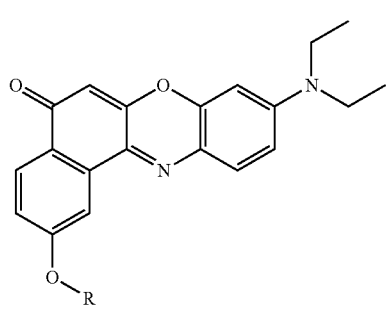

Nile Red

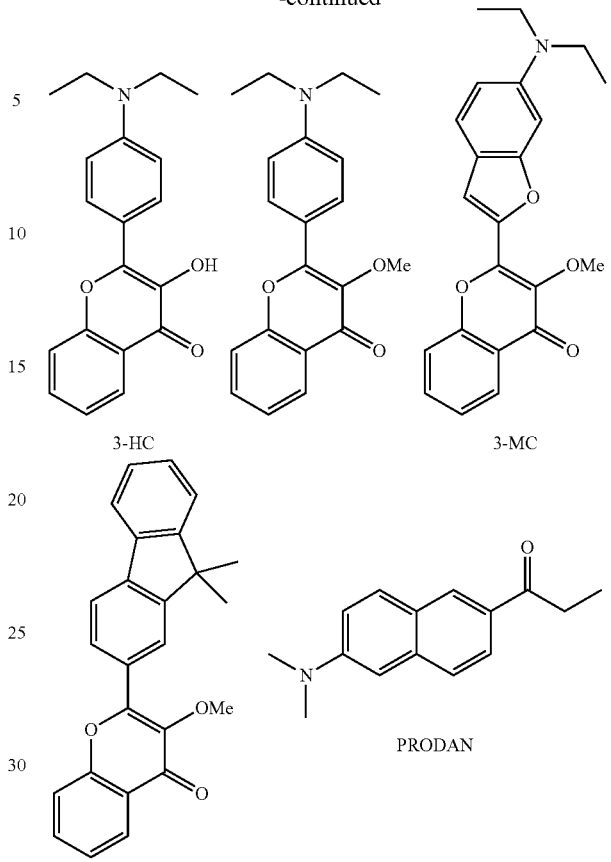

3-HC    3-MC

PRODAN

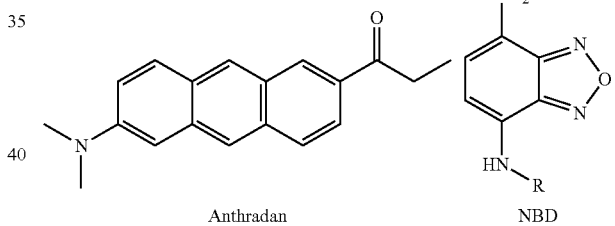

Anthradan    NBD or an analog thereof, wherein the solvatochromic dye is linked to the sugar at any available position.

Still other embodiments are directed to metabolically labeled bacterial cell including:

an outer cell wall comprising mycolates; and at least on carbohydrate-solvatochromic dye conjugate covalently attached to a mycolic acid lipid of the outer cell membrane.

Yet other embodiments are directed to a kit, including:

a carbohydrate-solvatochromic dye conjugate of any of claims 28-32; and one or more components selected from an enzyme, a chemical cleavage agent, a buffer, a cell, a metabolically tagged cell, a microscope, a positive control, a negative control, and instructions for metabolically labeling a target cell.

In other such embodiments the solvatochromic dye is fluorogenic.

Yet other embodiments are directed to a method for monitoring a treatment of a bacterial infection in a subject, the method including:

obtaining a series of samples at predetermined intervals or treatment plan steps from a subject suffering from a bacterial infection;

contacting each of the samples with a carbohydrate-solvatochromic dye conjugate including:
a carbohydrate moiety configured to facilitate the selective metabolic uptake of the carbohydrate-solvatochromic dye conjugate into an outer cell membrane exclusively of the bacteria of interest, and
a solvatochromic dye moiety linked to the carbohydrate moiety, the solvatochromic dye moiety configured to report the incorporation of the carbohydrate-solvatochromic dye conjugate into the outer cell membrane of the sample's bacteria of interest; and
for each sample, detecting a spectroscopic signal from the solvatochromic dye moiety of the carbohydrate-solvatochromic dye conjugate, wherein the spectroscopic signal indicates the presence of the metabolically active bacteria of interest in the sample; and
adjusting the treatment plan according to the spectroscopically measured presence or absence of the metabolically active bacteria of interest in the series of samples.

In other embodiments the solvatochromic dye is fluorogenic and the detection is a fluorescence measurement.

In still other embodiments the sample incubation with the carbohydrate-solvatochromic dye conjugate and spectroscopic detection of the metabolically active bacteria of interest is followed by a flow cytometry analysis for quantification of the bacteria of interest in the sample.

In yet other embodiments the bacteria of interest belong to the Actinobacteria phylum.

In still yet other embodiments the bacteria of interest are mycobacteria or corynebacteria.

In still yet other embodiments the bacteria of interest is one or more from bacteria selected from the group of: *M. tuberculosis*, *M. avium* (or *M. avium-intracellulare*), *M. leprae* (particularly *M. leprae* infection leading to tuberculoid leprosy), *M. kansasii*, *M. fortuitum*, *M. chelonae*, *M. absecessus*, *M. marinum*, *M. Nocardia*, *M. xenopi*, *M. simiae*, *M. szulgai*, *M. scrofulaceum*, *M. malmoense*, *M. terrae-nonchromogenicum* complex, *M. haemophilum*, *M. genavense*, *M. celatum*, *M. interjectum*, *M. confluentis*, *M. triplex*, *M. lentiflavum*, *M. branderi*, *M. conspicuum*, *M. cookii*, *M. asiaticum*, *M. marinum M. gordonae*, *M. fortuitum*, *M. chelonae-abscessu*, and *M. mucogenicum*.

In still yet other embodiments the bacteria of interest is selected from the group of: *Mycobacterium tuberculosis*, *Mycobacterium leprae*, or *Corynebacterium diphtheriae*.

In still yet other embodiments the carbohydrate-dye conjugate has formula:

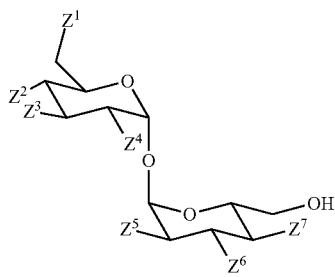

wherein one and only one of Z1-Z7 is a linked solvatochromic dye and the rest of Z1-Z7 are OH.

In still yet other embodiments the sample is selected from the group of: sputum, blood, serum, plasma, urine, bronchoalveolar lavage fluid, and buccal swab.

In still yet other embodiments obtaining the sample is performed before treatment and at one or more time points during treatment or after treatment.

In still yet other embodiments the method further includes adjusting the anti-infective treatment dosage or regimen according to a change in the amount of the metabolically active bacteria of interest in the sample over time.

In still yet other embodiments the anti-infective treatment dosage or regimen comprises an anti-mycotic agent.

In still yet other embodiments obtaining the sample is performed at a first time point and at a second time point following start of the treatment, wherein the second time point is from about 1 week to about 1 year after the first time point.

Still yet other embodiments are directed to methods for determining bacteria drug or treatment plan sensitivity including:
obtaining a bacterial sample of interest;
splitting the bacterial sample of interest into a multitude of samples according to the number of available drug cocktails or treatment plans;
treating each sample with appropriate drug cocktail or treatment plan as assigned;
contacting each of the sample with a carbohydrate-solvatochromic dye conjugate that includes:
a carbohydrate moiety configured to facilitate the selective metabolic uptake of the carbohydrate-solvatochromic dye conjugate into an outer cell membrane exclusively of the bacteria of interest, and
a solvatochromic dye linked to the carbohydrate moiety, the solvatochromic dye configured to report the incorporation of the carbohydrate-solvatochromic dye conjugate into the outer cell membrane of the sample's bacteria of interest; and
for each treated sample, detecting a spectroscopic signal from the solvatochromic dye moiety of the carbohydrate-solvatochromic dye conjugate, wherein the spectroscopic signal indicates the persistence of the metabolically active bacteria of interest in the sample and its resistance to the drug cocktail or treatment plan used on that sample.

In other embodiments the bacteria of interest belong to Actinobacteria phylum.

In still other embodiments the bacteria of interest are mycobacteria or corynebacteria.

In yet other embodiments the bacteria of interest is one or more selected from the group of: *M. tuberculosis*, *M. avium* (or *M. avium-intracellulare*), *M. leprae* (particularly *M. leprae* infection leading to tuberculoid leprosy), *M. kansasii*, *M. fortuitum*, *M. chelonae*, *M. absecessus*, *M. marinum*, *M. Nocardia*, *M. xenopi*, *M. simiae*, *M. szulgai*, *M. scrofulaceum*, *M. malmoense*, *M. terrae-nonchromogenicum* complex, *M. haemophilum*, *M. genavense*, *M. celatum*, *M. interjectum*, *M. confluentis*, *M. triplex*, *M. lentiflavum*, *M. branderi*, *M. conspicuum*, *M. cookii*, *M. asiaticum*, *M. marinum M. gordonae*, *M. fortuitum*, *M. chelonae-abscessu*, and *M. mucogenicum*.

In still yet other embodiments the bacteria of interest is selected from the group of: *Mycobacterium tuberculosis*, *Mycobacterium leprae*, or *Corynebacterium diphtheriae*.

In still yet other embodiments the carbohydrate-solvatochromic dye conjugate has formula:

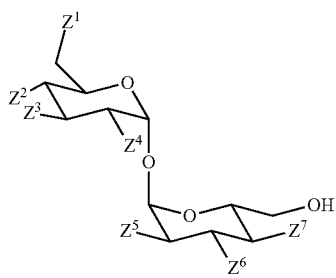

wherein one and only one of Z1-Z7 is a linked solvatochromic dye and the rest of Z1-Z7 are OH.

In still yet other embodiments the sample is selected from the group of: sputum, blood, serum, plasma, urine, bronchoalveolar lavage fluid, and buccal swab Additional embodiments and features are set forth in part in the description that follows, and in part will become apparent to those skilled in the art upon examination of the specification or may be learned by the practice of the disclosed subject matter. A further understanding of the nature and advantages of the present disclosure may be realized by reference to the remaining portions of the specification and the drawings, which forms a part of this disclosure.

BRIEF DESCRIPTION OF THE DRAWINGS

These and other features and advantages of the present invention will be better understood by reference to the following detailed description when considered in conjunction with the accompanying data and figures, wherein.

DETAILED DISCLOSURE

The embodiments of the invention described herein are not intended to be exhaustive or to limit the invention to precise forms disclosed. Rather, the embodiments selected for description have been chosen to enable one skilled in the art to practice the invention.

Turning now to the figures and schemes, a series of carbohydrate-dye conjugates is described, as well as a method for detection of pathogenic or other organisms (e.g., bacteria) using the same. In many embodiments, a carbohydrate-dye conjugate is selected such that it can be enzymatically incorporated into live and active (viable) bacteria of interest for facile detection of said bacteria. In many embodiments, the conjugate incorporation is achieved by utilizing one or more of the enzymes that are endogenous to the bacteria of interest, which can incorporate the conjugate via the conjugate's carbohydrate. In many embodiments, a detectable signal is produced by the conjugate's dye only upon incorporation into the bacteria of interest, due to the changes in the dye's local environment upon incorporation. In many embodiments, the conjugate is metabolically incorporated into the fatty outer membrane of a bacterial cell wall, which provides a distinctly hydrophobic environment for the conjugate's dye, causing it to produce a detectable signal. To this end, in many embodiments, the conjugate's carbohydrate is chosen to facilitate the conjugate's metabolic uptake and incorporation into the cell wall of viable bacteria of interest, while conjugate's dye is chosen to efficiently and reliably report such successful incorporation events. In many embodiments, the bacteria of interest are actinobacteria, and, more specifically, mycobacteria, characterized by exceptionally hydrophobic outer cell membrane—mycomembrane.

Figure 1:
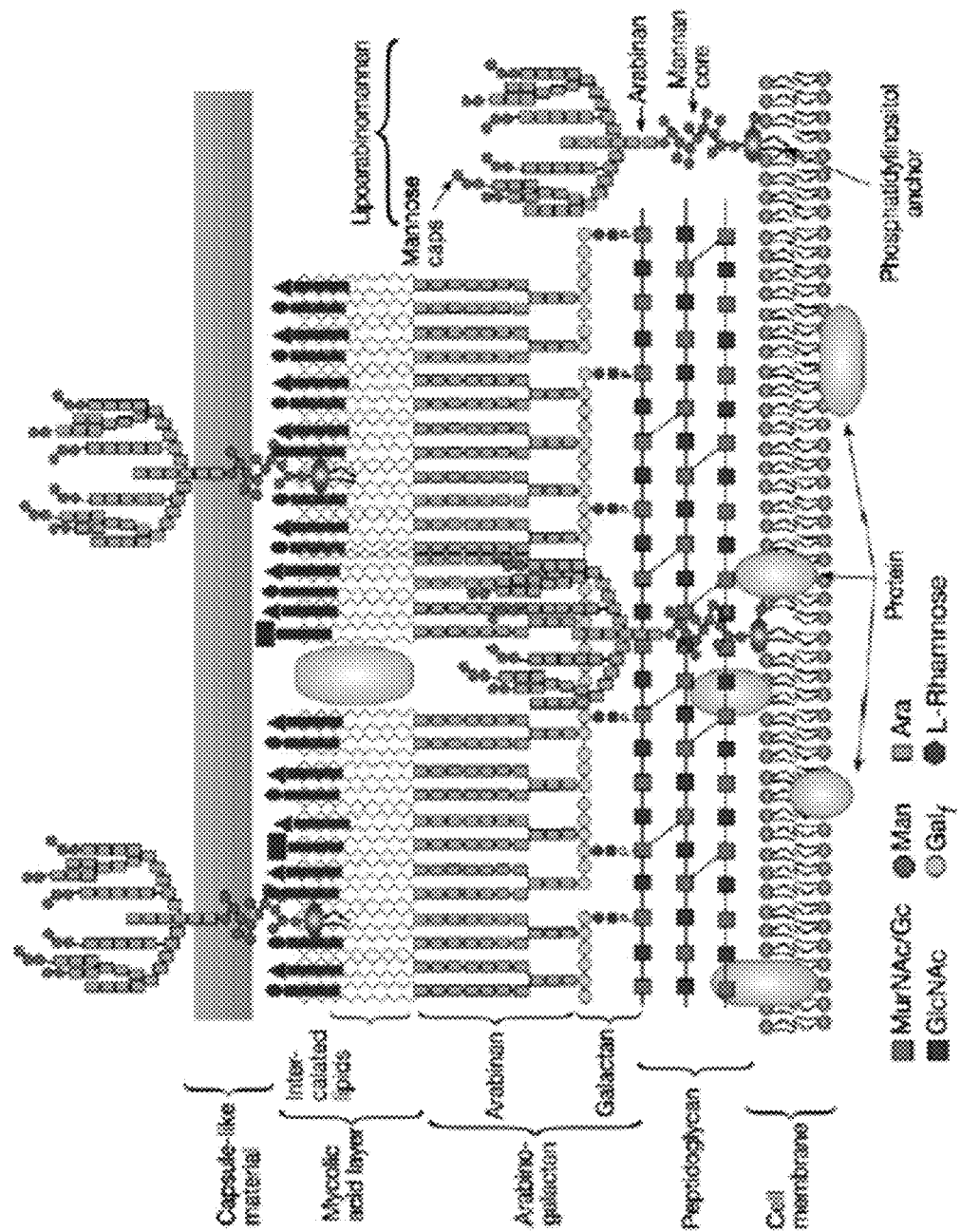
FIG. 1 provides a schematic of the structure and components of a mycobacterial cell wall (including the mycomembrane) in accordance with prior art.

Glycolipids featuring long fatty mycolic acids are known to be an abundant and essential component of bacterial mycomembranes (FIG. 1). The distinctive feature of these molecules is presence of long chain ($C_{30}$ to $C_{90}$) cyclopropanated lipids, which are largely responsible for mycomembrane extreme hydrophobicity, and, as a result, mycobacteria's virulence and persistence within a host. Specifically, trehalose sugar-based mycolates (FIG. 2), most prominently trehalose monomycolates (TMM) and dimycolates (TDM), are known to be essential for Mtb cell viability (H. Bloch, Studies on the virulence of tubercle bacilli, *J. Exp. Med.* 97, 1-16 (1953); K. J. Welsh, R. L. Hunter, J. K. Actor, Trehalose 6,6'-dimycolate—a coat to regulate tuberculosis immunopathogenesis. *Tuberculosis*. 93, S3-S9 (2013); the disclosures of which are incorporated herein). These molecules are incorporated into the mycobacterial cell wall by action of extracellular enzymes, such as acyl transferase Ag85 protein complex (consisting of antigens 85A, 85B and 85C protein homologs), which catalyze the esterification of trehalose with mycolic acids (FIG. 1).

Figure 3A:
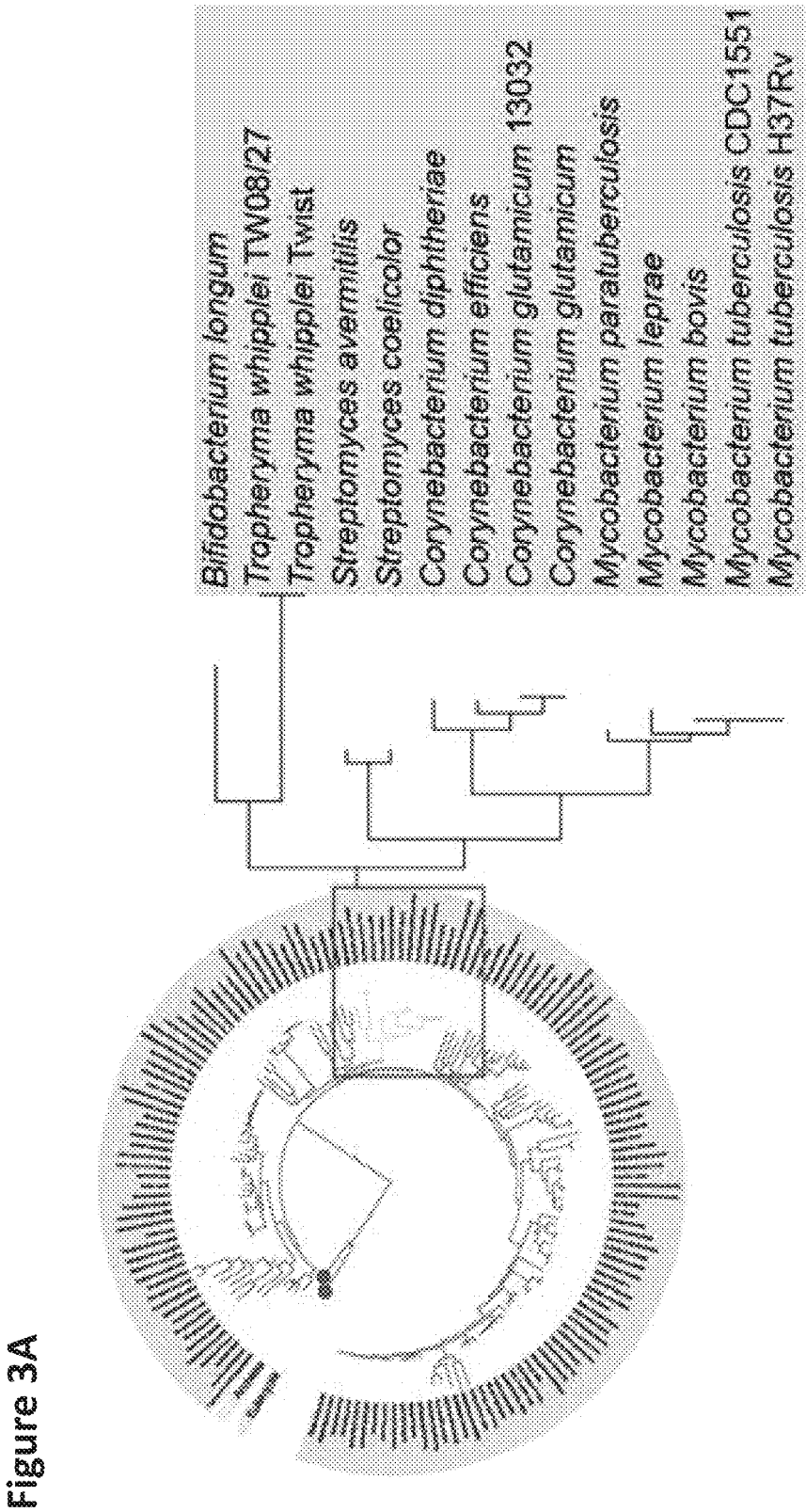
FIGS. 3A and B identify bacterial species in the actinobacteria phylum that possess Ag85 protein homologs (in green) necessary for metabolic incorporation of trehalose analogs into the mycomembrane, in accordance with embodiments of the application.
Figure 3B:
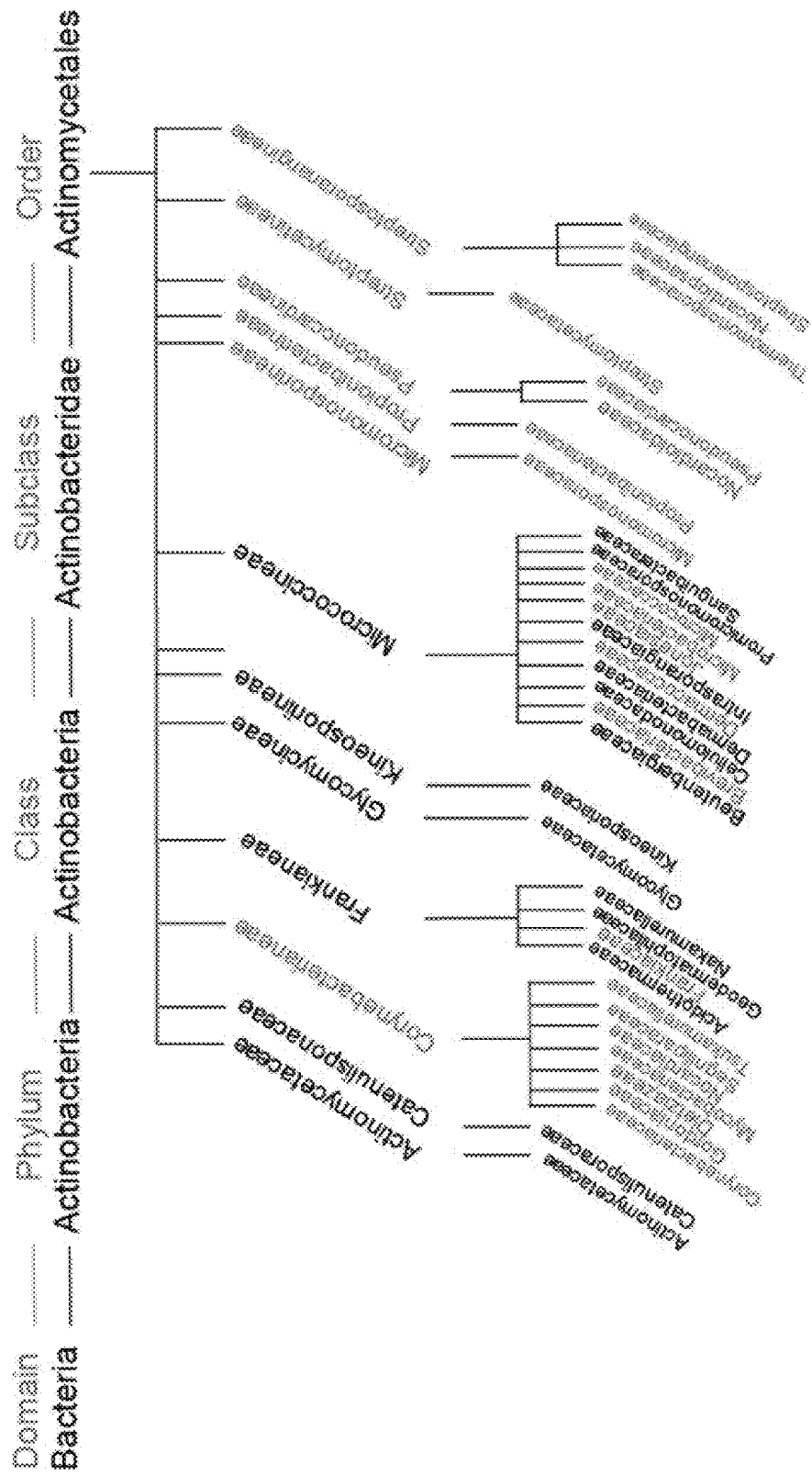

Furthermore, trehalose mycolates are thought to be unique to the Actinobacteria phylum, which includes pathogenic mycobacteria and corynebacteria, but not canonical gram-positive or gram-negative organisms, nor human hosts. In support of this notion, it has been shown that Ag85A-C protein homologs, the enzymes known to be responsible for mycolylation of trehalose, are largely restricted to the Actinomycetales order of bacteria. To this end, FIGS. 3A, 3B, as well as Table 1 below, list bacterial organisms and bacterial strains found to have Ag85 homology necessary for trehalose mycolylation and, therefore, able to efficiently and reliably uptake trehalose conjugates. By contrast, the most abundant constituents of the lung microbiome, such members of the Proteobacteria, Firmicutes and Bacteroidetes phyla and the *Pseudomonas, Streptococcus, Prevotella, Fusobacteria* and *Veillonella* genera (J. M. Beck, B. Young, G. B. Huffnagle, The microbiome of the lung, *Transl. Res.* 160, 258-266 (2012); B. Y. Hong, N. P. Maulen, A. J. Adami, H. Granados, M. E. Balcells, J. Cervantes, Microbiome changes during tuberculosis and antituberculous therapy, *Clin. Microbiol. Rev.* 29, 915-926 (2016); the disclosures of which is incorporated herein by reference), do not possess identifiable Ag85 homologs and, therefore, are not expected to uptake trehalose into their cell walls. Therefore, in many embodiments of this invention, the specificity of Mtb and other actinobacteria detection utilizes trehalose mycolates as detection agents.

TABLE 1

| [Brevibacterium] flavum |
|---|
| Actinoalloteichus hymeniacidonis |
| Actinoalloteichus sp. |
| Actinoplanes friuliensis |
| Actinoplanes sp. |
| Actinosynnema mirum |
| Alloactinosynnema sp. |
| Amycolatopsis japonica |
| Amycolatopsis lurida |
| Amycolatopsis mediterranei |
| Amycolatopsis orientalis |
| Amycolicicoccus subflavus |
| Arthrobacter sp. |
| Brachybacterium faecium |
| Brachybacterium sp. |

TABLE 1-continued

| [Brevibacterium] flavum |
|---|
| Brevibacterium linens |
| Corynebacteriales bacterium |
| Corynebacterium ammoniagenes |
| Corynebacterium aquilae |
| Corynebacterium argentoratense |
| Corynebacterium atypicum |
| Corynebacterium aurimucosum |
| Corynebacterium callunae |
| Corynebacterium camporealensis |
| Corynebacterium casei |
| Corynebacterium deserti |
| Corynebacterium diphtheriae |
| Corynebacterium doosanense |
| Corynebacterium efficiens |
| Corynebacterium epidermidicanis |
| Corynebacterium falsenii |
| Corynebacterium flavescens |
| Corynebacterium frankenforstense |
| Corynebacterium glutamicum |
| Corynebacterium glyciniphilum |
| Corynebacterium halotolerans |
| Corynebacterium humireducens |
| Corynebacterium imitans |
| Corynebacterium jeikeium |
| Corynebacterium kroppenstedtii |
| Corynebacterium kutscheri |
| Corynebacterium lactis |
| Corynebacterium marinum |
| Corynebacterium maris |
| Corynebacterium mustelae |
| Corynebacterium phocae |
| Corynebacterium pseudotuberculosis |
| Corynebacterium resistens |
| Corynebacterium simulans |
| Corynebacterium singulare |
| Corynebacterium sp. |
| Corynebacterium sphenisci |
| Corynebacterium stationis |
| Corynebacterium terpenotabidum |
| Corynebacterium testudinoris |
| Corynebacterium ulcerans |
| Corynebacterium urealyticum |
| Corynebacterium ureicelerivorans |
| Corynebacterium uterequi |
| Corynebacterium variabile |
| Corynebacterium vitaeruminis |
| Curtobacterium sp. |
| Cutibacterium avidum |
| Dermabacter vaginalis |
| Dietzia timorensis |
| Frankia alni |
| Frankia sp. |
| Gordonia bronchialis |
| Gordonia polyisoprenivorans |
| Gordonia sp. |
| Gordonia terraee |
| Jonesia denitrificans |
| Kibdelosporangium phytohabitans |
| Kocuria rhizophila |
| Kutzneria albida |
| Luteipulveratus mongoliensis |
| Micromonospora sp. |
| Mycobacterium abscessus |
| Mycobacterium africanum |
| Mycobacterium avium |
| Mycobacterium bovis |
| Mycobacterium canetti |
| Mycobacterium chelonae |
| Mycobacterium chimaera |
| Mycobacterium chubuense |
| Mycobacterium fortuitum |
| Mycobacterium gilvum |
| Mycobacterium goodii |
| Mycobacterium haemophilum |
| Mycobacterium immunogenum |
| Mycobacterium indicus pranii |
| Mycobacterium intracellulare |
| Mycobacterium kansasii |

TABLE 1-continued

[*Brevibacterium*] *flavum*

*Mycobacterium leprae*
*Mycobacterium liflandii*
*Mycobacterium marinum*
*Mycobacterium massiliense*
*Mycobacterium microti*
*Mycobacterium neoaurum*
*Mycobacterium phlei*
*Mycobacterium rhodesiae*
*Mycobacterium sinense*
*Mycobacterium smegmatis*
*Mycobacterium sp.*
*Mycobacterium tuberculosis*
*Mycobacterium ulcerans*
*Mycobacterium vaccae*
*Mycobacterium vanbaalenii*
*Nocardia brasiliensis*
*Nocardia cyriacigeorgica*
*Nocardia farcinica*
*Nocardia nova*
*Nocardia seriolae*
*Nocardia soli*
*Nocardiopsis alba*
*Propionibacterium avidum*
*Pseudonocardia*
*Rhodococcus aetherivorans*
*Rhodococcus equi*
*Rhodococcus erythropolis*
*Rhodococcus fascians*
*Rhodococcus jostii*
*Rhodococcus opacus*
*Rhodococcus pyridinivorans*
*Rhodococcus sp.*
*Saccharomonospora viridis*
*Saccharopolyspora erythraea*
*Salinispora arenicola*
*Segniliparus rotundus*
*Streptomyces albus*
*Streptomyces ambofaciens*
*Streptomyces ambofaciens*
*Streptomyces bingchenggensis*
*Streptomyces cattleya*
*Streptomyces coelicolor*
*Streptomyces globisporus*
*Streptomyces lincolnensis*
*Streptomyces lividans*
*Streptomyces lydicus*
*Streptomyces pactum*
*Streptomyces parvulus*
*Streptomyces pratensis*
*Streptomyces reticuli*
*Streptomyces sampsonii*
*Streptomyces scabiei*
*Streptomyces silaceus*
*Streptomyces sp.*
*Streptomyces venezuelae*
*Streptomyces violaceusniger*
*Streptosporangium roseum*
*Thermomonospora curvata*
*Tsukamurella paurometabola*
*Verrucosispora maris*

Figure 4:
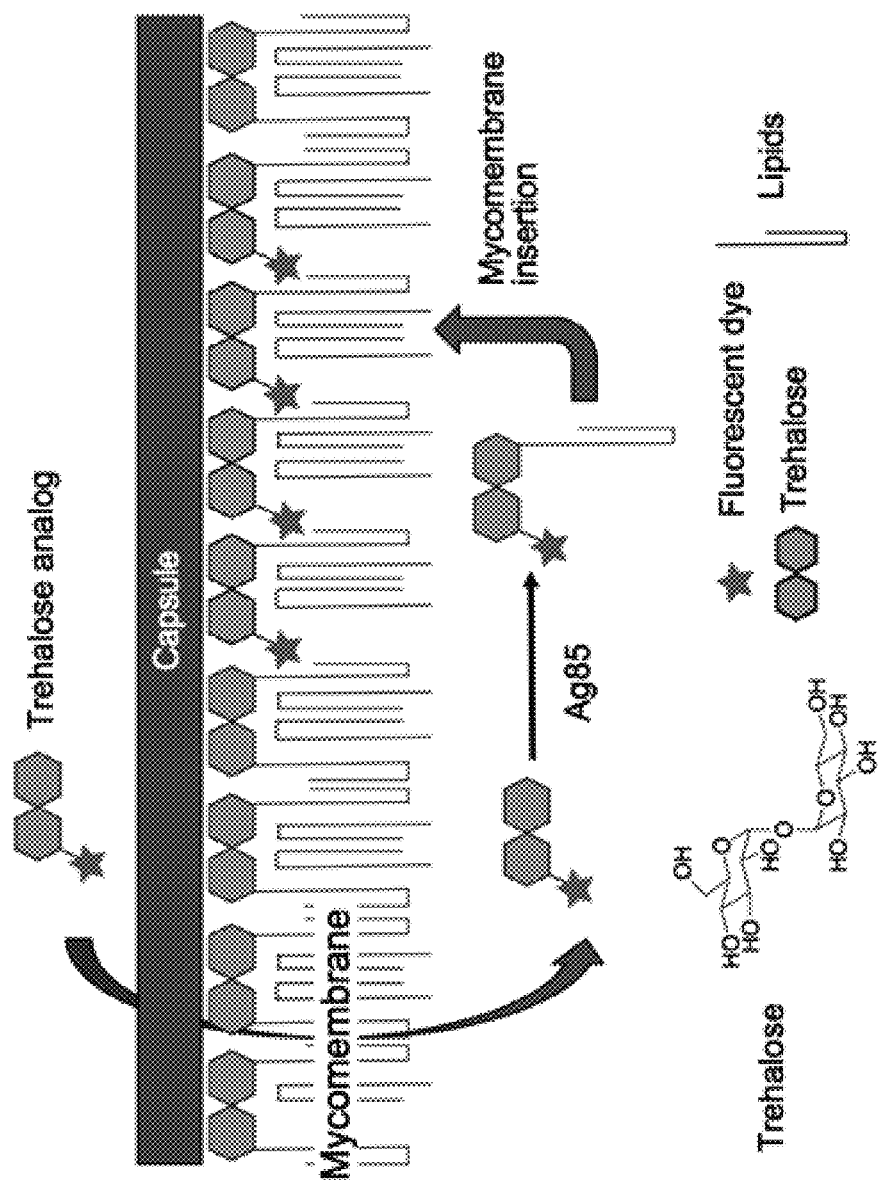
FIG. 4 provides a schematic of the Ag85 enzyme driven incorporation of trehalose-dye conjugate into mycomembrane in accordance with prior art.

Moreover, it has been shown that modifying trehalose sugar with various functionalities, such as fluorine, azide, and alkyne, as well as larger fluorophore-functionalized derivatives, does not prevent its metabolic incorporation into the mycobacterial outer membrane as trehalose mycolates (FIG. 4). (K. Backus, H. I. Boshoff, C. S. Barry, O. Boutureira, M. K. Patel, S. S. Lee, K. Tahlan, C. E. Barry 3$^{rd}$, B. G. Davis, Uptake of unnatural trehalose analogs as a reporter for *Mycobacterium tuberculosis, Nat. Chem. Biol.* 7, 228-235 (2011). S. R. Rundell, Z. L. Wagar, L. M. Meints, C. D. Olson, M. K. O'Neill, B. F. Piligian, A. W. Poston, R. J. Hood, P. J. Woodruff, B. M. Swarts, Deoxyfluoro-D-trehalose (FDTre) analogues as potential PET probes for imaging mycobacterial infection, *Org. Biomol. Chem.* 14, 8598-8609 (2016). B. M. Swarts, C. M. Holsclaw, J. C. Jewett, M. Alber, D. M. Fox, S. M. Siegrist, J. A. Leary, R. Kalscheuer, C. R. Bertozzi, Probing the mycobacterial trehalome with bioorthogonal chemistry, *J. Am. Chem. Soc.* 134, 16123-16126 (2012). H. N. Foley, J. A. Stewart, H. W. Kavunja, S. R. Rundell, B. M. Swarts, Bioorthogonal chemical reporters for selective in situ probing of mycomembrane components in mycobacteria, *Angew. Chem. Int. Ed.* 55, 2053-2057 (2016). F. P. Rodriguez-Rivera, X. Zhou, J. A. Theriot, C. R. Bertozzi, Visualization of mycobacterial membrane dynamics in live cells, *J. Am. Chem. Soc.* 139, 3488-3495 (2017). The disclosures of which are incorporated herein by reference.) Therefore, such substrate promiscuity of the antigen 85 (Ag85) complex responsible for mycolylation of trehalose permits chemical modification at specific sites of one of the trehalose's two glucose moieties, including the addition of a fluorophore whose mass exceeds that of the underlying disaccharide, without a catastrophic loss of enzymatic conversion efficiency. Accordingly, in many embodiments of the invention, a variety of trehalose and fluorogenic "reporter" dye conjugates are used in detection of viable actinobacteria, including Mtb, wherein said conjugates are metabolically incorporated into mycomembranes enabling the detection. Importantly, because the overall process of the trehalose uptake into mycomembrane depends on active metabolism, in many embodiments, actinobacteria (including Mtb) labeling with trehalose analogs uniquely distinguishes live from dead bacteria.

Figure 5:
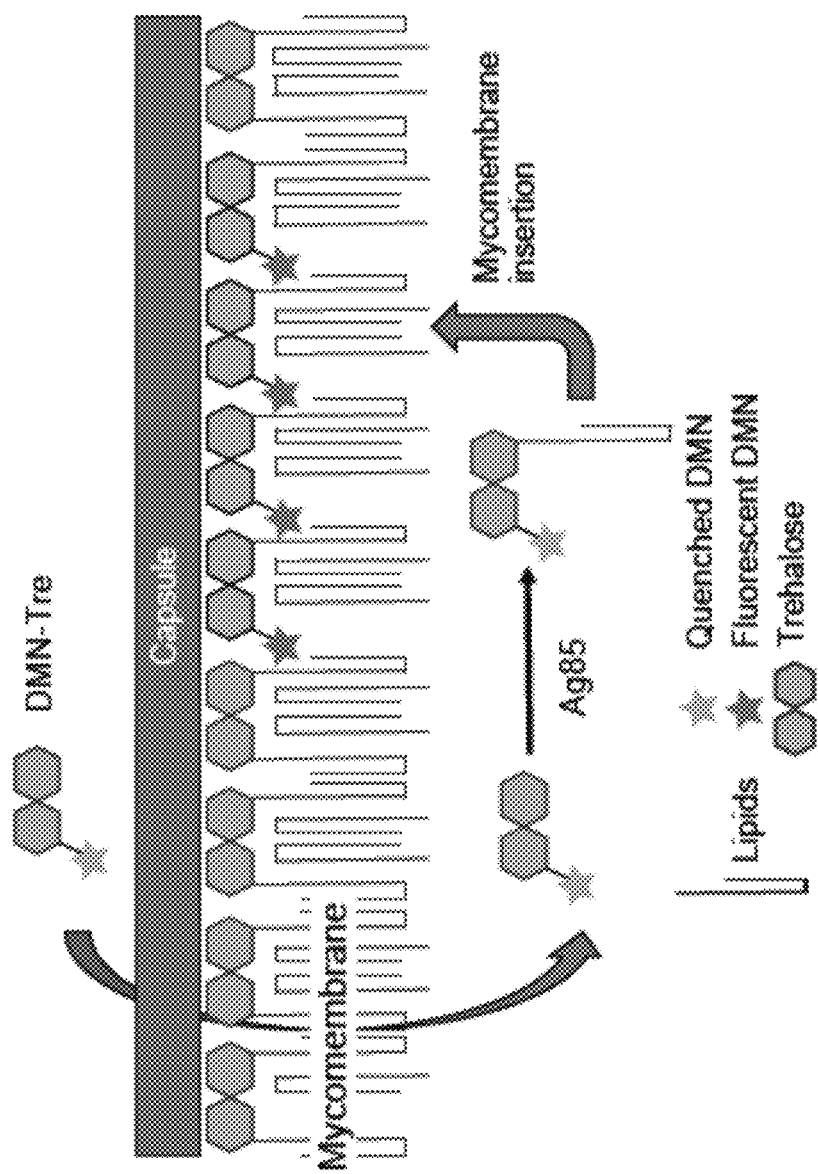
FIG. 5 provides a mycobacteria detection scheme based on the Ag85 enzyme driven metabolic incorporation of carbohydrate-solvatochromic dye conjugate into mycomembrane in accordance with embodiments of the application, wherein, used as an example, the carbohydrate is trehalose and solvatochromic dye is 4-N,N-dimethylamino-1,8-naphthalimide (DMN).

Furthermore, although any fluorescently labeled trehalose analog can be used for detection of viable actinobacteria in theory, the necessity of removing unmetabolized and, thus, unincorporated into bacterial cell wall probe to eliminate background fluorescence is a major impediment in practice. Therefore, in many embodiments, trehalose probe whose fluorescence signal is specifically activated by metabolic incorporation into the mycomembrane is used to detect live actinobacteria. More specifically, trehalose probes used for detection of actinobacteria, according to many embodiments of the invention, are conjugated to environmentally sensitive solvatochromic dyes, such as, for example, 4-N,N-dimethylamino-1,8-naphthalimide (DMN), which exhibit a dramatic fluorescence turn-on when transitioned from aqueous to hydrophobic solvents. (G. Loving, B. Imperiali, A versatile amino acid analogue of the solvatochromic fluorophore 4-N,N-dimethylamino-1,8-naphthalimide: a powerful tool for the study of dynamic protein interactions, *J. Am. Chem Soc.* 130, 13630-13638 (2008). G. Loving, B. Imperiali, Thiol-reactive derivatives of the solvatochromic 4-N,N-dimethylamino-1,8-naphthalimide fluorophore: a highly sensitive toolset for the detection of biomolecular interactions, *Bioconjug. Chem.* 20, 2133-2141 (2009). B. N. Goguen, G. S. Loving, B. Imperiali, Development of a fluorogenic sensor for activated Cdc42, *Bioorg. Med. Chem. Lett.* 21, 5058-5061 (2011). The disclosures of which are incorporated herein by reference.) As such, according to many embodiments, metabolic mycolylation of carbohydrate-solvatochromic dye conjugate by Ag85, or another enzyme with similar mycolylation abilities, followed by subsequent integration of the resulting mycolate into the hydrophobic mycomembrane, activates dye's fluorescence and enables detection of live actinobacteria (including Mtb) cells without the need to wash away unmetabolized probe. One specific example of the overall detection process using trehalose-DMN conjugate (DMN-Tre) is illustrated in FIG. 5.

Solvatochromic Dye Conjugates

Aspects of the present disclosure include solvatochromic dye-carbohydrate conjugates. Specifically, in many embodiments, the conjugate of interest is a single molecule, wherein a carbohydrate moiety is covalently linked to a solvatochromic dye. As such, in many embodiments, the carbohydrate moiety imparts the capability of metabolic uptake on the subject conjugate. Accordingly, in many embodiments, the carbohydrate moiety is derived from or structurally analogous to a naturally occurring carbohydrate of the target bacteria. In some embodiments, the carbohydrate moiety can act as a substrate for a lipid transferase enzyme of interest, whereby a hydroxyl group of the carbohydrate is esterified by the enzyme with a fatty acid lipid. In some embodiments, the lipid transferase enzyme is endogenous to the target bacteria, including actinobacteria, such as, for example, mycobacteria. Furthermore, it will be understood that, depending on the faithfulness and functionality/structure/size tolerance of the endogenous enzyme or enzymes involved in the conjugate's metabolic uptake by the target, the carbohydrate moiety can be further decorated, or otherwise altered, with additional chemical or structural features, as needed to enhance conjugate's overall efficiency and reliability as a probe.

Carbohydrate Moiety

In some embodiments carbohydrate moiety of interest includes 1 to 6 monosaccharide units, optionally glycosidically linked. In other embodiments, the carbohydrate moiety has 1 to 4 monosaccharide units. In many embodiments, the carbohydrate moiety is selected from monosaccharides and disaccharides. In some embodiments, at least one of the monosaccharide units, in some cases, a terminal monosaccharide unit of the carbohydrate, comprises a six-membered ring. In some instances, the carbohydrate moiety is a disaccharide in which both monosaccharide units have 6-membered rings.

Figure 2:
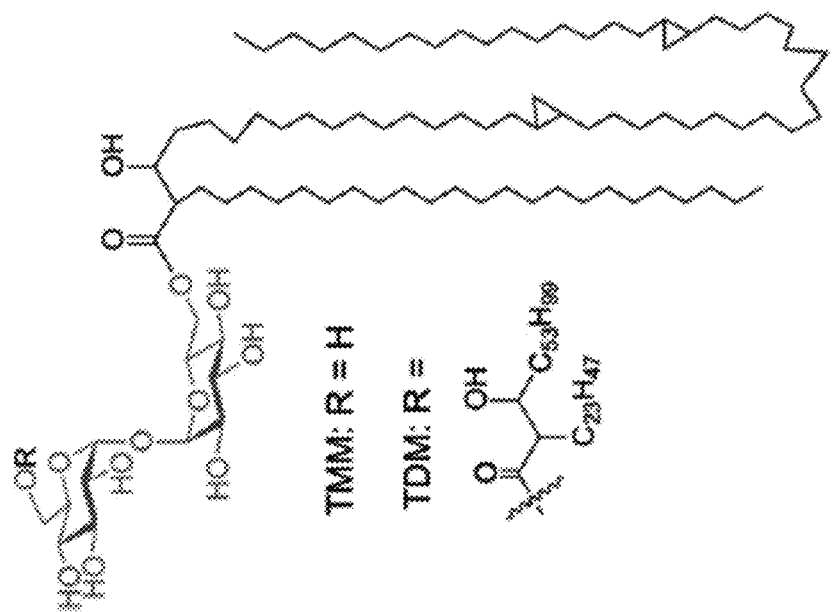
FIG. 2 shows the chemical composition and structure of trehalose monomycolate (TMM) and trehalose dimycolate (TDM) in accordance with prior art.

In some embodiments, the carbohydrate moiety is a trehalose, or a derivative, or an analog thereof. As used here a "trehalose moiety" is a carbohydrate that is structurally analogous to trehalose, and hence can interact with the target enzyme active sites, and provide selectivity for and uptake into mycobacteria. Trehalose is found in the outermost portion of the mycobacterial membrane, along with the glycolipids trehalose monomycolate (TMM) and trehalose dimycolate (TDM), as depicted in FIG. 2. α,α-1,1-Trehalose is an alpha-linked disaccharide including two α-glucose units linked by an α,α-1,1-glucoside bond. The structure including the 1-1 alpha glucoside bond makes α,α-1,1-trehalose resistant to hydrolysis and stable in solution, e.g., at high temperature and under acidic conditions. Unless otherwise indicated, as used herein, the terms "D-trehalose", "α,α-1,1-trehalose" and "α,α-trehalose" are used interchangeably to refer to the α,α-1,1-form of trehalose.

In certain instances, the carbohydrate moiety is an isomeric form of trehalose, such as α, β-trehalose, also termed neotrehalose or β, β-trehalose, also termed isotrehalose, or a hydrate thereof. In certain instances, the carbohydrate moiety is a trehalose oligosaccharide. As used herein, the term "trehalose oligosaccharide" refers to an oligosaccharide (e.g., a trisaccharide or tetrasaccharide) that includes trehalose as the base component with one, two or more optional additional sugars attached to it. In some cases, a trehalose oligosaccharide is the disaccharide trehalose. Any convenient sugars (e.g., monosaccharides or disaccharides) may be utilized in the subject trehalose oligosaccharides, including but not limited to, Glc, Galf, Gal, LGal, Man, All, LAll, Gul, Lido, Tal, Ribf, Rib, Araf, Ara, LAraf, Lara, Xyl, Lyx, and the like. In some instances, the trehalose oligosaccharide is selected from Glcα1-4Trehalose, Glcβ1-6Trehalose, Glcβ1-6Glcβ1-6Trehalose, Galα1-6Galα1-6Trehalose, and a trehalose with an α1-6Gal on one of its glucose residues and an α1-4Glc on the other glucose residue. Unless indicated otherwise, all monosaccharide codes described herein have their standard meaning. For example, Glc refers to D-glucose and Gal refers to D-galactose. In some cases, a trehalose oligosaccharide moiety includes an oligosaccharide including 5 or more units, such as 10 or more, 20 or more, 30 or more, 40 or more, 50 or more, 100 or more, 200 or more, or even more sugar units containing trehalose.

In some embodiments, the carbohydrate moiety is a derivatized version of any convenient carbohydrate. Herein, a derivative of a carbohydrate is a molecule which is based on a naturally occurring carbohydrate, with one or more of the hydroxyl or hydrogen atoms being replaced with other chemical moieties (herein derivative groups), which derivative groups do not substantially affect the ability of the probe molecule to engage with the active sites of the target enzymes (e.g., Ag85A, B or C), and hence which do not prevent incorporation of the carbohydrate-dye conjugate into mycobacteria. Such derivative groups in some cases do not inhibit the reactions which relate to incorporation of the conjugate into the actinobacteria or mycobacteria. In addition, such derivative groups are, in some embodiments, selected so as not to introduce instabilities into the probe molecule, for example by providing two anionic and/or nucleophilic groups on the same carbon atom, examples being two hydroxide groups, a hydroxide and ether group, or a hydroxide and halide group on the same carbon atom. In some embodiments, the carbohydrates or derivatives thereof have no more than one such derivative group per carbon atom of the carbohydrate substrate molecule. Examples of derivative groups include: halides, amino, substituted amino, optionally substituted linear or branched alkyl, alkenyl or alkynyl group, and optionally substituted aryl or heteroaryl group.

In some embodiments, the carbohydrate-dye conjugate has formula (I):

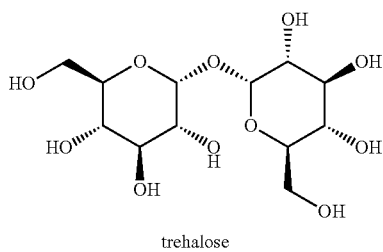 [SMILES: OC[C@H]1O[C@H](O[C@H]2O[C@H](CO)[C@@H](O)[C@H](O)[C@H]2O)[C@H](O)[C@@H](O)[C@@H]1O]

trehalose

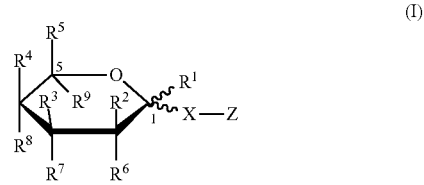

(I)

wherein:

Z is a carbohydrate or carbohydrate derivative of 1 to 5 monosaccharide units (e.g., 1 or 2 monosaccharide units) connected to C1 via a bridging group or heteroatom (X) in either an α or β configuration;

$R^1$ is H, alkyl or substituted alkyl;

$R^2$ to $R^9$ are each independently H, OH, alkoxy, substituted alkoxy, amino, substituted amino, halogen (e.g., fluoro), thiol, alkylthio, substituted alkylthio or a linked solvatochromic dye. In certain instances of formula (I), X is —O—. In certain instances of formula (I), X is —NH—. In certain instances of formula (I), Z is a monosaccharide or monosaccharide derivative.

In some embodiments, the carbohydrate-dye conjugate has the structure of formula (II):

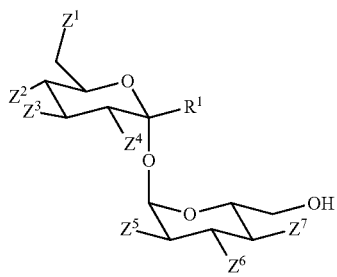

(II)

wherein $R^1$ is H, alkyl or substituted alkyl; one of $Z^1$-$Z^7$ is a linked solvatochromic dye and the rest of $Z^1$-$Z^7$ are independently selected from H, OH, alkoxy, substituted alkoxy, amino, substituted amino, halogen (e.g., fluoro), thiol, alkylthio, substituted alkylthio. In certain instances of formula (II), one and only one of $Z^1$-$Z^7$ is a linked solvatochromic dye and the rest of $Z^1$-$Z^7$ are OH. In certain embodiments of formula (II), $Z^1$ is the linked solvatochromic dye. In certain embodiments of formula (II), $Z^2$ is the linked solvatochromic dye. In certain embodiments of formula (II), $Z^3$ is the linked solvatochromic dye. In certain embodiments of formula (II), $Z^4$ is the linked solvatochromic dye. In certain embodiments of formula (II), $Z^5$ is the linked solvatochromic dye. In certain embodiments of formula (II), $Z^6$ is the linked solvatochromic dye. In certain embodiments of formula (II), $Z^7$ is the linked solvatochromic dye. In some instances of formula (II), one and only one of $Z^1$-$Z^7$ is a linked solvatochromic dye and the rest of $Z^1$-$Z^7$ are OH. In certain embodiments of formula (II), $R^1$ is H. In certain embodiments of formula (II), $R^1$ is alkyl (e.g., a lower alkyl). In certain embodiments of formula (II), $R^1$ is substituted alkyl.

In some instances of formula (II), the carbohydrate-dye conjugate has formula (III):

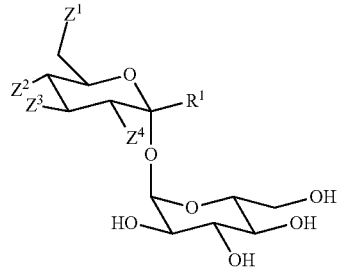

(III)

wherein $R^1$ is H, alkyl or substituted alkyl; one and only one of $Z^1$-$Z^4$ is a linked solvatochromic dye and the rest of $Z^1$-$Z^4$ are independently selected from H, OH, alkoxy, substituted alkoxy, amino, substituted amino, halogen (e.g., fluoro), thiol, alkylthio, substituted alkylthio. In some instances of formula (III), one and only one of $Z^1$-$Z^4$ is a linked solvatochromic dye and the rest of $Z^1$-$Z^4$ are OH. In certain embodiments of formula (III), $Z^1$ is the linked solvatochromic dye. In certain embodiments of formula (III), $Z^2$ is the linked solvatochromic dye. In certain embodiments of formula (III), $Z^3$ is the linked solvatochromic dye. In certain embodiments of formula (III), $Z^4$ is the linked solvatochromic dye. In certain embodiments of formula (III), $R^1$ is H. In certain embodiments of formula (III), $R^1$ is alkyl (e.g., a lower alkyl). In certain embodiments of formula (III), $R^1$ is substituted alkyl.

certain embodiments of formulae (II) and (III), the carbohydrate-dye conjugate has formula (IV):

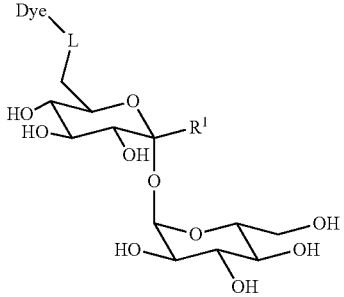

(IV)

wherein L is an optional linker, Dye is a solvatochromic dye, and $R^1$ is H, alkyl or a substituted alkyl.

In certain embodiments of formulae (II) and (III), the carbohydrate-dye conjugate has formula (V):

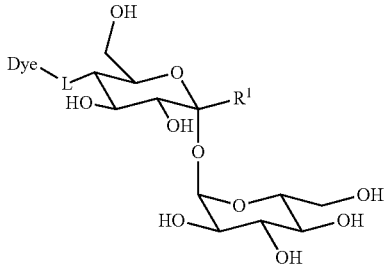

(V)

wherein L is an optional linker, Dye is a solvatochromic dye, and $R^1$ is H, alkyl or a substituted alkyl.

certain embodiments of formulae (II) and (III), the carbohydrate-dye conjugate has formula (VI):

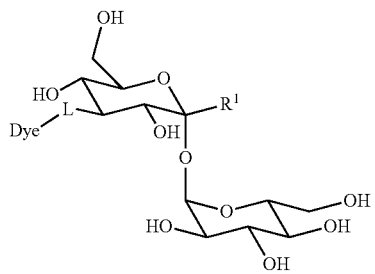

(VI)

wherein L is an optional linker, Dye is a solvatochromic dye, and $R^1$ is H, alkyl or a substituted alkyl.

In certain embodiments of formulae (II) and (III), the carbohydrate-dye conjugate has formula (VII):

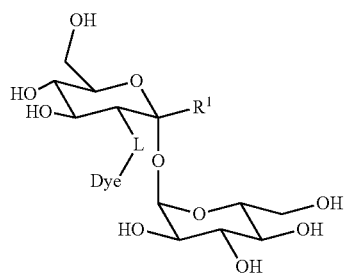

(VII)

wherein L is an optional linker, Dye is a solvatochromic dye, and $R^1$ is H, alkyl or a substituted alkyl.

In certain embodiments of formula (II), the carbohydrate-dye conjugate has formula (VIII):

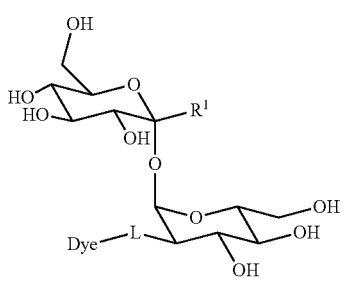

(VIII)

wherein L is an optional linker, Dye is a solvatochromic dye, and $R^1$ is H, alkyl or a substituted alkyl.

In certain embodiments of formula (II), the carbohydrate-dye conjugate has formula (IX):

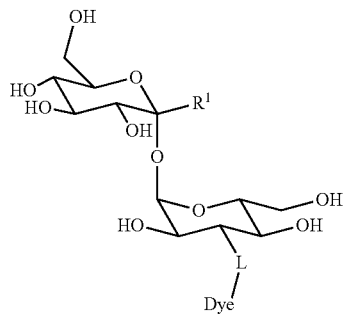

(IX)

wherein L is an optional linker, Dye is a solvatochromic dye, and $R^1$ is H, alkyl or a substituted alkyl.

In certain embodiments of formula (II), the carbohydrate-dye conjugate has formula (X):

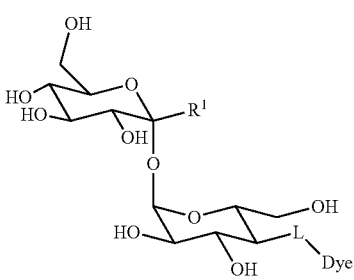

(X)

wherein L is an optional linker, Dye is a solvatochromic dye, and $R^1$ is H, alkyl or a substituted alkyl In certain embodiments of formulae (IV) to (X), $R^1$ is H. In certain embodiments of formulae (IV) to (X), $R^1$ is alkyl (e.g., a lower alkyl, such as methyl). In certain embodiments of formulae (IV) to (X), $R^1$ is substituted alkyl. In certain embodiments of formulae (IV) to (X), L is —NH-$L^1$- where $L^1$ is a linker such as an alkyl or substituted alkyl. In certain embodiments of formulae (IV) to (X), L comprises —NH—CO—. In certain embodiments of formulae (IV) to (X), L comprises —NHC(=X)NH— where X is O or S. In certain embodiments of formulae (IV) to (X), L comprises —NHC(=O)O—. In certain embodiments of formulae (IV) to (X), L is an alkyl or substituted alkyl linker.

Solvatochromic Dye Moiety

As summarized above, the color and/or transparency of the solvatochromic dye depends upon the immediate environment of the dye. Solvent polarity, as well as hydrogen bonding and other environmental factors, plays a significant role in determining the ground state and excited state energy levels that in turn determine the color and/or transparency of the dye. As used herein, the term "solvatochromic dye" refers to a detectable dye molecule that exhibits a detectable change in a spectroscopic property due to a change in solvent polarity. The spectroscopic property change can include a change in color (i.e., a wavelength shift of maximum absorption or emission wavelength) with increasing solvent polarity. In some cases, the spectroscopic property change can include a change in molar absorptivity or quantum yield with increasing solvent polarity.

Any convenient solvatochromic dye can be adapted for use in the subject carbohydrate-dye conjugates. The solvatochromic dye can be linked to a carbohydrate moiety (e.g., as described above) at any convenient positions of the dye and the carbohydrate moiety to produce a carbohydrate-dye conjugate that is capable of uptake by a target bacterial cell. Solvatochromic dyes of interest include, but are not limited to, merocyanine dyes, Reichardt's dye, 1-Docosyl-4-(4-hydroxystyryl)-pyridinium bromide, 2,6-dichloro-4-(2,4,6-triphenyl-N-pyridinio)-phenolate, 1-(4-hydroxyphenol)-2,4,6-triphenylpyridinium hydroxide, other pyridinium N-phenoxide betaines, zwitterionic dyes, 4-[2-N-substituted-1,4-hydropyridin-4-ylidine)ethylidene]cyclohexa-2,5-di-en-1-one, red pyrazolone dyes, azomethine dyes, indoaniline dyes, diazamerocyanine dyes, and mixtures thereof and those dyes described by MacDonald et al. in U.S. Pat. No. 7,829,181, the disclosure of which is herein incorporated by reference. Zwitterionic dyes (or chromogens) are dyes in which formal positive and negative charges are contained within a contiguous pi-electron system. Other solvatochromic dyes include, but are not limited to, pyrene, 4-dicyanmethylene-2-methyl-6-(p-dimethyl-aminostyryl)-4H-pyran; 6-propionyl-2-(dimethylamino) naphthalene; 9-(diethyl-amino)-5H-benzo[a]phenoxazin-5-one; phenol blue; stilbazolium dyes; coumarin dyes; ketocyanine dyes; thymol blue, congo red, methyl orange, bromocresol green, methyl red, bromocresol purple, bromothymol blue, cresol red, phenolphthalein, seminaphthofluorescein (SNAFL) dyes, seminaphtharhodafluor (SNARF) dyes, 8-hydroxy-pyrene-1,3,6-trisulfonic acid, fluorescein and its derivatives, oregon green, and a variety of dyes mostly used as laser dyes including rhodamine dyes, styryl dyes, cyanine dyes, and a large variety of other dyes. Still other solvatochromic dyes may include indigo, 4-dimethylaminophthalimide (4-DMAP), 6-dimethylaminonaphthalimide (6-DMN), 4-dicyanmethylene-2-methyl-6-(p-dimethylaminostyryl)-4H-pyran (DCM); 6-propionyl-2-(dimethylamino)-naphthalene (PRODAN); 9-(diethylamino)-5H-benzo[a]phenox-azin-5-one (Nile Red); 4-(dicyanovinyl)julolidine (DCVJ); phenol blue; stilbazolium dyes; coumarin dyes; ketocyanine dyes; N,N-dimethyl-4-nitroaniline (NDMNA) and N-methyl-2-nitroaniline (NM2NA); Nile blue; 1-anilinonaphthalene-8-sulfonic acid (1,8-ANS), Anthradan, 7-Nitrobenz-2-oxa-1,3-diazol-4-yl (NBD), NBD-TMA ([2-(4-nitro-2,1,3-benzoxadiazol-7-yl)aminoethyl]trimethylammonium), dapoxylbutylsulfonamide (DBS) and other dapoxyl analogs. Other suitable dyes, according to some embodiments, include, but are not limited to: 4-[2-N-substituted-(1,4-hydropyridin-4-ylidine)ethylidene]cyclohexa-2,5-dien-1-one, red pyrazolone dyes, azomethine dyes, indoaniline dyes, and mixtures thereof.

In some embodiments of formulae (I)-(X), the linked solvatochromic dye of the carbohydrate-dye conjugate is of formula (XI):

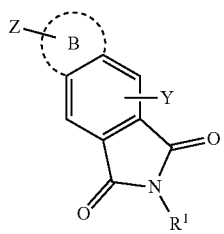

(XI)

wherein:
B is an optional fused 5 or 6-membered aryl or heteroaryl ring, optionally further substituted with one or more Z substituents independently selected from H, alkyl, substituted alkyl, halogen (e.g., chloro or fluoro), hydroxyl, amino, substituted amino, cyano, nitro, carboxy, alkoxy, substituted alkoxy;
Y is one or more substituents independently selected from H, alkyl, substituted alkyl, halogen (e.g., chloro or fluoro), hydroxyl, amino, substituted amino, cyano, nitro, alkoxy and substituted alkoxy, wherein at least one Y or Z is —NR$_2$; R$^1$ is selected from H, alkyl and substituted alkyl; and
wherein at least one Z, Y or R$^1$ is linked to the carbohydrate moiety of the conjugate via an optional linker. In certain embodiments of formula (XI), R$^1$ is linked to the carbohydrate moiety of the conjugate.

In certain instances of formula (XI), the carbohydrate-dye conjugate has the following structure:

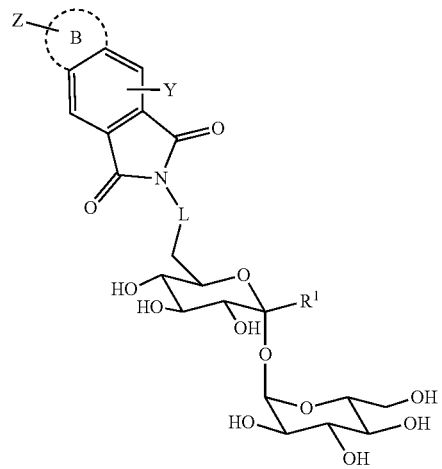

where L is an optional linker and R$^1$ is as defined above.

In some embodiments of formulae (I)-(X), the linked solvatochromic dye of the carbohydrate-dye conjugate is of formula (XII):

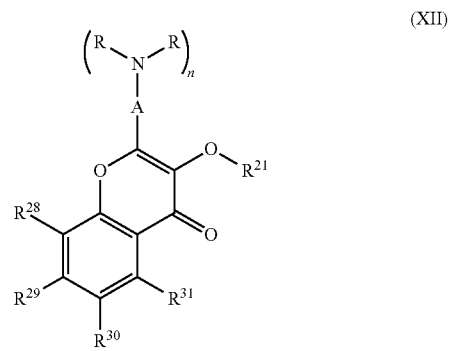

(XII)

wherein:
A is an aryl or heteroaryl system comprising up to three, 5 or 6-membered rings, optionally further substituted with one or more Z substituents independently selected from H, alkyl, substituted alkyl, halogen (e.g., chloro or fluoro), hydroxyl, amino, substituted amino, cyano and nitro;
n is 0 or 1;
each R and R$^{21}$ is independently selected from H, alkyl and substituted alkyl; and $R^{28}$—$R^{31}$ are each independently selected from H, alkyl, substituted alkyl, alkoxy, substituted alkoxy, halogen (e.g., chloro or fluoro), hydroxyl, amino, substituted amino, cyano, and nitro;

wherein at least one of Z, $R^{21}$ and $R^{28}$-$R^{31}$ is linked to the carbohydrate moiety of the conjugate via an optional linker.

In certain instances of formula (XII), the carbohydrate-dye conjugate has the following structure:

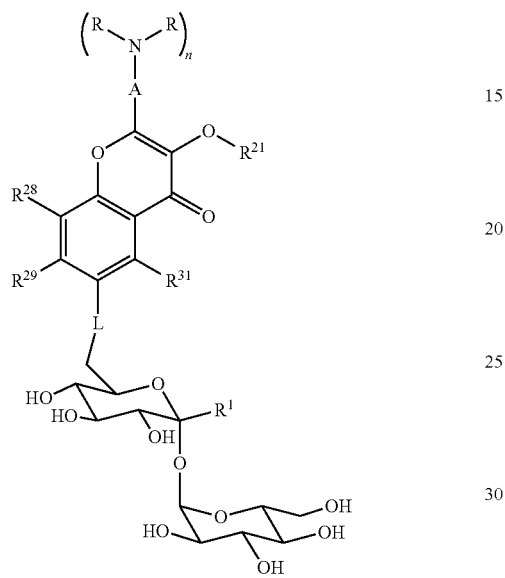

where L is an optional linker and $R^1$ is as defined above.

In some embodiments of formulae (I)-(X), the linked solvatochromic dye of the carbohydrate-dye conjugate is of formula (XIII)

(XIII)

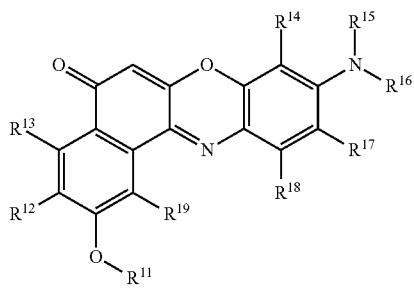

wherein:
$R^{11}$, $R^{15}$ and $R^{16}$ are independently selected from H, alkyl and substituted alkyl; and
$R^{12}$-$R^{14}$, $R^{17}$-$R^{19}$ are each independently selected from H, alkyl, substituted alkyl, alkoxy, substituted alkoxy, halogen (e.g., chloro or fluoro), hydroxyl, amino, substituted amino, cyano and nitro;
wherein at least one of $R^{11}$, $R^{12}$-$R^{14}$, $R^{17}$-$R^{19}$ is linked to the carbohydrate moiety of the conjugate via an optional linker.

In certain instances of formula (XIII), the carbohydrate-dye conjugate has the following structure:

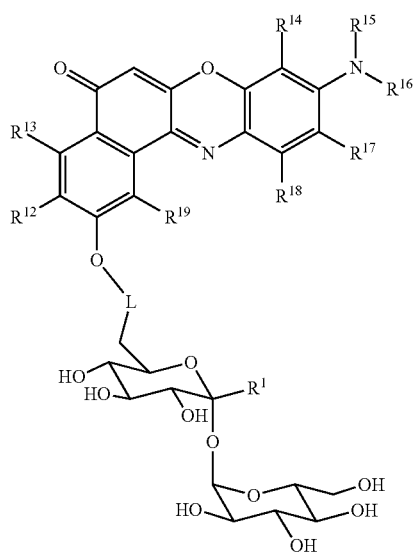

where L is an optional linker and $R^1$ is as defined above.

In some embodiments of formulae (I)-(X), the linked solvatochromic dye of the carbohydrate-dye conjugate is of formula (XIV):

(XIV)

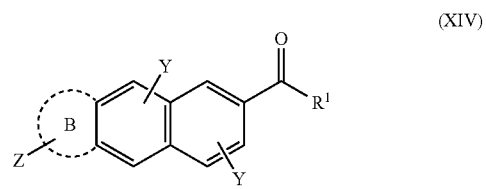

wherein:
B is an optional fused 5 or 6-membered aryl or heteroaryl ring, optionally further substituted with one or more Z substituents independently selected from H, alkyl, substituted alkyl, halogen (e.g., chloro or fluoro), hydroxyl, amino, substituted amino, cyano, nitro, carboxy, alkoxy, substituted alkoxy;
Y is one or more substituents independently selected from H, alkyl, substituted alkyl, halogen (e.g., chloro or fluoro), hydroxyl, amino, substituted amino, cyano, nitro, alkoxy and substituted alkoxy,
$R^1$ is selected from H, alkyl and substituted alkyl; and
wherein at least one of $R^1$, Y and Z is linked to the carbohydrate moiety of the conjugate via an optional linker. In some cases, at least one Y or Z is —$NR_2$.

In some embodiments of formulae (I)-(X), the linked solvatochromic dye of the carbohydrate-dye conjugate is of formula (XV):

(XV)

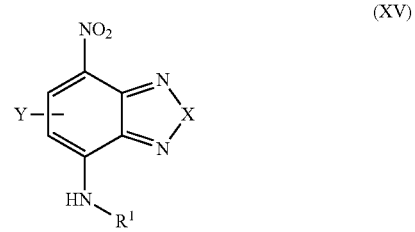

wherein:

X is O, S or NR¹;

Y is one or more substituents independently selected from H, alkyl, substituted alkyl, halogen (e.g., chloro or fluoro), hydroxyl, amino, substituted amino, cyano, nitro, alkoxy and substituted alkoxy;

each R¹ is independently selected from H, alkyl and substituted alkyl; and wherein at least one of R¹ and Y is linked to the carbohydrate moiety of the conjugate via an optional linker.

In some embodiments of formulae (I)-(XV), the linked solvatochromic dye is of one of formula (XVI)-(XXV):

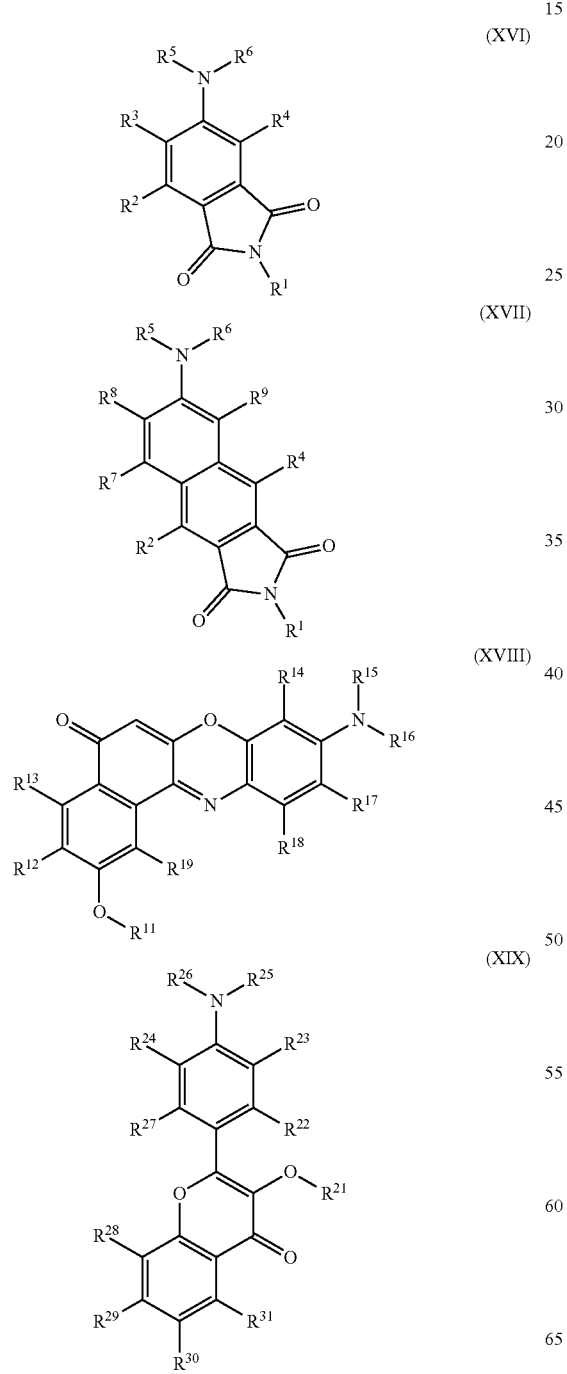

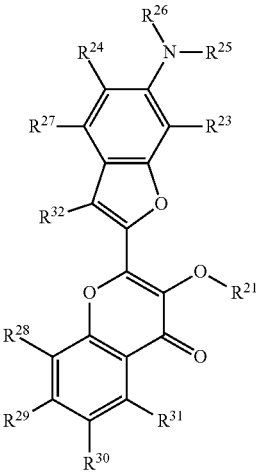

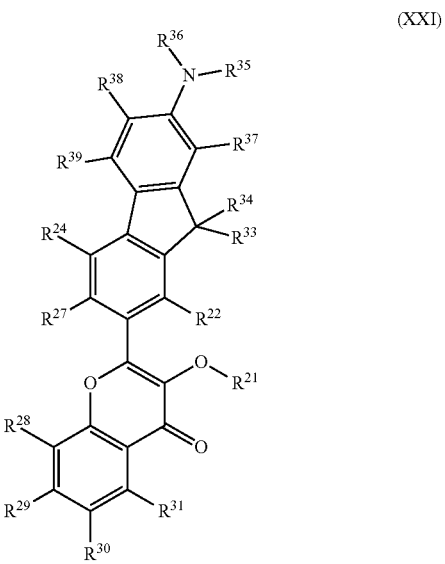

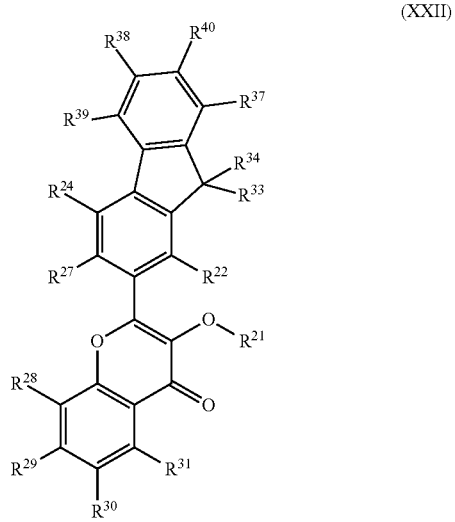

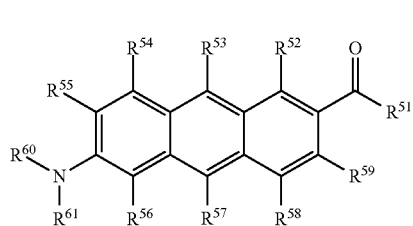

(XXIII)

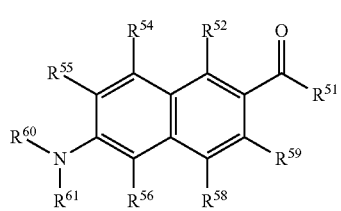

(XXIV)

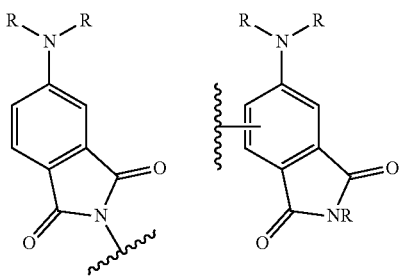

(XXV)

wherein

R$^1$, R$^5$, R$^6$, R$^{11}$, R$^{15}$, R$^{16}$, R$^{21}$, R$^{25}$, R$^{26}$, R$^{33}$-R$^{35}$, R$^{36}$, R$^{51}$, R$^{60}$ and R$^{61}$ are independently selected from H, alkyl and substituted alkyl; and R$^2$-R$^4$, R$^7$-R$^9$, R$^{12}$-R$^{14}$, R$^{17}$-R$^{19}$, R$^{22}$-R$^{24}$, R$^{27}$-R$^{32}$, R$^{37}$-R$^{40}$ and R$^{52}$-R$^{59}$ are each independently selected from H, alkyl, substituted alkyl, alkoxy, substituted alkoxy, halogen (e.g., chloro or fluoro), hydroxyl, amino, substituted amino, cyano and nitro;

wherein at least one of R$^1$-R$^{61}$ is linked to the carbohydrate of the conjugate via an optional linker.

certain embodiments of formulae (I)-(XXV), the solvatochromic dye is selected from one of the following structures:

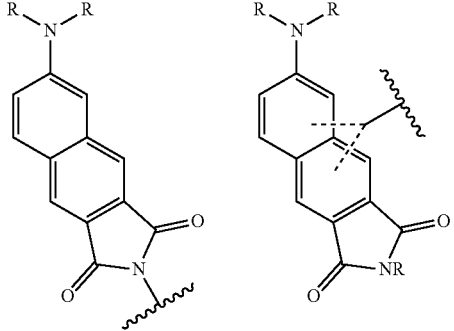

wherein each R is independently H, an alkyl or a substituted alkyl, and the solvatochromic dye is linked to the carbohydrate moiety via any convenient position. In certain instances, each R is independently H or a lower alkyl such as methyl or ethyl In certain embodiments of formulae (I)-(XXV), the solvatochromic dye is selected from one of the following structures:

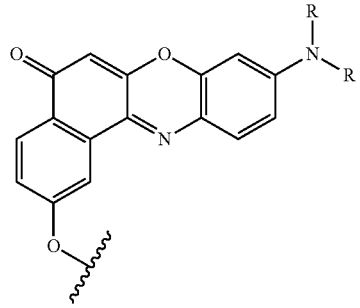

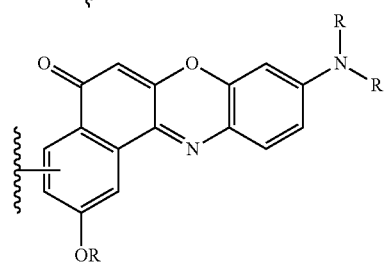

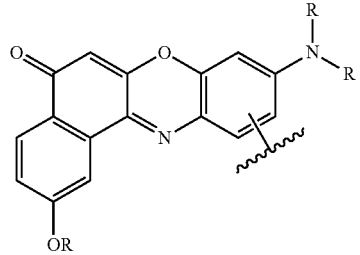

wherein each R is independently H, an alkyl or a substituted alkyl, and the solvatochromic dye is linked to the carbohydrate moiety via any convenient position. In certain instances, each R is independently H or a lower alkyl such as methyl or ethyl.

In certain embodiments of formulae (I)-(XXV), the solvatochromic dye is selected from one of the following structures:

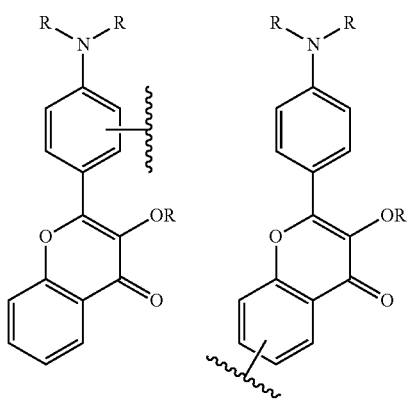
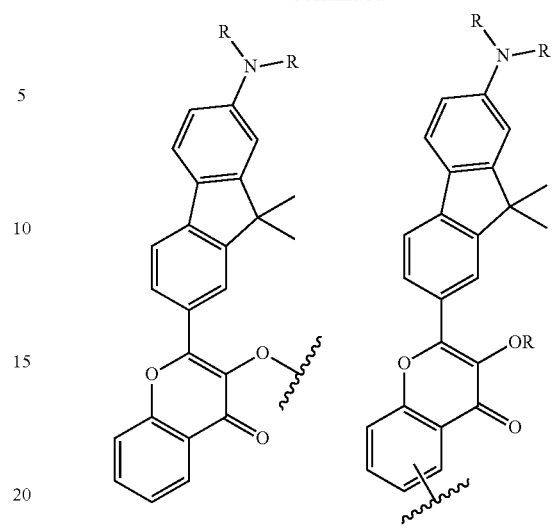
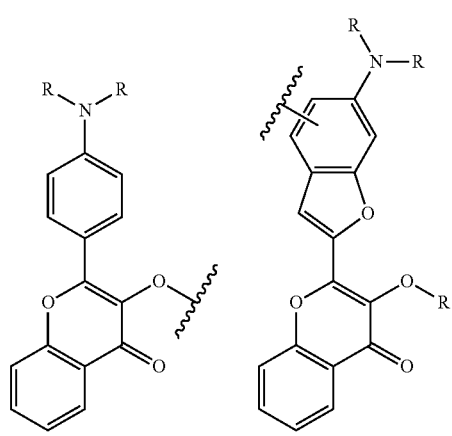
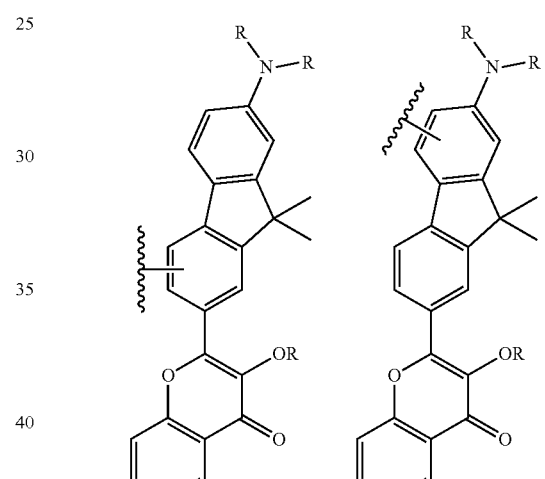
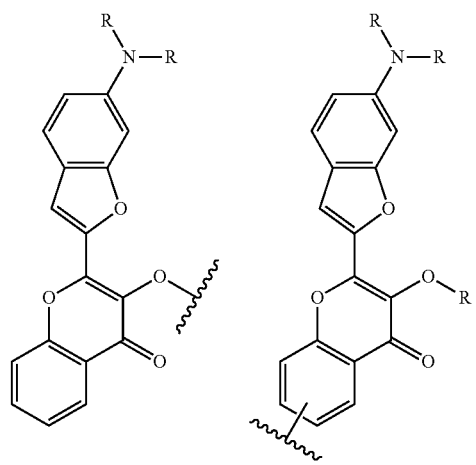
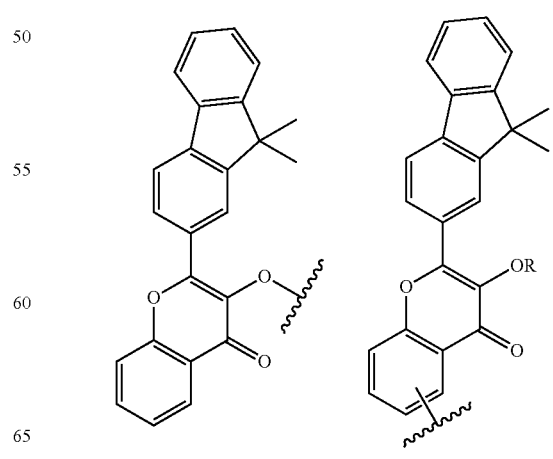

-continued

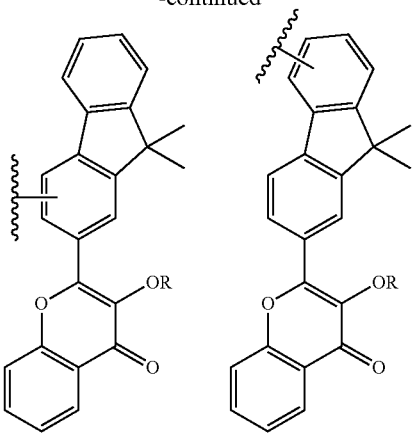

wherein each R is independently H, an alkyl or a substituted alkyl, and the solvatochromic dye is linked to the carbohydrate moiety via any convenient position. In certain instances, each R is independently H or a lower alkyl such as methyl or ethyl.

In certain embodiments of formulae (I)-(XXV), the solvatochromic dye is selected from one of the following structures:

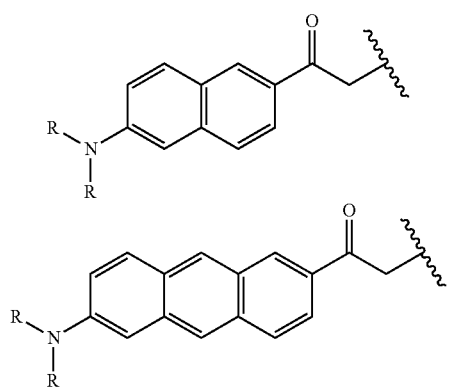

wherein each R is independently H, an alkyl or a substituted alkyl, and the solvatochromic dye is linked to the carbohydrate moiety via any convenient position. In certain instances, each R is independently H or a lower alkyl such as methyl or ethyl.

In certain embodiments of formulae (I)-(XXV), the solvatochromic dye has the following structure:

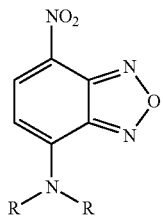

wherein each R is independently H, an alkyl or a substituted alkyl, and the solvatochromic dye is linked to the carbohydrate moiety via any convenient position. In certain instances, one R is linked to the carbohydrate moiety.

In certain instances of formula (I)-(X), the linked solvatochromic dye is selected from 4-DMAP, 4-DMN, 6-DMN, Nile Red, 3-HC, 3-MC, PRODAN, Anthradan, NBD and derivatives thereof. In certain instances of formula (I)-(X), the linked solvatochromic dye is 4-DMAP. In certain instances of formula (I)-(X), the linked solvatochromic dye is 4-DMN or 6-DMN. In certain instances of formula (I)-(X), the linked solvatochromic dye is Nile Red. In certain instances of formula (I)-(X), the linked solvatochromic dye is 3-HC. In certain instances of formula (I)-(X), the linked solvatochromic dye is PRODAN. In certain instances of formula (I)-(X), the linked solvatochromic dye is Anthradan. In certain instances of formula (I)-(X), the linked solvatochromic dye is NBD.

In certain instances of formula (I)-(X), the linked solvatochromic dye is selected from one of the following structures:

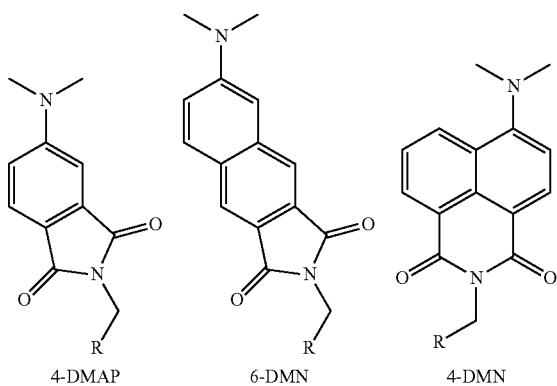

4-DMAP  6-DMN  4-DMN

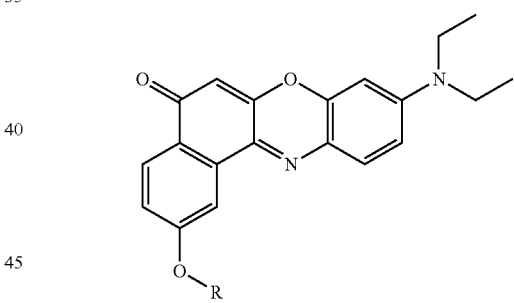

Nile Red

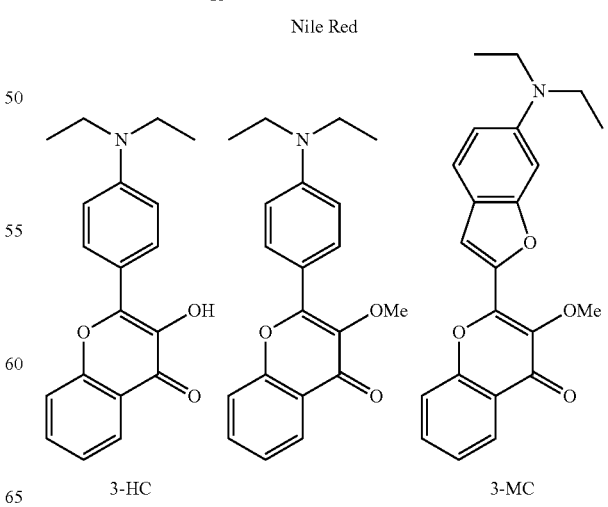

3-HC  3-MC

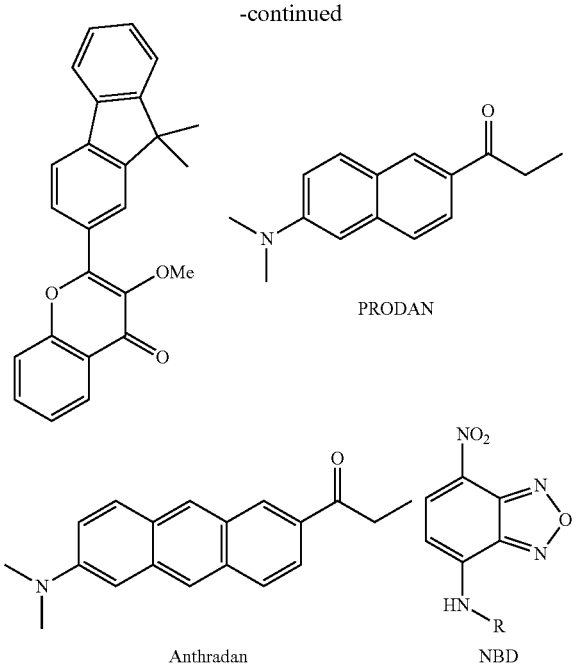

or an analog thereof, wherein the solvatochromic dye is linked to the carbohydrate at any available position (e.g., the R position).

Figure 6:
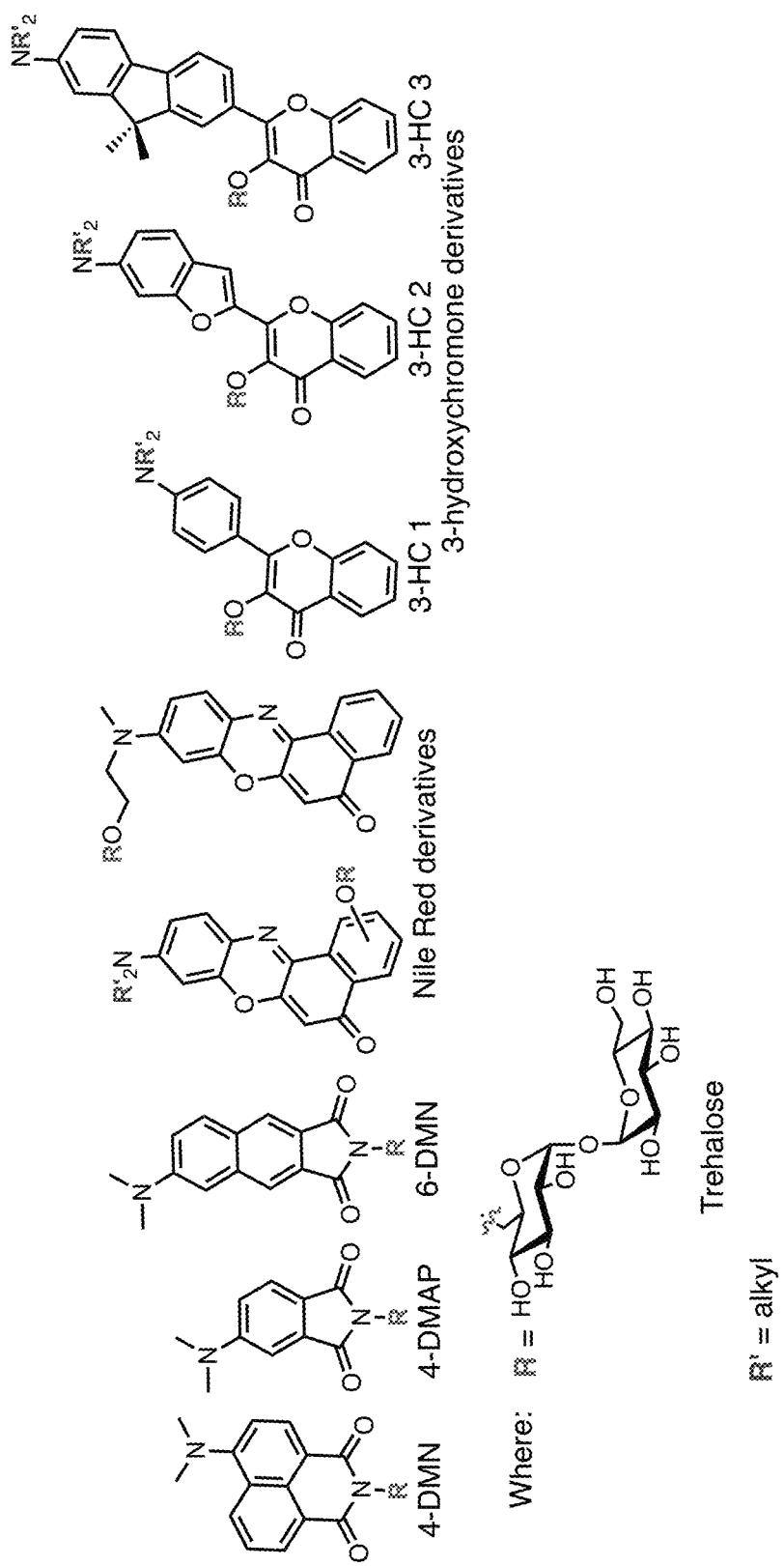
FIGS. 6, 7A and 7B provide examples of trehalose-fluorescent solvatochromic dye conjugates in accordance with embodiments of the application.
Figure 7A:
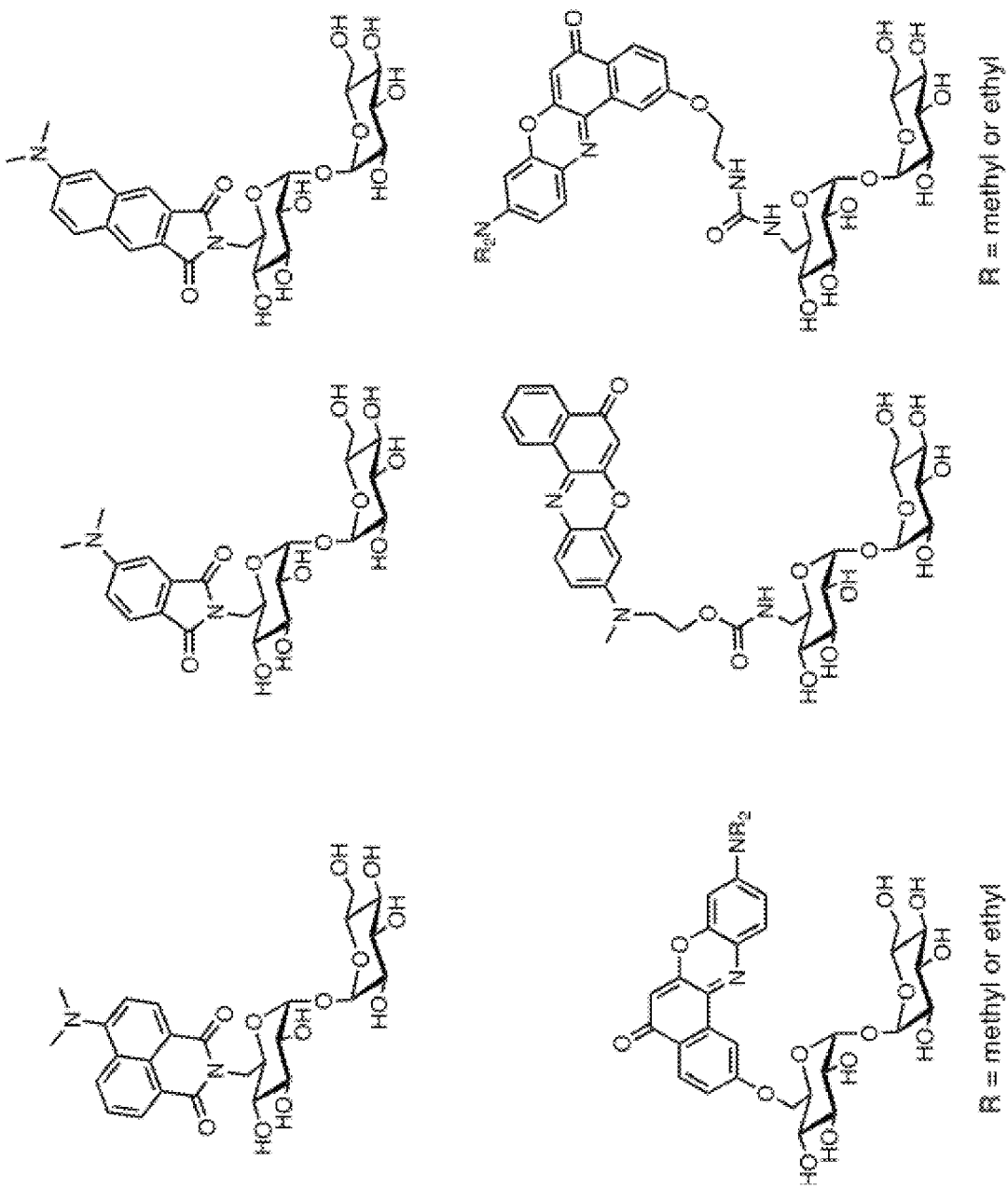
Figure 7B:
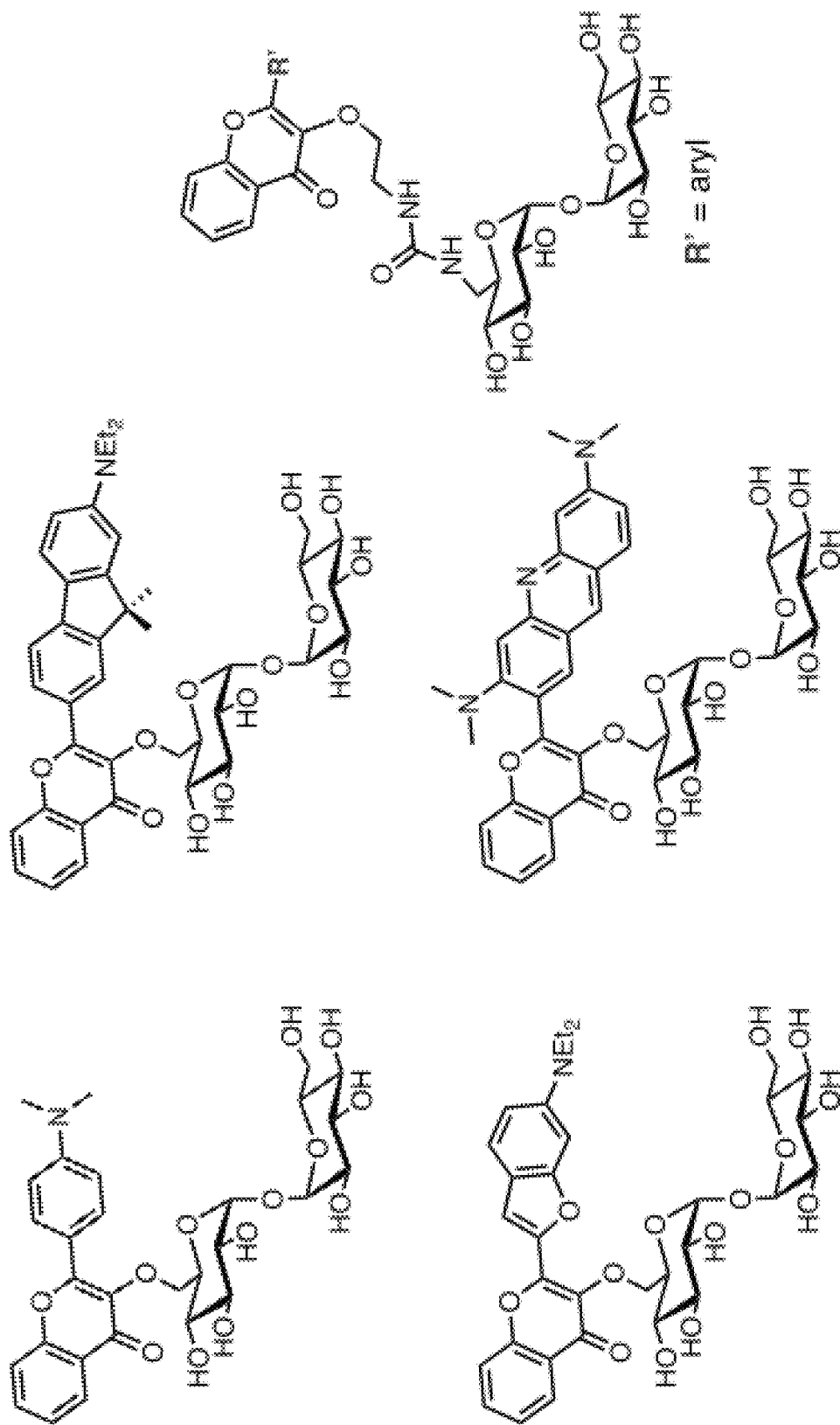

In addition, FIGS. 6, 7A and 7B provide examples of several specific trehalose-fluorescent solvatochromic dye conjugates in accordance with embodiments that have either demonstrated their utility in the detection of several strains of live actinobacteria according to the embodiments of this disclosure, or are expected to perform well in the same. Specifically, FIG. 6 demonstrates solvatochromic trehalose probes/conjugates based on: phthalimide- and naphthalimide-dyes, including DMN-Tre (1-3); Nile Red dye, wherein different positions of the dye are used for attachment to trehalose via linkers of different lengths (4-5); and variations of 3-hydroxychromone dye, wherein the aryl group of the dye is varied to modify the dye's fluorescence signal, attached to trehalose by linkers of different lengths (6-8).

Methods of Detecting Bacteria

The present disclosure provides methods of detecting live bacteria in a biological sample. In many embodiments, the methods generally involve: a) contacting a biological sample to be tested (e.g., a biological sample containing, or suspected of containing, a live bacterial cell of interest, with a carbohydrate-solvatochromic dye conjugate (e.g., as described herein); and b) detecting a spectroscopic signal from the dye due to the changes in the dye's local environment upon interaction with the tested sample. In many embodiments, the solvatochromic dyes used in the detection methods are fluorogenic and the spectroscopic signal to be detected is fluorescence. In many embodiments, the dye's fluorescence is turned on (enhanced) to produce a detectable signal by the interactions with the target, while remaining undetectable in the absence of target encounters. In many embodiments, the bacteria of interest for detection are actinobacteria, such as mycobacteria.

The detection of a spectroscopic signal, such as, for example, fluorescence, from the solvatochromic dye of the conjugate indicates the presence of the target metabolically active bacterial cell in the sample, since target cells will metabolically label the conjugate leading to uptake of the labelled conjugate into the bacterial cell wall, where the solvatochromic dye exhibits a change in spectroscopic properties. In some instances, the target bacterial cell includes a cell wall comprising mycolic acid. In certain cases, the fluorogenic carbohydrate-solvatochromic dye conjugate is a trehalose-solvatochromic dye conjugate (e.g., as described herein), which is metabolically labelled with a mycolic acid of the target bacterial cell. In certain embodiments, the live bacterial cell is a target *mycobacterium*.

A method of the present disclosure provides for detection of as few as $10^4$ target live bacterial cells (e.g., mycobacteria) in a sample, such as fewer than $5 \times 10^3$ fewer than $10^3$, fewer than $5 \times 10^2$, fewer than $10^2$, fewer than 50, or fewer than 10 target bacterial cells (e.g., mycobacteria) in the sample. In some cases, the subject method provides for detection of $5 \times 10^3$/mL target live bacterial cells or less, such as $10^3$/mL or less, $5 \times 10^2$/mL or less, $10^2$/mL or less, 50/mL or less, or 10/mL or less, mycobacteria in a biological sample.

In some instances, the subject method provides for detection of 500 colony forming units (CFU) of a target mycobacteria per mL or less, such as 200 CFU/mL or less, 100 CFU/mL or less, 90 CFU/mL or less, 80 CFU/mL or less, 70 CFU/mL or less, 60 CFU/mL or less, 50 CFU/mL or less, 40 CFU/mL or less, 30 CFU/mL or less, 20 CFU/mL or less, 10 CFU/mL or less, 8 CFU/mL or less, 6 CFU/mL or less, 5 CFU/mL or less, 4 CFU/mL or less, 3 CFU/mL or less, 2 CFU/mL or less, or even less. Any convenient methods can be utilized to detect bacterial cells and colony forming units of bacterial cells of interest in a sample, e.g., microscopy methods, colorimetric bacterial cell assays and the like.

The subject methods can be utilized to identify and distinguish metabolically active mycobacteria in a biological sample from non-metabolically active mycobacteria and other microorganisms. The subject methods can be utilized to identify and distinguish target mycobacteria from non-target mycobacteria. Non-target mycobacteria can include microorganisms that are not actinobacteria or mycobacteria, which may be metabolically active or not.

Mycobacteria that can be detected using a method of the present disclosure include any convenient mycobacterial species. Mycobacteria of interest includes but are not limited to those mycobacteria provided in Table 1, including, *M. tuberculosis, M. avium* (or *M. avium-intracellulare*), *M. leprae* (particularly *M. leprae* infection leading to tuberculoid leprosy), *M. kansasii, M. fortuitum, M. chelonae, M. absecessus, M. marinum, M. Nocardia, M. xenopi, M. simiae, M. szulgai, M. scrofulaceum, M. malmoense, M. terrae-nonchromogenicum* complex, *M. haemophilum, M. genavense, M. celatum, M. interjectum, M. confluentis, M. triplex, M. lentiflavum, M. branderi, M. conspicuum, M. cookii, M. asiaticum, M. marinum M. gordonae, M. fortuitum, M. chelonae-abscessu*, and *M. mucogenicum*. While detection of mycobacteria in biological samples from humans is of interest, detection of mycobacteria biological samples from non-human subjects is also of interest. For example, *M. avium* causes lymphadenitis in slaughter pigs; M. paratuberculosis infection causes paratuberculosis, a tuberculosis-like disease that can result in great production losses in cattle, sheep and goats; and *M. bovis* is carried by cattle and can cause a tuberculin-like infection in humans. Thus, in some cases, the biological sample is obtained from a pig; and a method of the present disclosure detects *M. avium* in the biological sample. In some cases, the biological sample is obtained from a cow, a sheep, or a goat; and a method of the present disclosure detects M. paratuberculosis in the biological sample. Mycobacteria of interest include animal and plant pathogens carrying the mycolic acid membrane. In some cases, bacteria can be targeted that are part of the Corynebacterineæ suborder. In certain instances, the subject methods can be adapted to detect a bacterium of the *Corynebacterium* family, such as *Corynebacterium glutamicum* or *Corynebacterium diphtherie*.

In some embodiments, the biological sample is obtained from a human; and a method of the present disclosure detects *M. tuberculosis* in the biological sample. In some cases, the individual has a human immunodeficiency virus (HIV) infection and in addition has, or is suspected of having or being at risk of infection with, TB. In some cases, the individual is living in an area in which TB is endemic. In some cases, the individual is military personnel. In some cases, the individual is incarcerated (e.g., living in a prison). In some cases, the individual is immunocompromised.

A "biological sample" encompasses a variety of sample types obtained from an individual or a group of individuals, directly (e.g., drawn or swabbed from a body) or indirectly (e.g. from the individual's or group's environment, such as air, water, or an inanimate surface), and can be used in a diagnostic or monitoring assay. The definition encompasses blood and other liquid samples of biological origin, solid tissue samples such as a biopsy specimen or tissue cultures or cells derived therefrom and the progeny thereof. It will be understood that air or water samples, or solid inanimate surfaces or objects, such as, for example, air or water filters, room walls or windows, or laboratory equipment, that can potentially contain the biological sample of interest (via, for example, direct contact) are also included. The definition also includes samples that have been manipulated in any way after their procurement, such as by treatment with reagents, solubilization, or enrichment for certain components, such as polynucleotides. The term "biological sample" encompasses a clinical sample, and includes cells in culture, cell supernatants, cell lysates, blood, serum, plasma, biological fluid, buccal swab (e.g., cheek swab) and tissue samples. Biological fluids include sputum, buccal swab saliva, cerebrospinal fluid, urine, bronchoalveolar lavage fluid, and the like. In some embodiments, the sample is a sputum sample. In other embodiments, the sample is a buccal swab (e.g., cheek swab). In yet other embodiments, the sample is air filter.

In general, the subject methods are performed in vitro. Any convenient method may be used to contact the sample with the conjugate. In some instances, the sample is contacted with the conjugate under conditions in which the conjugate is taken up into the cell wall of the bacterial cell, if present. In some cases, for metabolic labelling and uptake of the conjugate to the target bacterial cell, an appropriate solution may be used that maintains the viability of the cells. The solution may be a balanced salt solution, e.g., normal saline, PBS, Hank's balanced salt solution, etc., conveniently supplemented with fetal calf serum, human platelet lysate or other factors, in conjunction with an acceptable buffer at low concentration, such as from 5-25 mM. In some other embodiments, a sample of interested dispersed in air or water is contacted with the detecting conjugate by passing the said sample through an air or water filter having the conjugate on its sample contacting surface.

The temperature at which contacting the sample with the solvatochromic dye-sugar conjugate is performed may vary, and in some instances may range from 5° C. to 50° C., such as from 10° C. to 40° C., 15° C. to 40° C., 20° C. to 40° C., e.g., 20° C., 25° C., 30° C., 35° C. or 37° C. In some instances, the temperature at which contacting takes place is selected to be compatible with the biological activity or viability of the target bacteria, e.g., target mycobacteria, and/or other components of the sample. In certain instances, the temperature is 25° C., 30° C., 35° C. or 37° C. In certain cases, the temperature at which the contacting takes place is room temperature (e.g., 25° C., 30° C., 35° C. or 37° C.). Any convenient incubation time for incubating the contacted sample may be selected to allow for the incorporation of a desirable amount of the conjugate into the target bacterial cell, and in some instances, may be 1 minute (min) or more, such as 2 min or more, 10 min or more, 30 min or more, 1 hour or more, 2 hours or more, 6 hours or more, 12 hours or more, or even 24 hours or more.

The subject methods provide for a method that does not require a washing step, e.g., where cells in the sample are immobilized and/or washing prior to detection to remove excess dye reagents that can cause background signals. In the subject methods detection can be performed directly on the contact sample.

In some instances, the sample can be diluted prior to detection. Dilution can be performed in any convenient buffer to a known volume to assist in qualitative or quantitative detection of the target bacterial cells in the sample.

Detecting fluorescence may include exciting a fluorescent dye (e.g., the fluorogenic solvatochromic dye of the conjugate) with one or more lasers, and subsequently detecting fluorescence emission from the dye using one or more optical detectors. In some embodiments, the methods further include counting, sorting, or counting and sorting a labeled microorganism. The solvatochromic dyes may be detected and uniquely identified by exposing them to excitation light and measuring the fluorescence produced in one or more detection channels, as desired. The excitation light may be from one or more light sources and may be either narrow or broadband. Examples of excitation light sources include lasers, light emitting diodes, and lamps, including mercury or xenon lamps, arc lamps, a flash lamp, incandescent bulb or any other light source suitable for excitation of fluorescence. Fluorescence emitted in detection channels used to identify the solvatochromic dye and components associated therewith may be measured following excitation with a single light source, or may be measured separately following excitation with distinct light sources. The solvatochromic dyes may be selected such that the dyes are excitable by the excitation light sources of interest that are used. Any convenient methods of microscopy can be utilized in the detecting step of the subject methods.

In some embodiments, detection involves a qualitative determination of the presence of target bacterial cells in the sample. In certain instances, the target bacterial cell is one that has infected a cell of the host. A qualitative determination can include observing a characteristic fluorescence from components of an infected cell, e.g., from the cell wall of a target bacterial cell. In some cases, detection can involve a quantitative determination of the number of target bacterial cells in the sample. A quantitative determination can include counting the number of cells (e.g., per sample, per unit volume, mL) that are positively fluorescent versus a negative control cell. In certain instances, a negative control cell may exhibit some minor background fluorescence that can be easily distinguished from that of a labelled target cell.

Monitoring Bacterial Cells During Treatment for Infection

As used herein, the terms "treatment," "treating," and the like, refer to obtaining a desired pharmacologic and/or physiologic effect. The effect may be prophylactic in terms of completely or partially preventing a disease (e.g., mycobacterial infection) or symptom thereof and/or may be therapeutic in terms of a partial or complete cure for a disease (e.g., mycobacterial infection) and/or adverse effect attributable to the disease (e.g., mycobacterial infection). As used herein, the terms "treating," "treatment," "therapeutic," or "therapy" do not necessarily mean total cure or abolition of the disease or condition. Any alleviation of any undesired signs or symptoms of a disease or condition, to any extent can be considered treatment and/or therapy. Furthermore, treatment may include acts that may worsen the patient's overall feeling of well-being or appearance. "Treatment," as used herein, covers any treatment of a disease in a mammal, particularly in a human, and includes: (a) preventing the disease (e.g., mycobacterial infection) from occurring in a subject which may be predisposed to the disease (e.g., mycobacterial infection) but has not yet been diagnosed as having it; (b) inhibiting the disease (e.g., mycobacterial infection), i.e., arresting its development; and (c) relieving the disease (e.g., TB infection), i.e., causing regression of the disease (e.g., mycobacterial infection).

Aspects of the present disclosure include methods of detecting and monitoring target bacterial cells in a multitude of samples taken at intervals from a subject during treatment or prevention of an infection of the subject. In some embodiments, the subject is infected with a mycobacteria (e.g., as described herein, such as *Mycobacterium tuberculosis*). Such individuals may be tested at one or a plurality of time points, including, without limitation, at the time of diagnosis, prior to, during and/or after anti-infective treatment; and at various time points to monitor disease progression. As such, aspects of the method include collecting one or more samples from a subject suffering from a bacterial infection before, during and/or after treatment (e.g., administration of an anti-infective agent to the subject). In some cases, sampling the subject before treatment to detect target bacteria according to the subject methods further includes diagnosis of an infection in the subject. For example, in some cases, a biological sample is obtained from an individual at a first time point, and target cells are detected in the biological sample; a biological sample is obtained from the individual at a second time point, and target cells are detected in the biological sample; and the number of target cells detected in the biological sample from the second time point is compared to the number of target cells detected in the biological sample from the first time point, where the second time point is after the first time point (e.g., one hour to 4 hours, 4 hours to 8 hours, 8 hours to 24 hours, 1 day to 1 week, 1 week to 1 month, 1 month to 6 months, 6 months to 1 year, or more than 1 year, after the first time point).

Aspects of the subject method include quantitating the target metabolically active bacterial cells in the sample, so that the levels of the cells over time can be monitored to assess the effectiveness of the treatment method. As such, the collection of the sample can be performed before treatment and at one or more time points during treatment or after treatment. Depending on the results of the monitoring, the anti-infective treatment method can be adjusted to provide for a desirable therapeutic outcome, e.g., the treatment dosage or regimen can be altered according to a change in the amount of target metabolically active bacterial cells that is quantitated in the sample over time.

In some embodiments, the method includes administering to a subject in need thereof a therapeutically effective amount of anti-infective agent, e.g., an anti-mycotic agent, as guided by the findings of the treatment monitoring methods according to the embodiments of this application. In certain instances, the subject is suffering from an HIV infection in addition to the target bacterial infection, and exhibits relatively low numbers of target bacterial cells in samples. The subject methods provide for detection of target cells in such samples.

Determining Bacteria's Drug Sensitivity/Resistance

Aspects of the subject methods include rapid detection of drug-resistant bacteria. Accordingly, in some embodiments, the subject conjugates can be used to discriminate bacteria that are resistant to a treatment, from bacteria that are successfully targeted by the treatment. In many such embodiments, a sample of interest is split into a multitude of samples according to the number of available treatment plans. Next, each of the new samples is treated according to its assigned treatment plan, while being subjected to the conjugate probe at predetermined intervals. In many embodiments, the sample resistant to treatment and, thus, maintaining the vitality of its bacteria, will continue to uptake the conjugate and produce a detectable signal. In contrast, the sample sensitive to the assigned treatment will not be able to produce a measurable signal, as its ability to metabolically uptake the conjugate is compromised in the absence of live bacteria. The described herein method of testing for drug resistance is a significant improvement, including in speed, over the current practices for determining drug susceptibility of, for example, clinical Mtb isolates, which typically rely on PCR-based methods (testing for known resistance genes) or lengthy (up to 6 weeks) culturing of samples in the presence of drugs. In stark contrast, in some examples studying mycobacteria resistance to TB drug cocktail according to the embodiments of the instant application, it was found that DMN-Tre labeling is affected by drug action within hours, and the results of such a microscopy test could, therefore, be available on the same day as sample collection.

In some cases, the subject methods include detecting and/or identifying drug-resistant bacterial cells, e.g., in a sample from a subject undergoing treatment. The treatment regimen or type of anti-infective agent can be adjusted according to the type and number of drug-resistant bacteria that are detected or identified. As such, the subject methods can be performed in conjunction with a method of treating an infective condition.

Therapeutic Utilities

The subject compositions and methods can be employed in a variety of diagnostic, research and therapeutic applications. The subject methods compositions and methods find use in any applications where the identification of a target bacterial cell is of interest, such as target bacterial cells that are capable of metabolically labelling and uptake of the subject carbohydrate-dye conjugates.

Diagnostic applications of interest include, but are not limited to, practicing the subject methods of detection to provide diagnosis of an infection. Therapeutic applications of interest include, but are not limited to, monitoring the progress of anti-infective treatment, prior to, during and/or after anti-infective treatment, and selecting and/or adjusting a desired treatment regimen or type of anti-infective agent based on the detection of drug-resistant bacterial cells. In some embodiments, the subject methods find use in the direct detection of pathogenic bacteria, such as Mtb, in the sample of a patient, or the monitoring of pathogenic bacteria levels in samples of a patient being treated for an infection. In other embodiments, the subject methods find use in determining the sensitivity of a target bacteria or organism to a panel of possible therapeutics.

EXAMPLARY EMBODIMENTS

The following examples are put forth to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal(ly); s.c., subcutaneous(ly); and the like.

The following examples, demonstrating various features and advantages of the mycobacteria detection methods according to the embodiments of the present invention, primarily rely on trehalose conjugated to the solvatochromic dye 4-N,N-dimethylamino-1,8-naphthalimide (DMN), a reagent termed here as "DMN-Tre." In many embodiments, DMN-Tre is metabolically incorporated into mycomembranes where it undergoes a dramatic enhancement in fluorescence that enables detection of mycobacteria in TB patient sputum samples in under an hour (according to the process schematically depicted in FIG. 5). Unlike the classic ZN and auramine stains, DMN-Tre selectively labels live Mtb cells and this labeling is inhibited by exposure to frontline TB drugs. This operationally simple method requires a single incubation step, with no washes, and may, therefore, powerfully complement current methods for TB diagnosis at the point of care.

Example 1. Detection of Mycobacteria with DMN-Tre Conjugate

Figure 8:
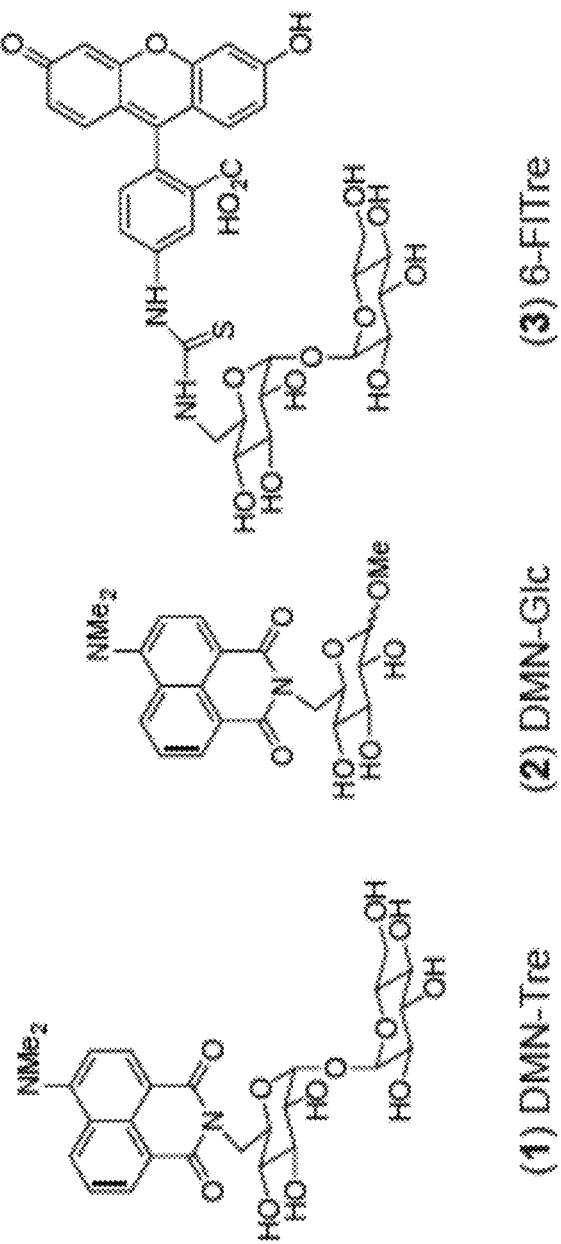
FIG. 8 shows chemical composition and structure of 4-N,N-dimethylamino-1,8-naphthalimide-conjugated trehalose (DMN-Tre), as well as and control compounds DMN-glucose (DMN-Glc) and 6-fluorescein-trehalose (6-FITre), in accordance with embodiments of the application.
Figure 9A:
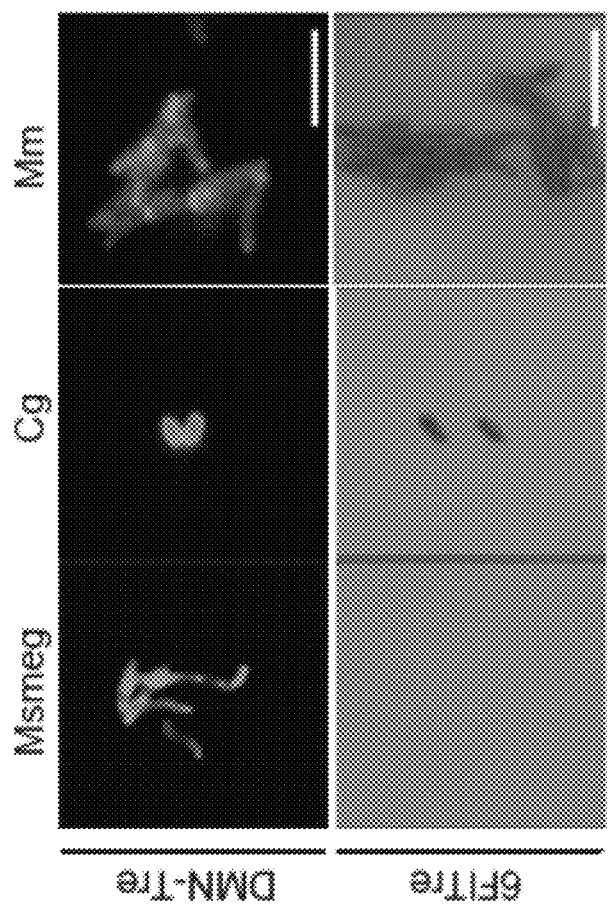
FIG. 9A provides results of no-wash imaging of various mycobacteria treated with either DMN-Tre or its non-fluorogenic analog 6-FITre in accordance with embodiments of the application.
Figure 9B:
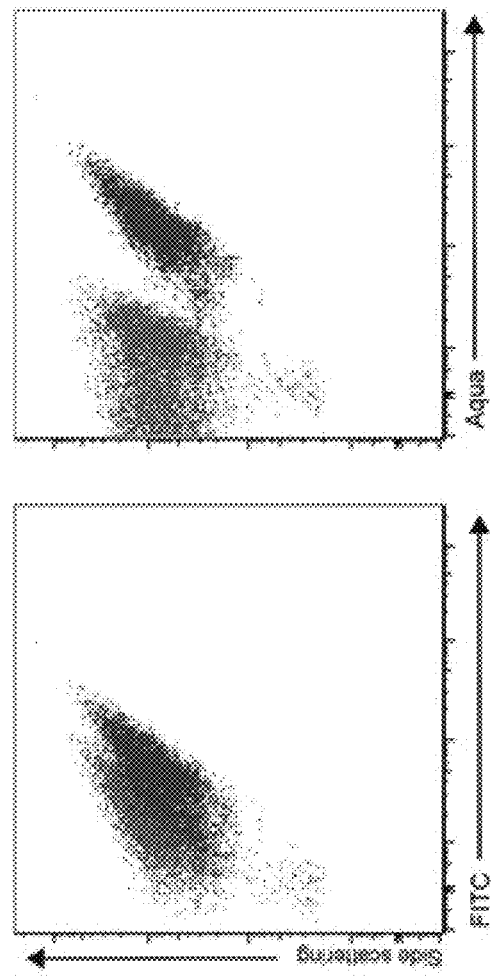
FIG. 9B illustrates optimization of DMN-Tre detection via fluorescence filters customization in accordance with embodiments of the application.

First, DMN-Tre conjugate was synthesized, as well as two control compounds, DMN-glucose (DMN-Glc) and a non-fluorogenic analog 6-fluorescein-trehalose (6-FITre), as depicted in FIG. 8, wherein these structures are labeled (1), (2), and (3) correspondingly. After confirming that DMN-Tre's fluorescence properties were similar to those reported for the free dye, including a ~700-fold enhancement in fluorescence intensity when dissolved in organic solvent versus water, several strains from the Actinobacteria phylum were tested to evaluate DMN-Tre's ability to label bacteria bearing mycomembranes. Specifically, *Mycobacterium smegmatis* (Msmeg), *Corynebacterium glutamicum* (Cg), and *Mycobacterium marinum* (Mm), each in exponential growth phase, were incubated with either 100 µM DMN-Tre or its non-fluorogenic analog 6-FITre for 1, 2 and 6 hours, respectively, then imaged without washing. Bright fluorescence labeling of all three species was observed with DMN-Tre, with no discernible background fluorescence derived from free DMN-Tre in the surrounding solution (FIG. 9A). By contrast, cells labeled with 6-FITre were obscured by fluorescence of the probe in the surrounding solution. Extensive washing was required to remove nonspecifically bound 6-FITre from cells and their debris, rendering specifically labeled cells difficult to discern compared to those labeled with DMN-Tre. These images were acquired by using standard FITC/GFP filter sets, but an even brighter image can be obtained by excitation at 405 nm, closer to DMN's excitation maximum. To this end, FIG. 9B shows flow cytometry analysis of Msmeg cells treated with 100 µM DMN-Tre for 1 h using the FITC/GFP filter sets (488 nm excitation, 530 nm emission) or Aqua Amine filter sets (405 nm excitation, 512 nm emission). As seen from this figure, labeled Msmeg cells (blue) display higher fluorescence signal over control samples (red) when excited at wavelengths closer to 400 nm.

Figure 10:
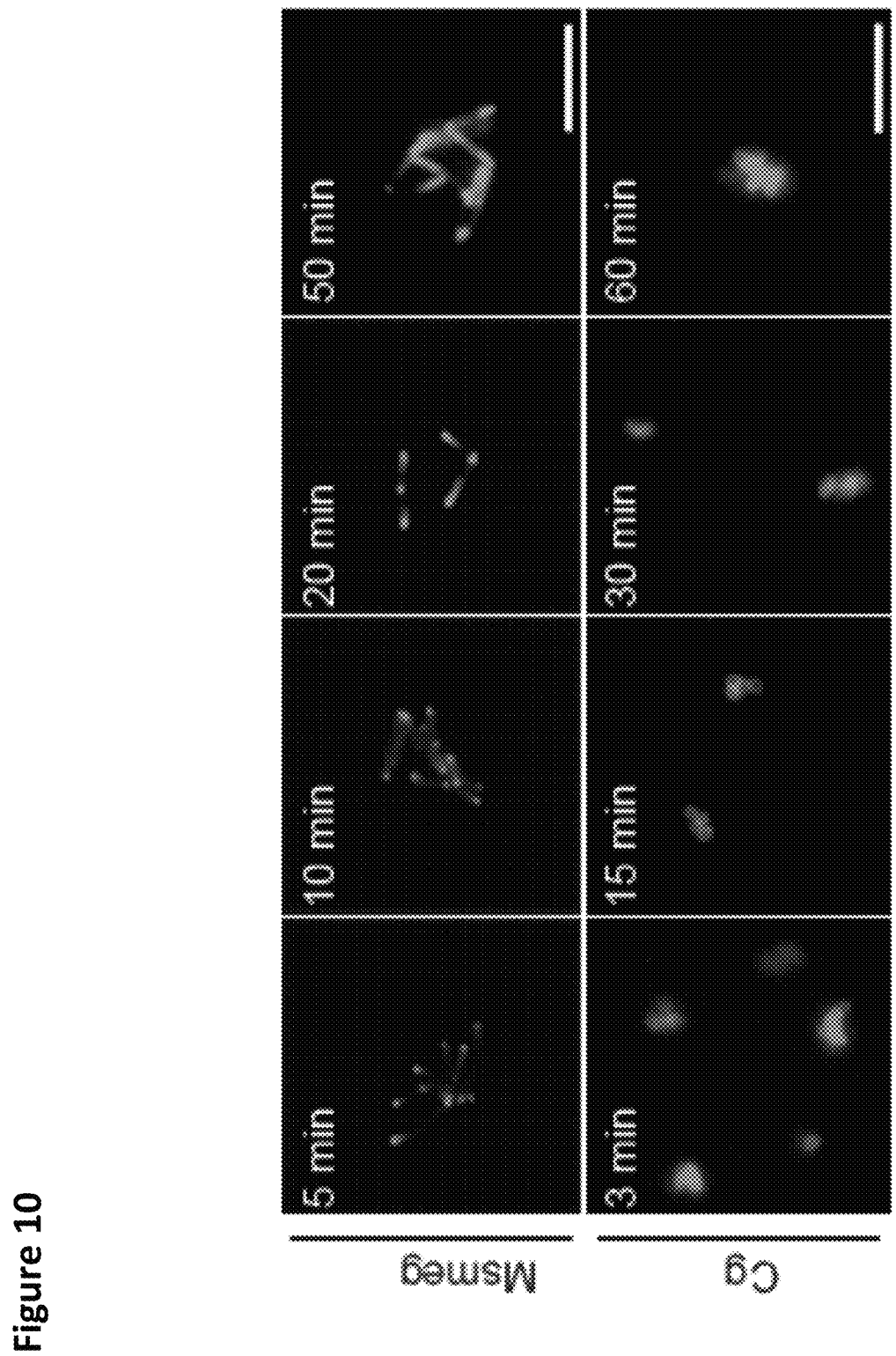
FIG. 10 demonstrates results of fluorescent labeling of various mycobacteria by DMN-Tre as a function of time, in accordance with embodiments of the application.

A time course to determine the labeling kinetics was also performed. Msmeg and Cg harvested during their exponential growth phase were incubated as above and imaged at various time points. As shown in FIG. 10, labeling was already visible at the first time point—5 min for Msmeg and 3 min for Cg. While Cg displayed even cell surface labeling by the earliest time point analyzed, Msmeg showed fluorescence only at the polar regions, consistent with the known polar growth in mycobacterial species. This signal spread across the cell length so that by 1 hour Msmeg cells were uniformly labeled. These experiments demonstrate unprecedented speed of the mycobacteria detection methods conducted according to the embodiments of the present application.

Example 2. DMN-Tre Conjugate Selectivity for Mycobacteria

Figure 11A:
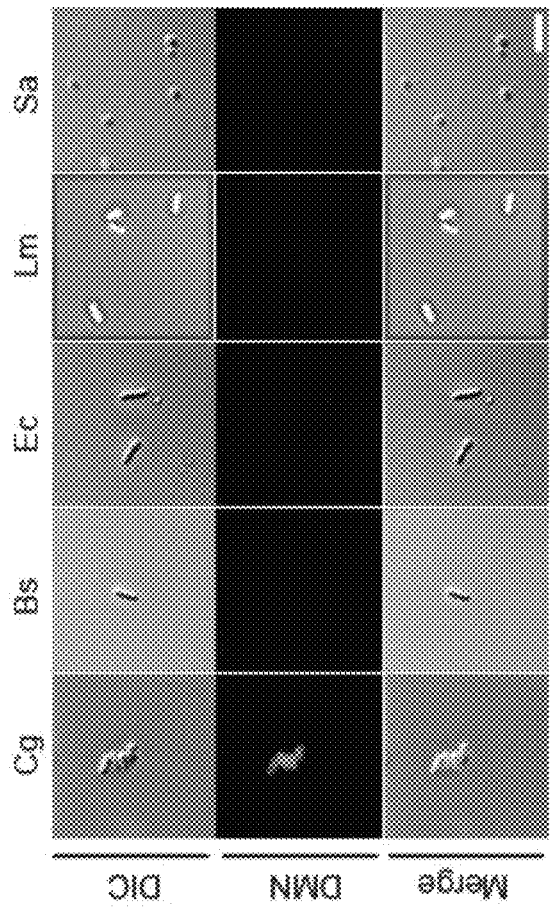
FIGS. 11A and B demonstrate selectivity of DMN-Tre labeling for mycobacteria over gram-positive and gram-negative bacteria in accordance with embodiments of the application.
Figure 11B:
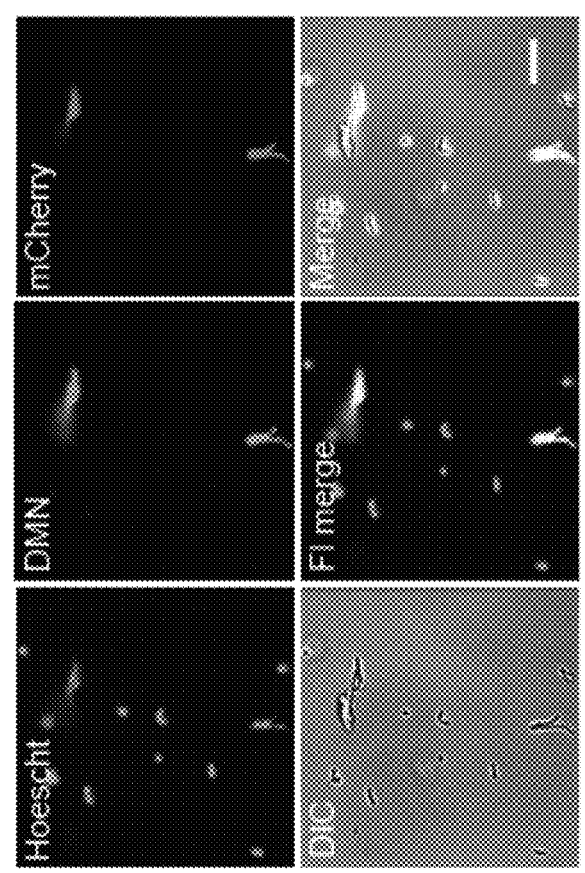

DMN-Tre's potential as a diagnostic tool, including for diagnosis of TB, depends on its selectivity for mycobacteria among other bacterial species. Therefore, to test its selectivity, canonical gram-negative and gram-positive organisms (*Bacillus subtilis* (Bs), *Escherichia coli* (Ec), *Listeria monocytogenes* (Lm), and *Staphylococcus aureus* (Sa)) were incubated with DMN-Tre. FIG. 11A provides the results of this test, wherein, without washing, none of the non-mycobacterial strains show any detectable fluorescence labeling by the conjugate ("DMN" row), whilst the bacterial presence is confirmed in all the test samples by optical microscopy ("DIC" row), and the overall labeling results are further confirmed by the overlay of both detection methods used ("Merge" row). In the same experiment, mycobacteria Cg labeled brightly with DMN-Tre. This specificity is striking, given the important role that free trehalose plays as an osmo- and thermoprotectant in these other bacterial species. Further, mycobacteria Msmeg expressing mCherry was combined with the gram-negative and -positive bacteria in a 1:10 mycobacteria/other bacteria ratio and incubated the mixture with Hoechst dye (to detect all present species), a DNA stain, and DMN-Tre (to detect mycobacteria only) for one hour. Bright, specific, DMN-Tre labeling of only Msmeg cells was observed (FIG. 11B), proving DMN-Tre conjugate high specificity for detection of mycobacteria.

Example 3. Metabolic Nature of DMN-Tre Conjugate Uptake by Mycobacteria

Figure 12:
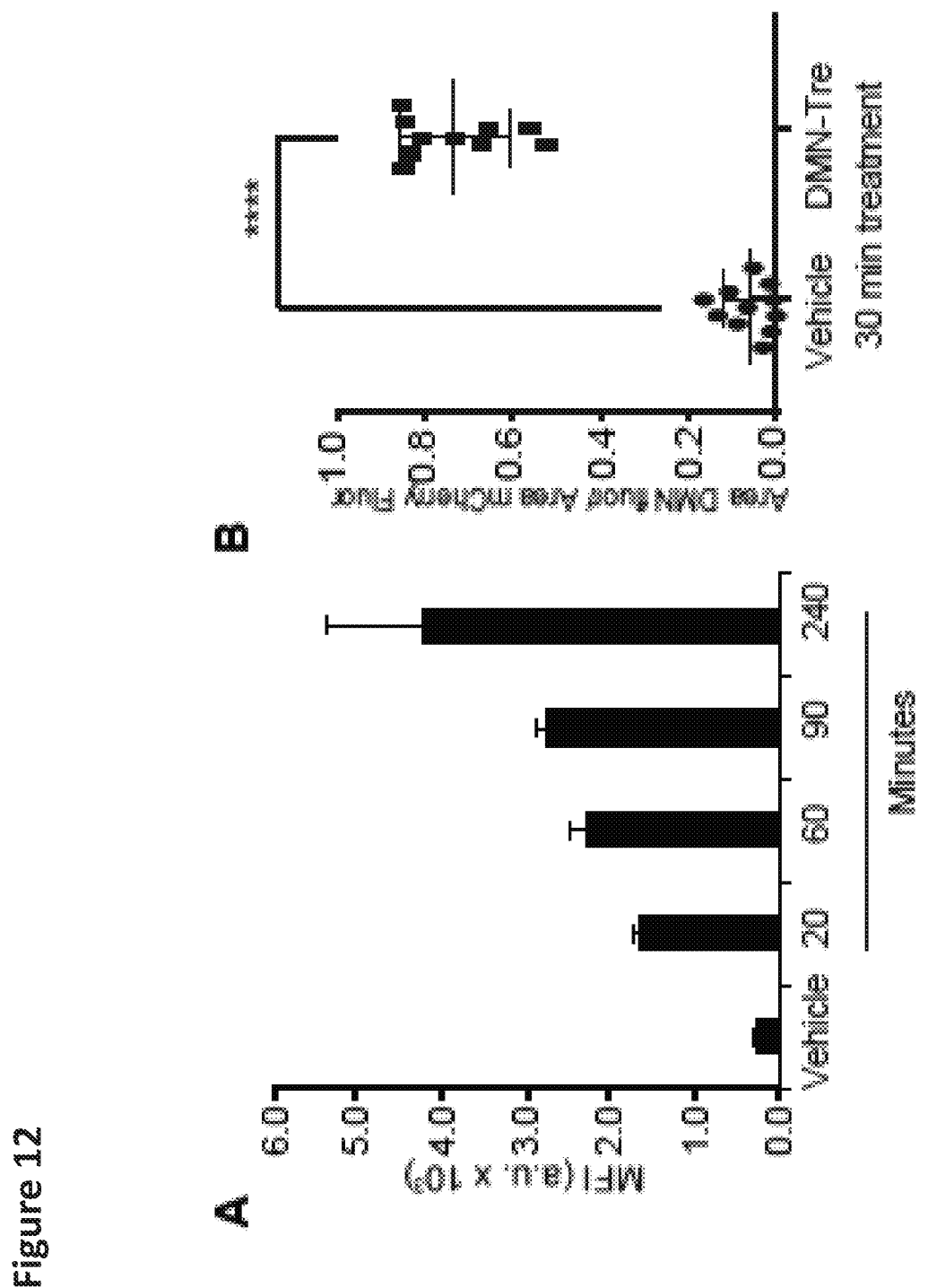
FIGS. 12A-F provide data in support of metabolic nature of DMN-Tre conjugate uptake by mycobacteria in accordance with embodiments of the application.
Figure 12:
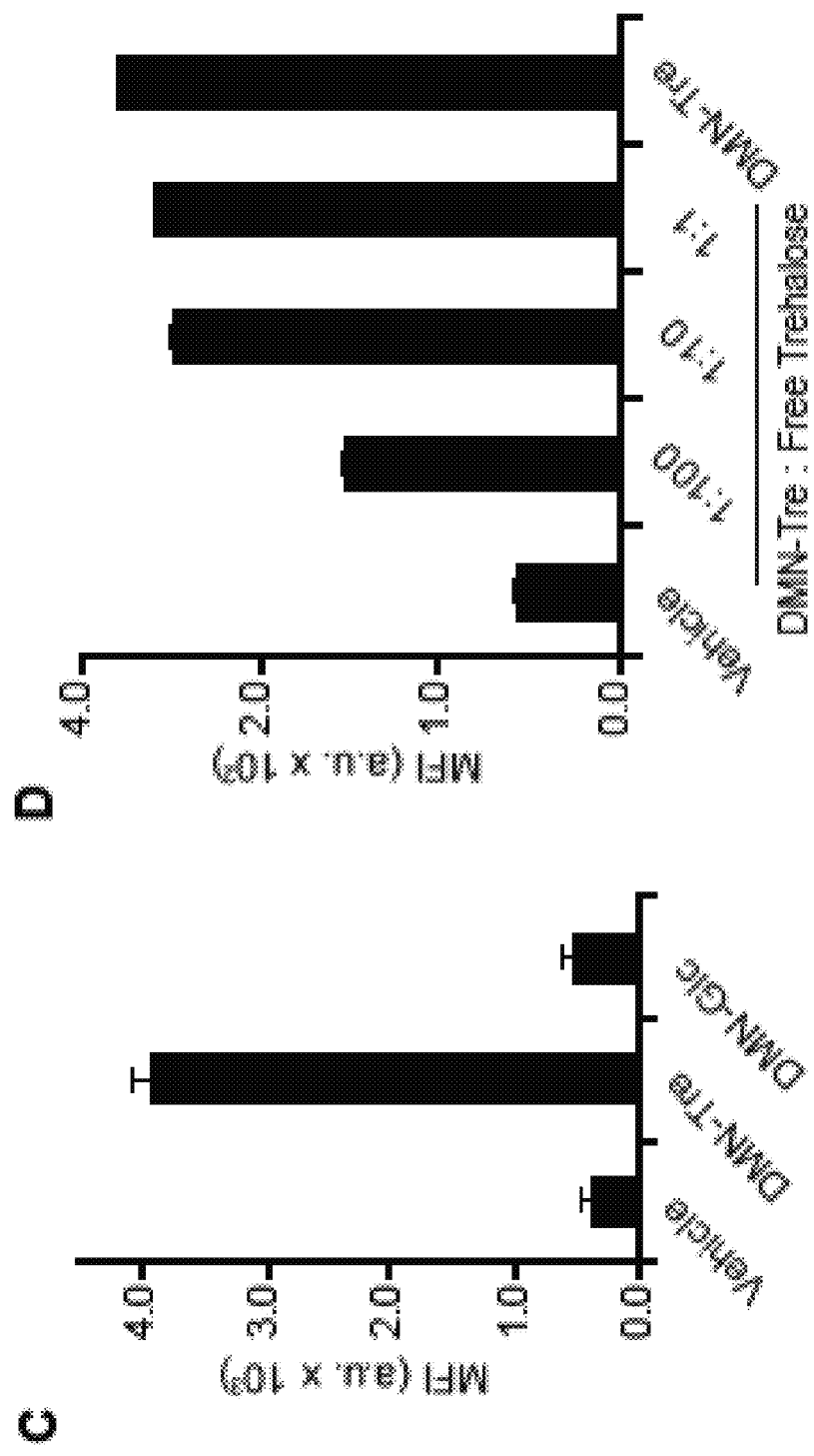
Figure 12:
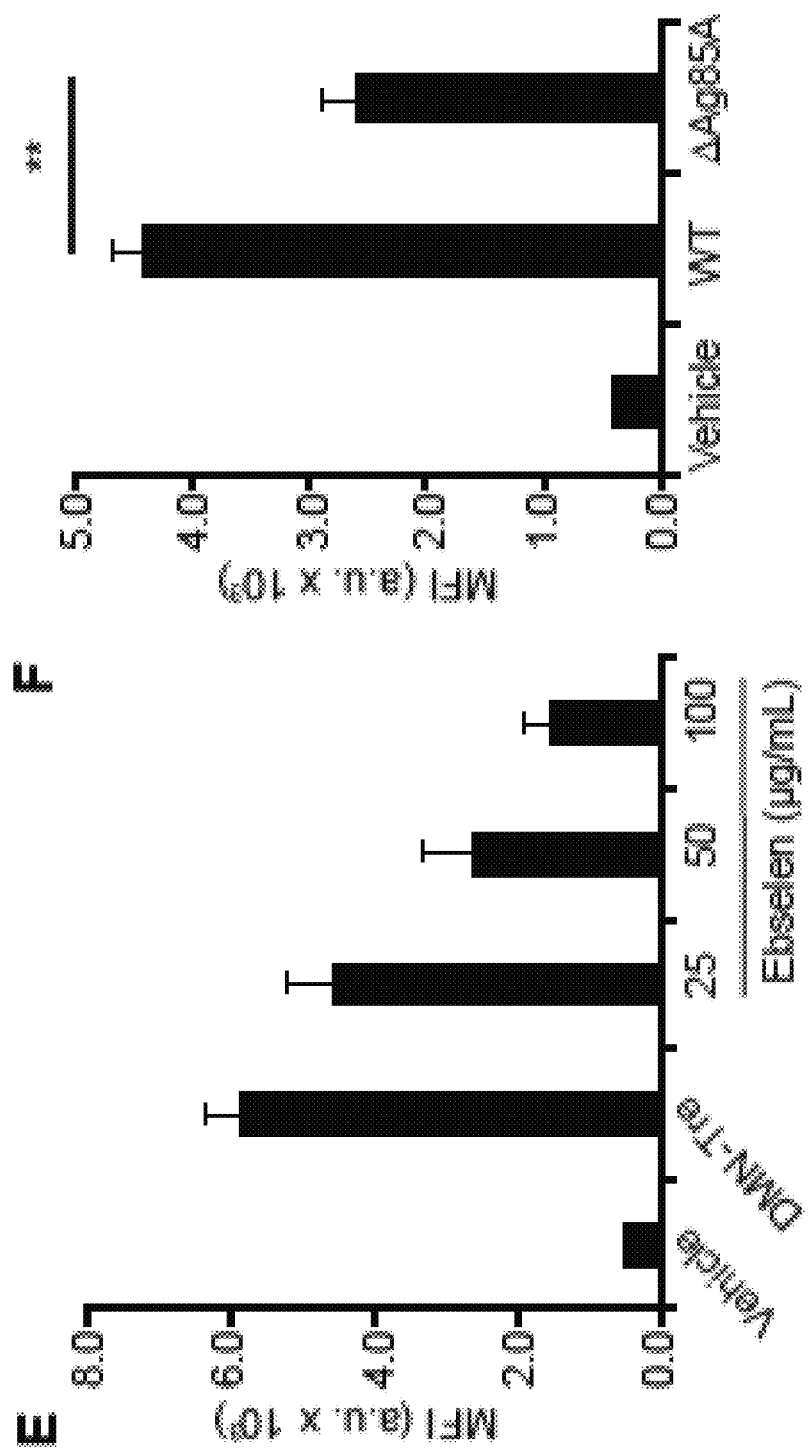

A series of experiments were performed to confirm that DMN-Tre labeling results from metabolic conversion to trehalose mycolates within the mycomembrane rather than nonspecific insertion into the mycomembrane. First, flow cytometry was used to confirm that Msmeg exhibit significant fluorescence over background within 20 min (FIG. 12A) and that >70% of cells are labeled within 30 minutes (FIG. 12B). DMN-Glc, which possesses the same dye but installed on glucose, did not label Msmeg, suggesting that the trehalose scaffold is key for the observed fluorescence signal from DMN-Tre treatment (FIG. 12C). As well, DMN-Tre labeling was reduced in the presence of excess trehalose, suggesting competition in the same biosynthetic pathway (FIG. 12D). DMN-Tre labeling of a panel of Msmeg trehalose transporter mutants was also assessed and it was found that DMN-Tre incorporation was comparable to wild-type, suggesting that labeling occurs primarily through the Ag85 pathway, consistent with previous studies. Accordingly, the Ag85 inhibitor ebselen decreased DMN-Tre labeling of Msmeg cells in a dose-dependent manner (FIG. 12E) and Msmeg deficient in Ag85A, a component of the Ag85 complex, exhibited reduced labeling compared to wild-type (FIG. 12F). Lastly, purified glycolipids from DMN-Tre-labeled Cg were analyzed by TLC and mass spectrometry and only DMN-Tre monomycolates were detected as the labeled species. As well, loss of lipid tails from DMN-Tre-derived monomycolates by was observed tandem mass spectrometry.

Figure 13:
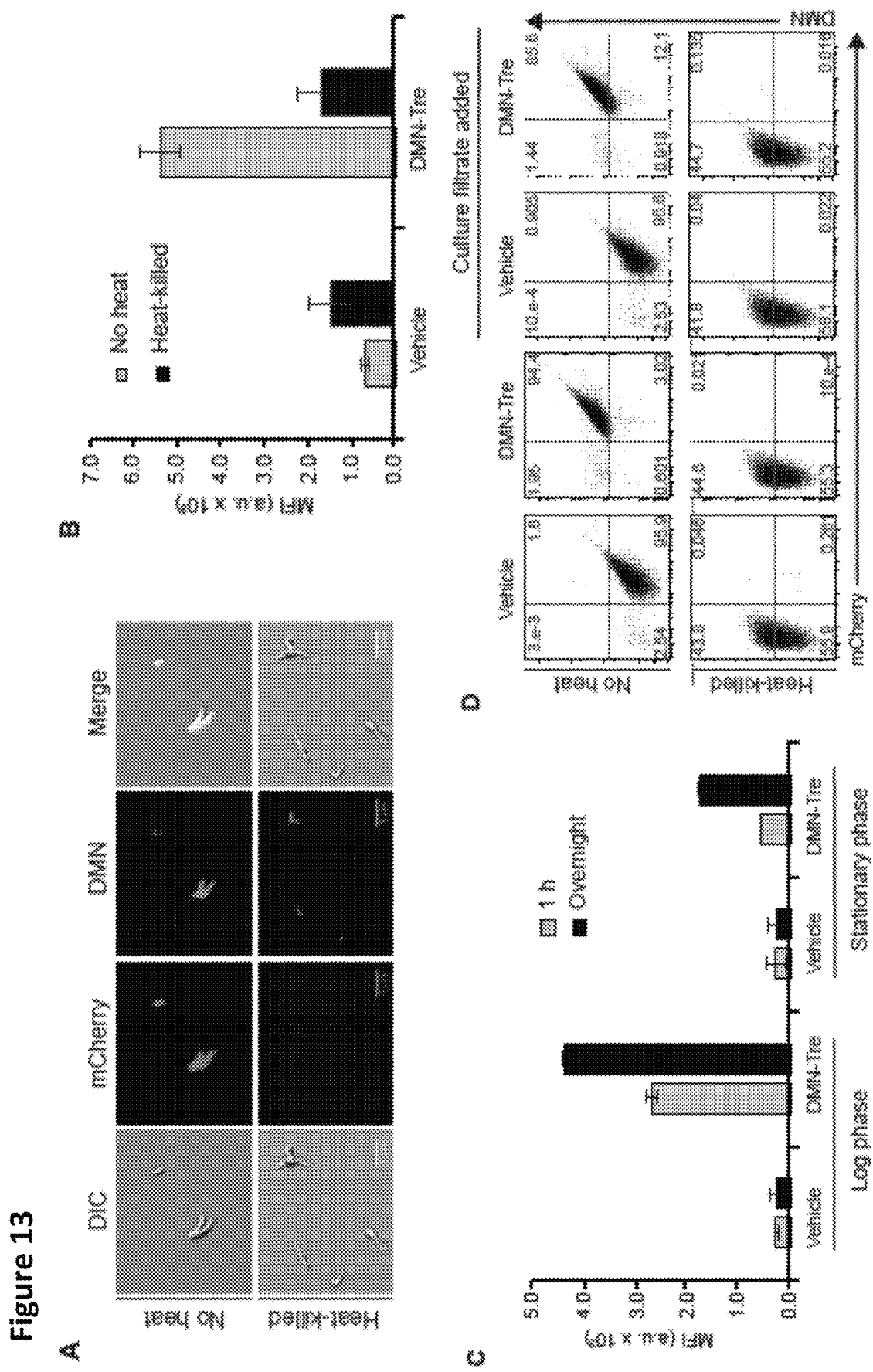
FIGS. 13A-D provide data in supports of the notion that DMN-Tre labeling is selective for live mycobacteria in accordance with embodiments of the application.

Current microscopy-based methods for TB diagnosis cannot distinguish live from dead mycobacteria. Given that DMN-Tre labeling appears to be of metabolic nature and depend on mycomembrane biosynthesis, it was hypothesized that the methods of the present disclosure would be specific for live bacteria. Indeed, labeling was abrogated by heat killing Msmeg (FIGS. 13A and 13B). By contrast, cultured Msmeg in stationary phase continue to label with DMN-Tre, albeit at lower intensity levels than Msmeg in log phase (FIG. 13C). An interesting question is whether active Ag85 protein released by live cells can cause mycomembrane labeling of nearby dead cells in the presence of DMN-Tre. To answer this question, the culture filtrates from live Msmeg were incubated in growth phase with heat-killed Msmeg cells in the presence of DMN-Tre and analyzed fluorescence of the dead cells by flow cytometry. As shown in FIG. 13D, no such trans-labeling was observed above the level of autofluorescence, suggesting that DMN-Tre labeling is cell autonomous.

Example 4. Use of DMN-Tre Conjugate in Drug Resistance Tests

Figure 14A:
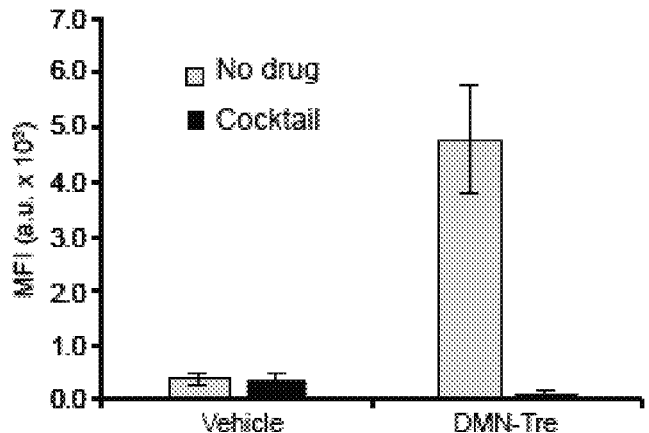
FIGS. 14A-C show that DMN-Tre labeling is inhibited by TB drugs and, therefore, can be used to test for drug resistance in accordance with embodiments of the application.
Figure 14B:
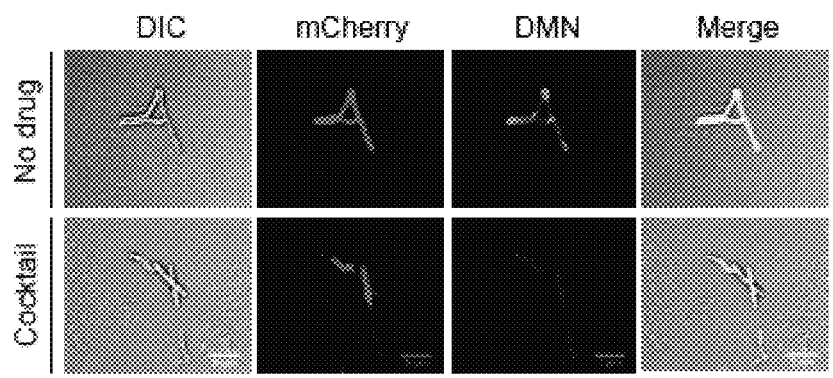
Figure 14C:
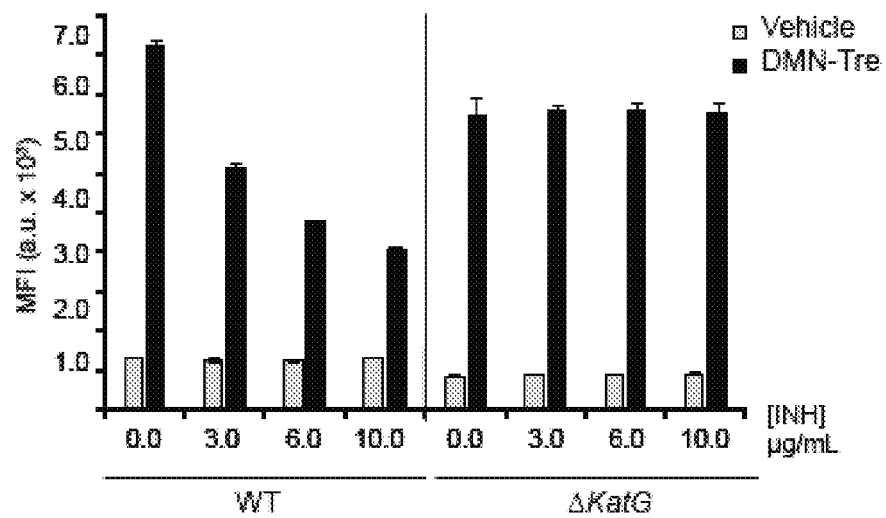

The effect of TB drug treatment on labeling was evaluated. To this end, Msmeg cells treated for 3 hours with a cocktail of ethambutol, rifampicin, isoniazid and SQ109, each at a dose at or above reported minimum inhibitory concentrations (MICs) to induce cell killing, lost all detectable labeling with DMN-Tre (FIGS. 14A and 14B). Since isoniazid is a prodrug that inhibits mycolic acid biosynthesis after activation by the enzyme KatG, it was hypothesized that a ΔkatG mutant would be resistant to isoniazid's effects on DMN-Tre labeling. As shown in FIG. 14C, DMN-Tre labeling of ΔkatG mutant of Msmeg, but not wild-type Msmeg, was unaffected by isoniazid treatment.

Example 5. Detection of Pathogenic Mtb with DMN-Tre Conjugate

Figure 15A:
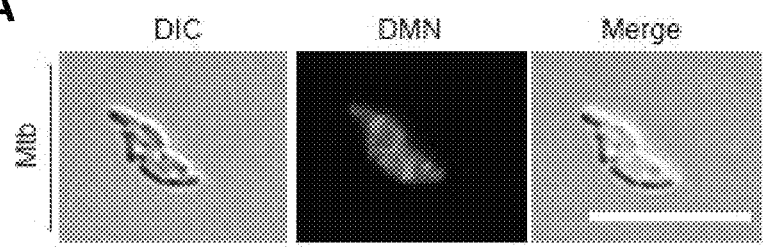
FIG. 15A provides results of no-wash imaging of M. tuberculosis (Mtb) treated with DMN-Tre, while FIGS. 15B and C demonstrate that DMN-Tre labeling of M. tuberculosis (Mtb) is inhibited by TB drug cocktail in accordance with embodiments of the application.
Figure 15B:
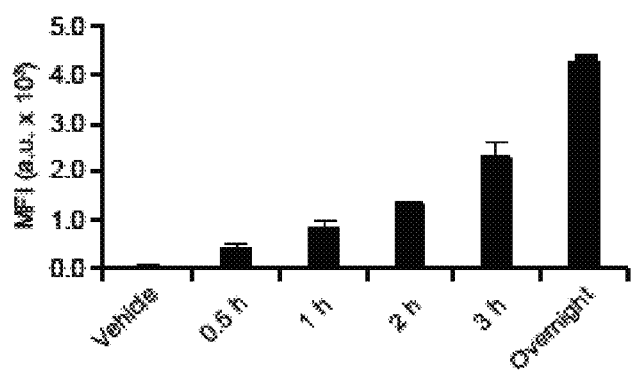
FIG. 15D demonstrates that auramine staining according to prior art is not inhibited by TB drug cocktail.
Figure 15C:
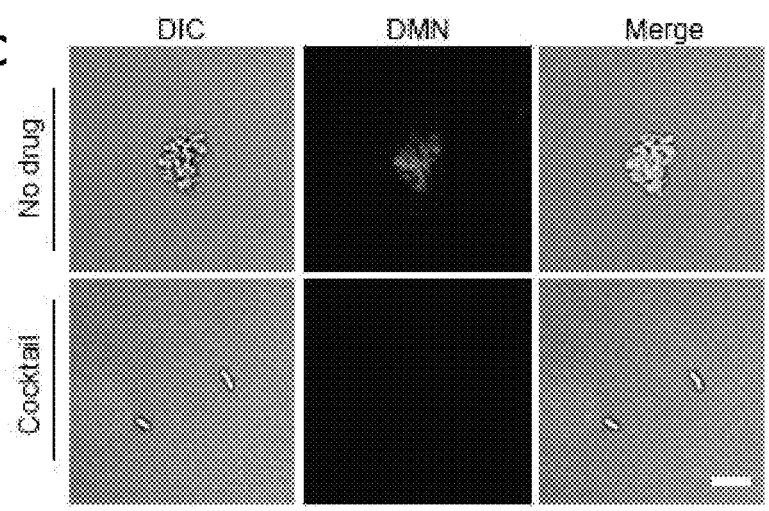
Figure 15D:
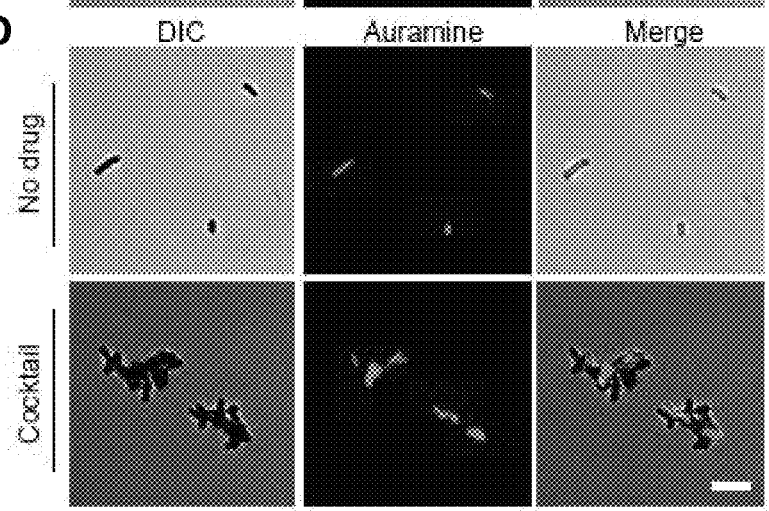

Having established the parameters and mechanistic basis of DMN-Tre labeling with Msmeg, attention was focused on studies with pathogenic Mtb. Liquid cultures of Mtb (H37Rv) were visibly labeled with DMN-Tre (FIG. 15A) with >65% of cells labeled within 30 minutes, and labeling continued to intensify overnight (~16 h; FIG. 15B). The limit of detection in this assay appeared to be on par with that of auramine stain (~$10^4$ CFU/mL). However, given that DMN-Tre detection of Mtb in sputum does not require a heat-fix step, it is possible to enrich mycobacteria and thereby maximize detection by microscopy. For instance, depending on the user's ability and equipment capability, it is possible to concentrate down the specimen to a small volume, which can then be collected onto a filter membrane by passing them through a syringe. Subsequently, DMN-Tre can be added directly onto the membrane followed by imaging. Following this method, it has been determined that the limit of detection could be as low as <50 CFU/mL which would be a significant improvement over the auramine stain. Moreover, Similar to Msmeg, treatment of Mtb cells with the drug cocktail for 3 hours prior to incubation with DMN-Tre led to a significant reduction in cell viability, which was reflected in DMN-Tre labeling (FIG. 15C). In contrast, labeling with the commercial auramine-based mycobacterial staining dye (Fluorescent Stain Kit for Mycobacteria, Sigma-Aldrich, 05151) was unaffected by prior drug cocktail treatment (FIG. 15D).

Figure 16:
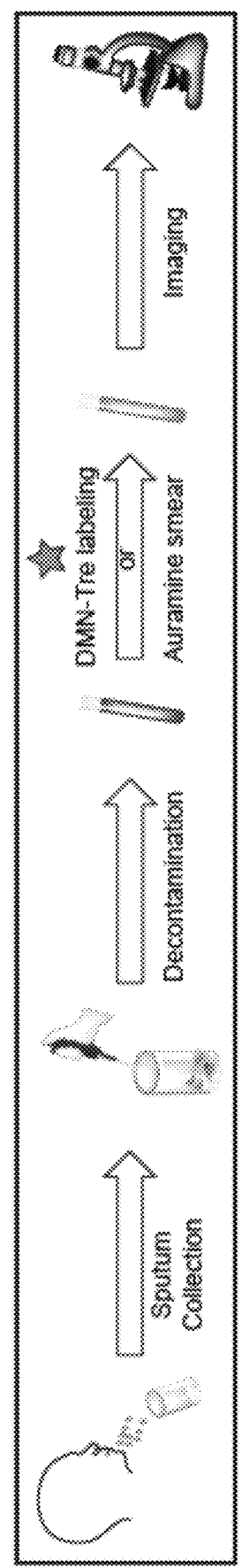
FIG. 16 Illustrates a protocol for sputum sample labeling with DMN-Tre in accordance with embodiments of the application.
Figure 17:
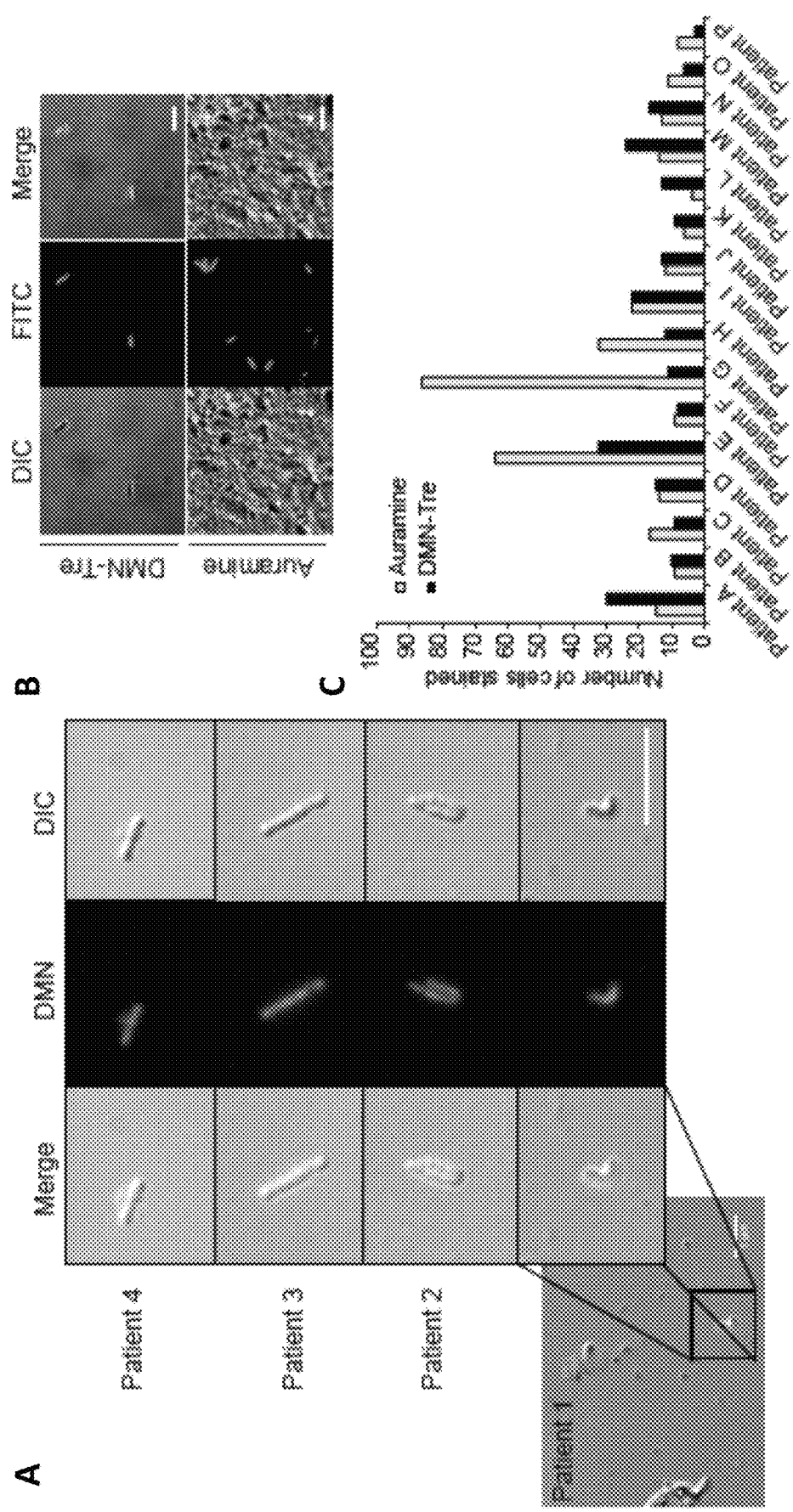
FIGS. 17A-D demonstrate DMN-Tre detection of Mtb in sputum samples from TB-positive patients in accordance with embodiments of the application.
Figure 17D:
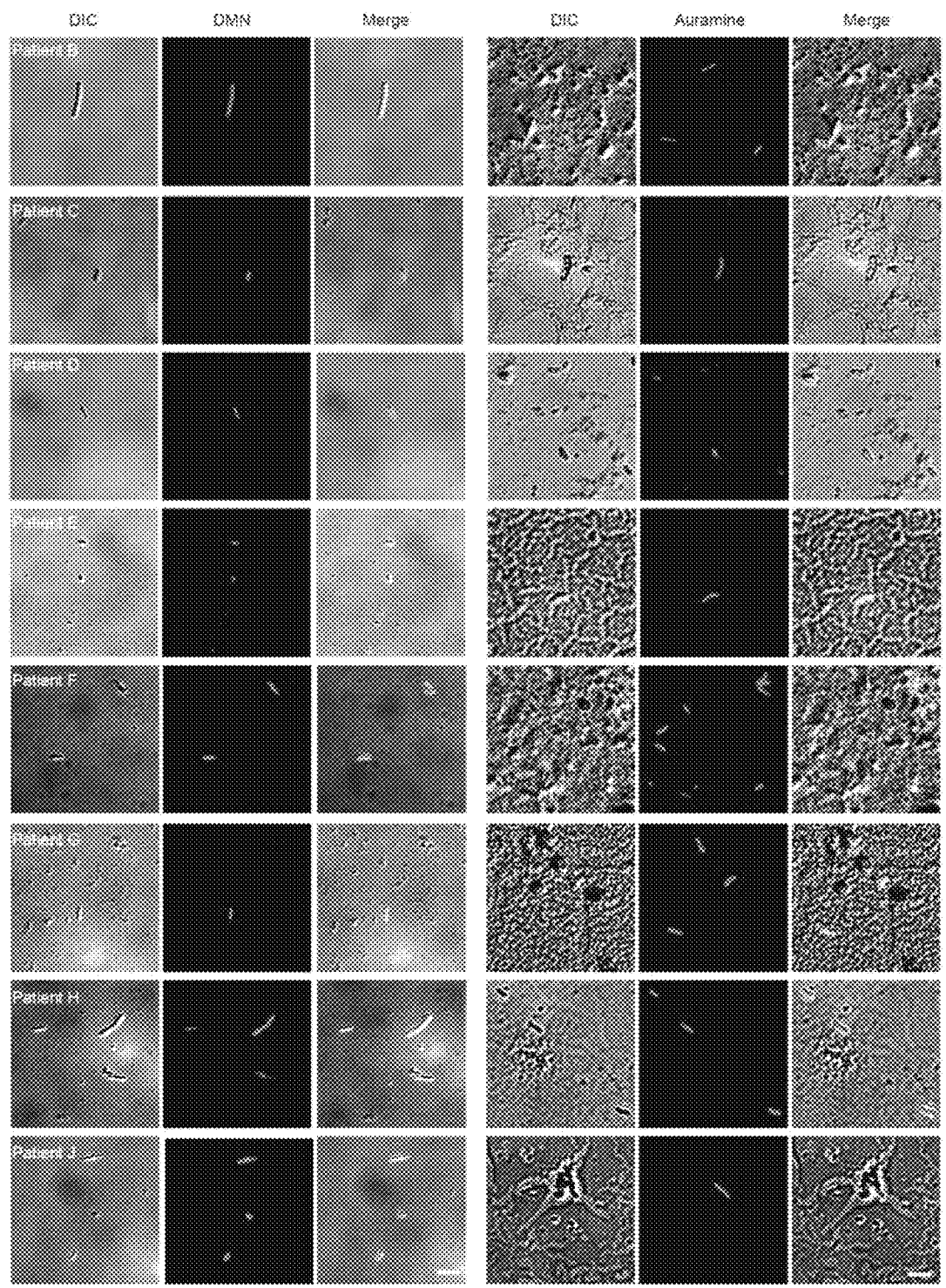

Furthermore, to gain insight into the potential clinical utility of DMN-Tre, detection of Mtb cells in TB-positive patient sputum samples was attempted. Sputum samples from 16 treatment-naïve patients, who were TB positive, were obtained by either smear microscopy or GeneXpert. The samples were decontaminated using a standard N-acetyl-L-cysteine-sodium hydroxide (NALC/NaOH) treatment and then incubated with DMN-Tre (FIG. 16). Initially, sputum samples were imaged after a 2-hour incubation with DMN-Tre and fluorescent Mtb cells were readily visible in all samples (FIGS. 17A and D). Subsequently, a small-scale smear test comparison was performed between DMN-Tre and Auramine O stain (FIGS. 17B-D). For the sixteen sputum samples collected, each was split in half, and the samples were incubated with DMN-Tre for 30 minutes or smeared with Auramine O stain (following standard kit protocol). Mtb cells were detected in these samples with both reagents, although the no-wash DMN-Tre procedure was considerably simpler than the multi-step auramine procedure. For each reagent, the number of visibly stained cells was quantified over 8 fields of view per sample for all 16 sputum samples (FIG. 17C). DMN-Tre performed similarly to Auramine O in terms of Mtb cells detected in sputum from these patients prior to drug treatment.

In summary, DMN-Tre labeling appears to be unique in its combination of attributes. Unlike classic methods for detecting Mtb cells by microscopy, DMN-Tre labeling specifically targets a pathway in mycomembrane biosynthesis and therefore reports both on bacterial identity and vitality. The unique solvatochromic property of DMN-Tre enables rapid Mtb imaging without cumbersome washing steps. When combined, these features enable the detection of live Mtb in samples as complex as patient sputum.

DMN-Tre's unique mode of fluorescence activation allows for an operationally simple procedure—a single incubation step. Notably, it was found that DMN-Tre is very stable on the bench or in shipping containers for weeks at room temperature, and even in aqueous solution at 37° C. Thus, the DMN-Tre labeling procedure may translate well both to research and clinical applications in low-resource environments.

Experimental Materials and Methods

Metabolic Labeling of Bacteria with DMN-Tre, DMN-Glc or 6-FlTre

Cultures of *M. smegmatis* (Msmeg) or mutants were made by inoculation of a single colony from an agar plate into 1 milliliter (mL) 7H9 liquid medium supplemented with 10% (v/v) oleate-albumin-dextrose-catalase enrichment (BBL Middlebrook OADC, catalog no. 212351), 0.5% (v/v) glycerol, and 0.05% (w/v) Tween 80 (Sigma, P1754) with or without antibiotic (if necessary) in a 5-mL culture tube (FisherSci, 14-959-11B). Cultures of *C. glutamicum* (Cg), *B. subtilis* (Bs), *E. coli* (Ec), *L. monocytogenes* (Lm) and *S. aureus* (Sa) were generated by inoculation of a single colony from an agar plate into 1 mL Luria Broth (Invitrogen, 12795-084) liquid medium in a 5-mL culture tube. Cultures of M. tuberculosis (Mtb) were made by inoculation of a 1-mL frozen stock into 50 mL Middlebrook 7H9 liquid medium supplemented with 10% (v/v) oleate-albumin-dextrose-catalase enrichment (BBL Middlebrook OADC, 212351), 0.5% (v/v) glycerol, and 0.05% (w/v) Tween 80 (Sigma, P1754) in a roller bottle or a tissue culture flask. Cultures were grown to $OD_{600}$=0.5 to begin experiments. Bacterial cultures were mixed with DMN-Tre (FIG. 1B, 1) or DMN-Glc (2) or 6-FITre (3) at a final concentration of 100 μM in 7H9 medium and incubated at 37° C. shaking or rolling for an additional one doubling time (unless otherwise specified). Vehicle controls were obtained from cells treated in an identical fashion in the absence of fluorescent probes. For Mtb, labeled cells were harvested by centrifugation (10 min, 3,000×g) then fixed in an equal volume of 2.5% glutaraldehyde. The cells were incubated at room temperature for 1 h, with occasional rotation of the tube to ensure sterilization of all internal surfaces prior to fluorescence analysis.

Flow Cytometry

Following metabolic labeling (and after fixation for Mtb cells), cells were harvested by centrifugation (3 min, 3,300× g), washed (2×500 microliter (μL) PBS) and resuspended in 300 μL PBS. Fluorescence measurements were taken in 5-mL culture tubes (FisherSci, 14-959A) suitable for flow cytometry. Data collection was performed on a BD LSR II.UV instrument in the shared FACS Facility at Stanford University (NIH S10 Shared Instrument Grant (S10RR027431-01)). This instrument is equipped with a 405 nm violet laser and 488 nm blue laser (for Aqua Amine and FITC channels, respectively) both used to detect DMN-Tre fluorescence. Fluorescence data was obtained for 100,000 cells per sample and processed using FlowJo (Tree Star) software. Experiments were conducted in three biological replicates.

Fluorescence Microscopy

Following metabolic labeling (and fixation for Mtb), 6 μL of cell suspension were spotted onto slides, covered with coverslips and sealed with adhesive. Microscopy was performed on a Nikon A1R confocal microscope equipped with a Plan Fluor 60× Oil immersion NA 1.30 objective. This instrument is equipped with a 405 nm violet laser, 488 nm blue laser and 561 nm green laser (for Aqua Amine, FITC/GFP and RFP channels, respectively). NIS-Elements AR software (Nikon, Inc.) was used to process images. All image acquisition and processing was executed under identical conditions for control and test samples.

Absorbance and Fluorescence Measurements of DMN-Tre

One μL of 10 mM DMN-Tre in H2O was added to 1 mL of mixtures of dioxane and water at different ratios. Absorbance spectra were recorded on a Varian Cary 50 UV-Visible spectrophotometer. Fluorescence spectra were recorded on a Photon Technology International Quanta Master 4 L-format scanning spectrofluorometer equipped with an LPS-220B 75-W xenon lamp and power supply, an A-1010B lamp housing with an integrated igniter, a switchable 814 photon counting/analog photomultiplier detection unit, and an MD5020 motor driver. Measurements were made in 1 cm×0.4 cm quartz cuvettes with a total sample volume of 1 mL.

No-Wash Imaging of Msmeg, Cg, and M. marinum by DMN-Tre and 6-FITre

Msmeg or Cg was grown to an $OD_{600}$ of 0.5 from a single colony (37° C. for Msmeg; 30° C. for Cg). To 500 μL of culture was added either 5 μL of 10 mM DMN-Tre or 10 mM 6-FITre in H2O. The bacteria were incubated for another 1 h (Msmeg) or 2 h (Cg), then placed under a coverslip and imaged directly. M. marinum (Mm) was stored as an OD 0.5 stock in 50% glycerol/50% 7H9+OADC. 1 mL of this frozen culture was thawed and the bacteria pelleted (3 min, 3,300× g) and resuspended in 2 mL of 7H9 liquid medium supplemented with 10% (v/v) oleate-albumin-dextrose-catalase enrichment (BBL Middlebrook OADC, 212351), 0.5% (v/v) glycerol, and 0.05% (w/v) Tween 80 (Sigma, P1754). The bacteria were incubated at 33° C. overnight (~16 h). To 500 μL of Mm culture was added 5 μL of 10 mM DMN-Tre or 10 mM 6-FITre in H2O. The bacteria were incubated at 33° C. for 6 h, then placed under a coverslip and imaged without washing.

No-Wash Labeling of Msmeg and Cg Over Time

Msmeg or Cg cells were grown to an $OD_{600}$ of 0.5 from a single colony as above. To 200 μL of culture was added 2 μL of 10 mM DMN-Tre in H2O. Aliquots were taken from this culture at the indicated time points, immediately placed under a coverslip, and imaged.

Labeling of Non-Mycomembrane Bearing Bacteria

Lm, Bs, Ec, and Sa were grown from single colonies at 37° C. overnight. The bacteria were diluted to an $OD_{600}$ of 0.4. To 1 mL aliquots of these bacteria, 10 μL of 10 mM DMN-Tre was added to reach a final concentration of 100 μM. The cells were then incubated at 37° C. for 2 h. Aliquots were taken and the cells were imaged under a coverslip. As controls, cells from the same $OD_{600}$=0.4 culture, without the addition of DMN-Tre, were also imaged.

Selective Labeling of Msmeg in the Presence of Other Bacterial Species.

Bacteria (Lm, Bs, Ec, and Sa) were grown overnight with shaking in media as noted above. The bacteria were diluted to $OD_{600}$=0.5, then 500 μL of each culture were mixed together to create 2 mL of mixed bacteria. One mL of Msmeg expressing mCherry was grown from a single colony overnight to $OD_{600}$ of 0.5. Both cultures were pelleted by centrifugation (3 min, 3,300×g) and resuspended in an identical volume of LB medium. To 540 μL of mix, 60 μL of Msmeg was added. Lastly, this final mixture of bacteria containing Msmeg and the four other non-mycomembrane bearing bacterial species was split into two 300 μL aliquots. To each group, 0.3 μL of 2 mg/mL Hoechst DNA stain (Thermo Fisher Scientific, 62249) was added to stain all the bacteria. To one of the two aliquots, 3 μL of 10 mM DMN-Tre were added, while no DMN-Tre was added to the other portion. The two aliquots were incubated with shaking at 37° C. for 1 h before a sample was taken out and imaged without washing.

Trehalose Competition of DMN-Tre Labeling in M. smegmatis

Msmeg was grown to $OD_{600}$=0.4 from a single colony as noted above. Then, the bacteria were divided into 100 μL aliquots. To these aliquots was added 1 μL of 10 mM DMN-Tre and 1 μL of 0, 10 or 100 mM trehalose in water. The bacteria were grown for another 1 hour, washed twice with PBS, resuspended in PBS, and examined by flow cytometry and microscopy.

Ebselen Inhibition Studies

Msmeg was grown to $OD_{600}$=0.4 from a single colony as noted above. Then, 500 μL aliquots of bacterial culture were incubated with 25, 50 or 100 μg/mL ebselen (Sigma-Aldrich, 60940-34-3) for 3 h. To these pre-treated samples was added 5 μL 10 mM DMN-Tre. The cultures were grown for another 1 h, washed twice with PBS, resuspended in PBS, and examined by flow cytometry and microscopy.

Growth Phase Studies

Msmeg was grown from a single colony to $OD_{600}$=0.5 or $OD_{600}$>2. Then, 500 μL aliquots of bacterial culture were incubated with 5 μL 10 mM DMN-Tre for 30 minutes, washed twice with PBS, resuspended in PBS, and examined by flow cytometry and microscopy.

DMN-Tre Labeling of Drug-Treated Msmeg and Mtb

Msmeg was grown to $OD_{600}$=0.4 from a single colony as noted above. Then, 500 μL aliquots of bacterial culture were incubated with control or drug cocktail (cocktail contents: 1 μg/mL ethambutol, 0.2 μg/mL rifampicin, 10 μg/mL SQ109 and 10 μg/mL isoniazid in 7H9 media) for 3 h in a 37° C. atmospheric incubator. To these pre-treated samples was added 5 μL 10 mM DMN-Tre. The cultures were grown for another 30 minutes, washed twice with PBS, resuspended in PBS, and examined by flow cytometry and microscopy.

For Mtb, cultures were made by inoculation of a 1-mL frozen stock into 50 mL Middlebrook 7H9 liquid medium supplemented with 10% (v/v) oleate-albumin-dextrose-catalase enrichment (BBL Middlebrook OADC, 212351), 0.5% (v/v) glycerol, and 0.05% (w/v) Tween 80 (Sigma, P1754) in a roller bottle. Cells were grown to $OD_{600}$=0.5 to begin experiments. Five hundred μL aliquots of bacterial culture were incubated with control or drug cocktail (cocktail contents: 1 μg/mL ethambutol, 0.2 μg/mL rifampicin, 10 μg/mL SQ109 and 10 μg/mL isoniazid in 7H9 media) for 3 h in a 37° C. atmospheric incubator followed by incubation with 100 μM DMN-Tre overnight (~16 h). Labeled cells were harvested by centrifugation (10 min, 3,000×g) then fixed in an equal volume of 2.5% glutaraldehyde. The cells were incubated at room temperature for 1 h, with occasional rotation of the tube to ensure sterilization of all internal surfaces prior to fluorescence and flow cytometry analysis.

Patient Recruitment and Sputum Sample Collection

Ethics approval for the study was provided by the University of the Witwatersrand Human Research Ethics Committee (clearance number: M110833). Participants for the study were approached at primary health care clinics; those willing to participate were then asked to visit the study clinic where informed consent was administered. Thereafter, a spot or overnight sputum sample was collected and transported to the lab for processing. Sputum was decontaminated by addition of an equal volume of 2.9% sodium citrate and 4% sodium hydroxide (NalC/NaOH), followed by incubation at room temperature for 20 minutes. Thereafter, the bacterial cells were harvested at 3900×g for 10 min and washed with 4.5 mL of 0.01 M phosphate buffered saline (PBS), pH 7.4 followed by resuspension in 2 mL Middlebrook 7H9 media supplemented with 0.5% Tween and OADC (oleic acid, albumin, dextrose, catalase; Becton Dickinson, South Africa). To disperse clumps, cells were vortexed briefly in the presence of 2 mm glass beads.

Microscopy Analysis of Mtb in Sputum Samples

Sputum samples from TB patients were isolated as described above. To 0.1 mL aliquots of these samples, 10 μL of 10 mM DMN-Tre was added to reach a final concentration of 1 mM. Samples were then incubated at 37° C. for the indicated times. Samples were fixed in a final concentration of 2.5% glutaraldehyde, and incubated at room temperature for 1 h, with occasional rotation of the tube to ensure sterilization of all internal surfaces. Prior to imaging, samples were resuspended in 30 μl of 1×PBS.

Auramine Vs DMN-Tre Smear Test

Auramine smear was performed according to standard conditions for kit. Briefly, NalC-NaOH-decontaminated sputum sample was smeared onto the slide and heat-fixed (heating block, 95° C., 5-10 min). Smears were then treated with Auramine O for 5 min, de-stained and then counter-stained before viewing in the FITC/GFP channel of a Zeiss Observer Z1-inverted fluorescence microscope.

For DMN-Tre labeling, the same sample was stained as follows: 100 μl of sample was incubated with 1 mM DMN-trehalose for 30 minutes at 37° C. followed by fixing in 2.5% glutaraldehyde for 1.5 h. Samples were then re-suspended in 30 μl 1×PBS, of which 20 μl was mounted on a 2% agarose pad for viewing in the FITC and DIC channels of a Zeiss Observer Z1-inverted fluorescence microscope.

Colony-Forming Units (CFU) Plating.

To determine CFU, cells were treated as needed and ten-fold serial dilutions were produced in complete 7H9 medium and plated on Middlebrook 7H10 agar plates (Difco, 262710) containing 10% OADC and 0.05% glycerol (v/v) without antibiotics. CFU were counted after 3 days (for Msmeg) and 14-17 days (for Mtb) of incubation at 37° C. in a humidified incubator.

Purification of C. glutamicum Trehalose Glycolipids

C. glutamicum cultures (200 mL) were incubated with 0.1 mM DMN-Tre or left untreated until stationary phase. Bacterial cell pellets were washed twice with PBS before subjecting to organic extraction. Cell wall glycolipids were isolated by sequentially extracting with 2:1, 1:1, 1:2 MeOH:$CH_3Cl$ mixtures, followed by concentration of organic extracts. Partial purification was achieved by preparative TLC (Analtech, 20×20 cm, 1 mm thickness) developed with 65:25:4 $CHCl_3$:MeOH:$H_2O$. Purity of glycolipid fractions was monitored by HPTLC (Uniplate HPTLC-GHL, 5×5 cm, 150 μm thickness), imaged with typhoon scanner (Amersham Biosciences, Typhoon 9410) to detect fluorescently labeled glycolipids and stained with 5% $H_2SO_4$ in MeOH with charring for standard glycolipid visualization.

Validation of DMN-Tre Labeled Glycolipids by Mass Spectrometry

C. glutamicum trehalose glycolipids were isolated as described above. Glycolipid samples were dissolved in 200 μL 2:1 $CHCl_3$:MeOH (HPLC grade) and filtered through a 0.45 μm PVDF membrane. Mass spectra were acquired on a Waters Q-tof Premier quadrupole time-of-flight mass spectrometer equipped with a nanoelectrospray ionization (nanoESI) source, located in the QB3/Chemistry Mass Spectrometry Facility at the University of California, Berkeley. Ions were formed in the positive ion mode from pulled borosilicate glass nanoESI tips. Mass spectra were recorded over the range, mass-to-charge ratio (m/z)=100 to 4000. Data acquisition was controlled using MassLynx software (version 4.1, Waters). Tandem mass spectrometry was performed on three precursor ions using collision induced dissociation (CID) fragmentation to show loss of lipid tails from DMN-Tre labeled mycolates.

Axenic MTB Culture Time-Course Experiment

The laboratory strain of Mycobacterium tuberculosis, H37Rv, was grown axenically to an optical density (600 nm) of approximately 0.5 (i.e. exponential growth phase). Five equal volumes of 200 μl, assigned to a time-course points at 30 min, 1 h, 2 h, 3 h and overnight, were stained with 1 mM DMN-trehalose at 37° C. Three independent biological replicates for each time-point were prepared. Unlabeled samples of M. tuberculosis served as a control. Following incubation, samples were analyzed by flow cytometry using a CytoFlex (Beckman Coulter). Samples were aliquoted into separate wells of a 96-well, flat-bottomed culture plate. The flow cytometer was calibrated using "Daily Fluorophore QC beads (Beckman Coulter). Two gates were constructed using signal detected with the violet laser (KO525A channel). One corresponded to unlabeled M. tuberculosis while the other corresponded to all cells positive for DMN-trehalose. Flow cytometry data was for 50000 events or for 2 min, whichever variable was true first (according to the acquisition setting outlined below). To prevent carry-over, wells containing water separated each sample which was run for 2 min. DMN-trehalose staining was plotted as a percentage of total events.

Synthetic Procedures

All chemical reagents obtained from commercial suppliers were used without further purification. Reversed-phase HPLC was performed on a Varian Pro Star system with a Varian UV-Vis detector model 345 (210, 254 nm) on a Dynamax Microsorb C-18 preparative column (21.4×250 mm) at a flow rate of 20 mL/min. NMR spectra were obtained on a Varian INOVA-600 spectrometer at ambient temperature at the Stanford Department of Chemistry NMR Facility.

DMN-Trehalose (3)

6-Amino trehalose (1) (31 mg, 0.091 mmol) and 4-N,N-dimethylaminonaphthalic anhydride (2) (22 mg, 0.091 mmol, 1 equiv.) were added to a flask along with 2 mL of absolute ethanol. To the mixture was added 20 mg of sodium bicarbonate. The yellow suspension was heated to 85° C. under a nitrogen atmosphere and stirred for 6 h. The now red-orange solution was then concentrated by rotary evaporation and the suspension was dissolved in 10 mL of $H_2O$, filtered through a plug of cotton, and reconcentrated. The remaining orange residue was purified by reversed-phased HPLC (5-80% MeCN in $H_2O$) and lyophilized to yield DMN-Tre (3) (22.1 mg, 0.039 mmol, 43%) as a bright orange solid.

$^1$H NMR (600 MHz, $D_2O$) δ 8.21 (d, J=8.5 Hz, 1H), 8.13 (d, J=7.3 Hz, 1H), 7.95 (d, J=8.4 Hz, 1H), 7.46 (t, J=7.9 Hz, 1H), 6.90 (d, J=8.6 Hz, 1H), 4.97 (d, J=3.8 Hz, 1H), 4.53 (d, J=3.7 Hz, 1H), 4.23 (d, J=6.2 Hz, 2H), 4.03 (dt, J=12.3, 6.4 Hz, 1H), 3.79 (t, J=9.4 Hz, 1H), 3.73-3.61 (m, 4H), 3.56 (dd, J=12.1, 5.4 Hz, 1H), 3.44 (t, J=9.5 Hz, 1H), 3.18 (t, J=9.5 Hz, 1H), 3.07 (m, 1H), 3.07 (s, 6H).

$^{13}$C NMR (151 MHz, 5% $CD_3OD$ in $D_2O$) δ 166.16, 165.34, 157.94, 134.16, 133.31, 132.29, 130.33, 125.19, 124.05, 121.44, 113.21, 111.71, 94.03, 93.86, 93.82, 73.84, 73.62, 73.47, 73.03, 72.08, 71.94, 70.61, 70.19, 61.53, 44.93, 41.80. HRMS (ESI-TOF, m/z): calcd for $C_{26}H_{32}N_2O_{12}$ [M+Na]$^+$ 587.1847, found 587.1849.

DMN-Glucose (5)

6-Amino-6-deoxy methyl glucoside (4) (38 mg, 0.20 mmol) and 4-N,N-dimethylaminonaphthalic anhydride (2) (48 mg, 0.20 mmol, 1 equiv.) were added to a flask along with 4 mL of absolute ethanol. To the suspension was added 40 mg of sodium bicarbonate. The orange suspension was then heated to 85° C. under a nitrogen atmosphere and stirred for 6 h. The clear red-orange solution was then concentrated, dissolved in 3 mL of $H_2O$, and filtered through a plug of cotton. The orange solution was then purified by reversed-phase HPLC (5-80% MeCN in $H_2O$) and lyophilized to yield DMN-Glc (5) (46.5 mg, 0.12 mmol, 56%) as a bright orange solid.

$^1$H NMR (600 MHz, $D_2O$) δ 8.37-8.24 (m, 1H), 8.21 (t, J=5.9 Hz, 1H), 8.03 (t, J=6.2 Hz, 1H), 7.53 (d, J=4.0 Hz, 1H), 7.03-6.90 (m, 1H), 4.58 (d, J=3.5 Hz, 1H), 4.32 (t, J=11.4 Hz, 1H), 4.23 (d, J=13.7 Hz, 1H), 3.88 (t, J=10.0 Hz, 1H), 3.63 (t, J=9.3 Hz, 1H), 3.57 (dd, J=9.7, 3.8 Hz, 1H), 3.43 (t, J=9.4 Hz, 1H), 3.10 (d, J=2.7 Hz, 6H), 2.90 (s, 3H).

$^{13}$C NMR (151 MHz, 5% $CD_3OD$ in $D_2O$) δ 166.07, 165.18, 157.79, 134.05, 133.28, 132.14, 130.24, 124.99, 123.76, 121.21, 112.94, 111.29, 99.90, 74.10, 73.84, 72.24, 69.07, 55.20, 44.86, 41.99. HRMS (ESI-TOF, m/z): calcd for $C_{21}H_{24}N_2O_7$ [M+Na]$^+$ 439.1476, found 439.1472.

DOCTRINE OF EQUIVALENTS

This description of the invention has been presented for the purposes of illustration and description. It is not intended to be exhaustive or to limit the invention to the precise form described, and many modifications and variations are possible considering the teaching above. The embodiments were chosen and described to best explain the principles of the invention and its practical applications. This description will enable others skilled in the art to best utilize and practice the invention in various embodiments and with various modifications that are best suited for a specific need. The scope of the invention is defined by the following claims.

The invention claimed is:

1. A method for detecting metabolically active bacteria of interest in a sample, the method comprising:
    contacting the sample with an aqueous solution having an excess of a trehalose-solvatochromic dye conjugate that comprises:
        a trehalose moiety, and
        a solvatochromic dye linked to the trehalose moiety, wherein the solvatochromic dye is one of: 4-DMAP, 4-DMN, 6-DMN, Nile Red, 3-HC, 3-MC, PRODAN, Anthradan, NBD or a derivative thereof; and
    detecting a spectroscopic signal from the solvatochromic dye moiety of the trehalose-solvatochromic dye conjugate, the spectroscopic signal indicating the uptake of the trehalose-solvatochromic dye conjugate by the metabolically active bacteria of interest in the sample;
    wherein the detecting step is performed without removal of the excess of trehalose-solvatochromic dye conjugate in the sample, and wherein the indicative spectroscopic signal is readily detectable over the total spectroscopic signal provided by the excess of trehalose-solvatochromic dye conjugate remaining in the aqueous solution of the sample.

2. The method of claim 1, wherein the outer cell membrane of the bacteria of interest is a mycomembrane rich in hydrophobic mycolates.

3. The method of claim 2, wherein the mycomembrane mycolates include trehalose mycolates.

4. The method of claim 1, wherein the bacteria of interest is capable of metabolic uptake of trehalose.

5. The method of claim 1, wherein the bacteria of interest metabolically uptakes trehalose with high specificity.

6. The method of claim 1, wherein the bacteria of interest possess acyl transferase antigen 85 (Ag85) protein complex capable of trehalose mycolylation, thereby promoting the uptake of trehalose by the bacteria of interest.

7. The method of claim 1, wherein the bacteria of interest belong to *Actinobacteria* phylum.

8. The method of claim 7, wherein the bacteria of interest are mycobacteria or corynebacteria.

9. The method of claim 1, wherein, the trehalose moiety of the conjugate is a trehalose analog.

10. The method of claim 1, wherein the trehalose-solvatochromic dye conjugate has formula:

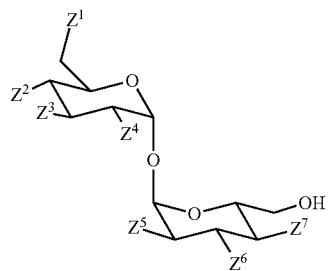

wherein one and only one of $Z^1$-$Z^7$ is a linked solvatochromic dye and the rest of $Z^1$-$Z^7$ are OH.

11. The method of claim 10, wherein the trehalose-solvatochromic dye conjugate has formula:

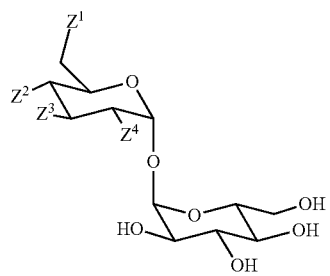

wherein one and only one of $Z^1$-$Z^4$ is a linked solvatochromic dye and the rest of $Z^1$-$Z^4$ are OH.

12. The method of claim 11, wherein $Z^1$ is the linked solvatochromic dye.

13. The method of claims 1, wherein the sample is a biological sample.

14. The method of claim 13, wherein the biological sample is selected from the group of: sputum, blood, serum, plasma, urine, bronchoalveolar lavage fluid, buccal swab, and tissue samples.

15. The method of claim 14, wherein the biological sample is a sample from a subject suspected of having, or at risk of infection with the bacteria of interest.

16. The method of claim 15, wherein the biological sample is a sample from a subject suspected of having, or at risk of infection with *Mycobacterium tuberculosis*.

17. The method of claim 1, wherein the sample is an environmental sample.

18. The method of claim 17, wherein the sample is taken from an environment selected from the group of: air, water, or inanimate surface.

19. The method of claim 17, wherein the environmental sample is a sample known or suspected to have contact with subject or subjects suspected of having, or at risk of infection with the bacteria of interest.

20. The method of claim 17, wherein the environmental sample is a sample known or suspected to have contact with subject or subjects suspected of having, or at risk of infection with *Mycobacterium tuberculosis*.

21. The method of claim 1, wherein the bacteria of interest is one or more selected from the group of: *M. tuberculosis, M. avium* (or *M. avium-intracellulare*), *M. leprae* (particularly *M. leprae* infection leading to tuberculoid leprosy), *M. kansasii, M. fortuitum, M. chelonae, M. absecessus, M. marinum, M. Nocardia, M. xenopi, M. simiae, M. szulgai, M. scrofulaceum, M. malmoense, M. terrae-nonchromogenicum complex, M. haemophilum, M. genavense, M. celatum, M. interjectum, M. confluentis, M. triplex, M. lentiflavum, M. branderi, M. conspicuum, M. cookii, M. asiaticum, M. marinum, M. gordonae, M. fortuitum, M. chelonae-abscessu,* and *M. mucogenicum*.

22. The method of claim 1, wherein the metabolically active bacteria of interest is selected from the group of: *Mycobacterium tuberculosis, Mycobacterium leprae,* or *Corynebacterium diphtheriae*.

23. The method of claim 1, wherein the bacteria of interest is present extracellularly.

24. The method of claim 1, wherein the bacteria of interest is present inside a eukaryotic cell.

25. The method of claim 1, wherein the detecting step is performed without washing the sample subsequent to the contacting step and prior to the detecting step.

26. The method of claim 1, wherein the spectroscopic signal fluorescence intensity is enhanced approximately 700-fold.

27. The method of claim 1, wherein the solvatochromic dye is linked to the trehalose moiety as shown in the following formula without optional linker L:

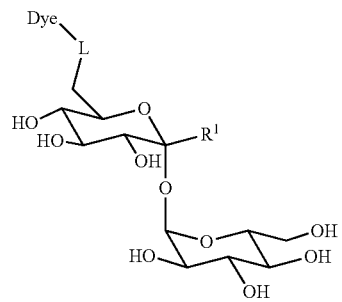

* * * * *